(12) United States Patent
Keller et al.

(10) Patent No.: US 10,138,520 B2
(45) Date of Patent: Nov. 27, 2018

(54) DIAGNOSTIC MIRNA MARKERS FOR ALZHEIMER

(71) Applicants: Siemens Aktiengesellschaft, Munich (DE); Siemens Healthcare Diagnostics Holding GmbH, Eschborn (DE)

(72) Inventors: Andreas Keller, Püttlingen (DE); Cord Friedrich Stähler, Hirschberg an der Bergstraße (DE); Eckart Meese, Hütschenhausen (DE); Andreas Kappel, Glashuetten (DE); Christina Backes, Saarbrücken (DE); Petra Leidinger, Wadern (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 349 days.

(21) Appl. No.: 14/442,439

(22) PCT Filed: Oct. 29, 2013

(86) PCT No.: PCT/EP2013/072567
§ 371 (c)(1),
(2) Date: May 13, 2015

(87) PCT Pub. No.: WO2014/075911
PCT Pub. Date: May 22, 2014

(65) Prior Publication Data
US 2016/0273040 A1 Sep. 22, 2016

(30) Foreign Application Priority Data
Nov. 16, 2012 (EP) .................................. 12192974

(51) Int. Cl.
*A61K 48/00* (2006.01)
*C12Q 1/6883* (2018.01)
*C12Q 1/6809* (2018.01)
*G06F 19/22* (2011.01)

(52) U.S. Cl.
CPC ......... *C12Q 1/6883* (2013.01); *C12Q 1/6809* (2013.01); *G06F 19/22* (2013.01); *C12Q 2600/118* (2013.01); *C12Q 2600/158* (2013.01); *C12Q 2600/16* (2013.01); *C12Q 2600/178* (2013.01)

(58) Field of Classification Search
CPC ....................................................... C12Q 1/68
See application file for complete search history.

(56) References Cited

U.S. PATENT DOCUMENTS

| 7,687,616 B1 | 3/2010 | Bentwich et al. |
| 9,493,832 B2 | 11/2016 | Vilanova et al. |
| 2009/0081640 A1 | 3/2009 | Umansky et al. |
| 2010/0234445 A1 | 9/2010 | Lui et al. |
| 2010/0280099 A1 | 11/2010 | Elmen |
| 2012/0225925 A1* | 9/2012 | Sozzi ................... C12Q 1/6886 514/44 A |
| 2015/0197805 A1 | 7/2015 | Umansky et al. |

FOREIGN PATENT DOCUMENTS

| CN | 101861399 A | 10/2010 |
| EP | 2077326 A1 | 7/2009 |
| EP | 2112235 A1 | 10/2009 |
| WO | WO-2009/009457 A1 | 1/2009 |
| WO | WO-2009/025852 A2 | 2/2009 |
| WO | WO-2009/036236 A1 | 3/2009 |
| WO | WO-2011/057003 A2 | 5/2011 |
| WO | WO-2012/036433 A2 | 3/2012 |
| WO | WO-2012/145363 A1 | 10/2012 |
| WO | WO-2013/065819 A1 | 5/2013 |
| WO | WO-2013/072920 A2 | 5/2013 |

OTHER PUBLICATIONS

Office Action dated Apr. 26, 2016 issued in U.S. Appl. No. 14/442,756.
NCBI Reference Sequence "Homo sapiens glutamate metabotropic receptor 7 (GRM7), RefSeqGene on chromosome 3".
Office Action dated Jun. 16, 2016 issued in U.S. Appl. No. 14/442,858.
Schulz, et al. (2002) Neuroscience Letters "Characterization of three novel isoforms of the metabotrobic glutamate receptor 7 (GRM7)".
Gao Kai et al., "Study on Parkinson's", Chinese Journal of Neurology (2011), 780-782.
Office Action dated Apr. 19, 2016, Issued in Chinese Patent Application No. 201380069445.9.
Regina Margis et al., "Identification of Blood microRNAs Associated to Parkinson's Disease", Journal of Biotechnology vol. 152 (2011) 96-101.
Search Report dated Apr. 19, 2016, issued in Chinese Patent Application No. 201380069445.9.
Kim et al. (2007), "A microRNA Feedback Circuit in Midbrain Dopamine Neurons", Science; 317(5842): pp. 1220-1224.
Martins et al. (2011), "Convergence of miRNA Expression Profiling, Alpha-Synuclein Interacton and GWAS in Parkinson's Disease", PLoS One, vol. 6, Iss 10; e25443; pp. 1-11.
Office Action dated Apr. 19, 2016 issued in co-pending Chinese Patent Application No. 2013/80069445.9.
Barbato, C., et al. (2009), "Searching for MIND: MicroRNAs in Neurodegenerative Diseases", *Journal of Biomedicine and Biotechnology*, 14(1): 8 pages.

(Continued)

*Primary Examiner* — Kimberly Chong
(74) *Attorney, Agent, or Firm* — Harness, Dickey and Pierce, P.L.C.

(57) ABSTRACT

The invention relates to methods for diagnosing Alzheimer's Disease (AD) with miRNA markers. Diagnosis of AD Towards the identification of biomarkers for diagnosis of AD, a comprehensive analysis of miRNA expression patterns was obtained. Significantly deregulated miRNAs were identified.

19 Claims, 12 Drawing Sheets
Specification includes a Sequence Listing.

(56) References Cited

OTHER PUBLICATIONS

De Smaele, et al. (2010), "MicroRNAs as biomarkers for CNS cancer and other disorders", *Brain Res.* 1138: 100-111.
European Search Report dated Aug. 21, 2013 issued in European Patent Application No. 12192979.8.
European Search Report dated May 3, 2013 issued in European Patent Application No. 12192979.8.
International Search Report and Written Opinion dated Dec. 3, 2013 issued in PCT Patent Application No. PCT/EP2013/065819.
International Search Report and Written Opinion dated Mar. 7, 2014 issued in PCT Patent Application No. PCT/EP2013/072920.
Margis, R., et al. (2011), "Identification of blood microRNAs associated to Parkinsonis disease", *Journal of Biotechnology*, 152: 96-101.
Schipper, H., et al. (2007), "MicroRNA Expression in Alzheimer Blood Mononuclear Cells", *Gene Regulation and Systems Biology*, 1: 263-274.
Office Action dated Feb. 2, 2017 Issued in U.S. Appl. No. 14/442,858.
Office Action dated Apr. 10, 2017 issued in U.S. Appl. No. 14/442,756.
European Search Report dated Aug. 2, 2013 issued in European Patent Application No. 12192974.9.
FASTX—Toolkit; http://hannonlab.cshl.edu/fastx_toolkit/; retrieved on Nov. 19, 2012, 10:16 a.m.
Geekiyanage, H., et al. (2012), "Blood serum miRNA: Non-invasive biomarkers for Alzheimer's disease", *Exp Neurol.* 235(2): 491-496.
Hudson, G., et al. (2012), "No consistent evidence for association between mtDNA variants and Alzheimer disease", *Neurology*, 78: 1038-1042.
International Search Report and Written Opinion dated Mar. 7, 2014 issued in PCT Patent Application No. PCT/EP2013/072567.
Keller, A., et al. (2011), "Toward the blood-borne miRNome of human diseases", *Nature Methods*, 8(10): 841-843.
Lange, J., et al. (2010), miRNA biomarkers from blood—A promising approach for minimally invasive diagnostic testing, *Gerburtshilfe Und Frauenheilkunde*, 70(2): 137-141—English Abstract Only.
Maes, O., et al. (2009), "MicroRNA: Implications for Alzheimer Disease and other Human CNS Disorders", *Current Genomics*, 10: 154-168.
Malaplate-Armand, C., et al. (2009), "Biomarkers for early diagnosis of Alzheimer's disease: Current update and future directions", *Revue Neurologique*, 165: 511-520—English Abstract Only.
Satoh, J. (2010), "MircoRNAs and Their Therapeutic Potential for Human Diseases: Aberrant MicroRNA Expression in Alzheimer's Disease Brains", *J. Pharmacol Sci.* 114: 269-275.
TAM tool; http://202.38.126.151/hmdd/tools/tam.html; retrieved on Nov. 19, 2012, 10:14 a.m.
Chinese Office Action dated May 27, 2016 in corresponding Chinese Patent Application CN 201380068818.0—English translation.
Friedländer, M., et al. (2012), "miRDeep2 accurately identifies known and hundreds of novel microRNA genes in seven animal clades", Nucleic Acids Research, 40(1): 37-52.
Office Action dated Aug. 29, 2016 issued in U.S. Appl. No. 14/442,756.
Office Action dated Oct. 23, 2017 issued in U.S. Appl. No. 14/442,756.
Biomarkers Definitions Working Group (2001) "Biomarkers and surrogate endpoints: Preferred definitions and conceptual framework." Clinical Pharmacology & Therapeutics, v.69:89-95.
Office Action dated Apr. 26, 2018 issued in U.S. Appl. No. 14/442,858.
Strimbu, et al. (2010) "What are Biomarkers?" Curr. Opin. HIV AIDS V:5(6):463-6.
Office Action dated Oct. 9, 2018 issued in U.S. Appl. No. 14/442,858.

* cited by examiner

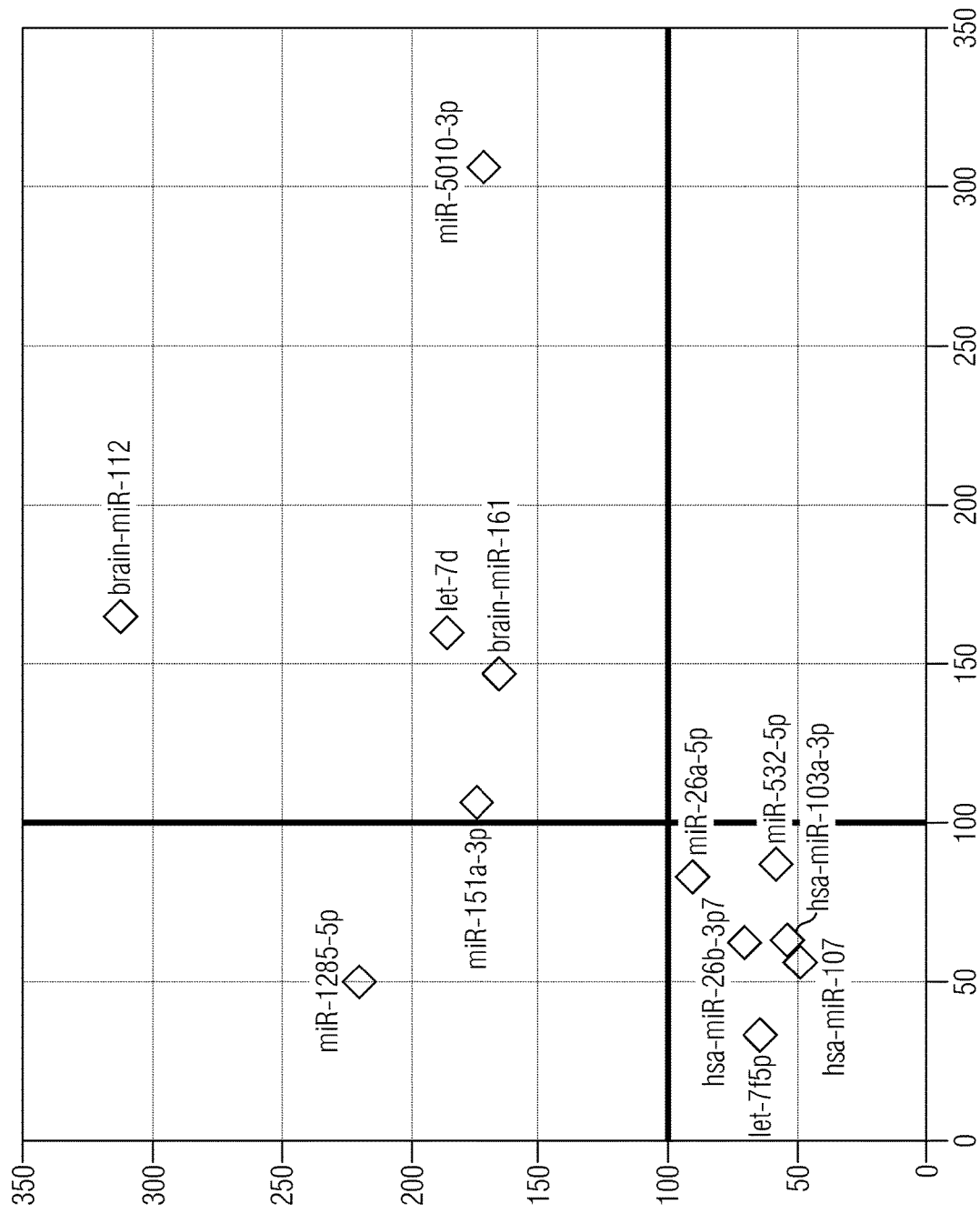

DIAGNOSTIC MIRNA MARKERS FOR ALZHEIMER

PRIORITY STATEMENT

This application is a national phase application under 35 U.S.C. § 371 of PCT International Application No. PCT/EP2013/072567 which has an International filing date of 29 Oct. 2013, which designated the United States of America, and which claims priority to European patent application number 12192974.9 filed 16 Nov. 2012. The entire contents of each patent application referenced above are hereby incorporated by reference.

REFERENCE TO A SEQUENCE LISTING

This application contains references to amino acid sequences and/or nucleic acid sequences which have been submitted concurrently herewith as the sequence listing text file 62095355_1.TXT file size 34 KiloBytes (KB), created on 1 Nov. 2017. The aforementioned sequence listing is hereby incorporated by reference in its entirety pursuant to 37 C.F.R. § 1.52(e)(5).

FIELD OF THE INVENTION

The invention relates to novel markers for diagnosing Alzheimer's disease.

BACKGROUND OF THE INVENTION

Very recently, molecular diagnostics has increasingly gained in importance. It has found an entry into the clinical diagnosis of diseases (inter alia detection of infectious pathogens, detection of mutations of the genome, detection of diseased cells and identification of risk factors for pre-disposition to a disease).

In particular, through the determination of gene expression in tissues, nucleic acid analysis opens up very promising new possibilities in the study and diagnosis of disease.

Nucleic acids of interest to be detected include genomic DNA, expressed mRNA and other RNAs such as MicroR-NAs (abbreviated miRNAs). MiRNAs are a new class of small RNAs with various biological functions (A. Keller et al., Nat Methods. 2011 8(10):841-3). They are short (average of 20-24 nucleotide) ribonucleic acid (RNA) molecules found in eukaryotic cells. Several hundred different species of microRNAs (i.e. several hundred different sequences) have been identified in mammals. They are important for post-transcriptional gene-regulation and bind to complementary sequences on target messenger RNA transcripts (mRNAs), which can lead to translational repression or target degradation and gene silencing. As such they can also be used as biologic markers for research, diagnosis and therapy purposes.

Alzheimer's disease (AD), also known in medical literature as Alzheimer disease, is the most common form of dementia. Alzheimer's disease is characterised by loss of neurons and synapses in the cerebral cortex and certain subcortical regions and leads to a gross degeneration in these regions. In AD protein misfolding and aggregation (formation of so-called "plaques") in the brain is caused by accumulation of abnormally folded A-beta and tau proteins in the affected tissues.

Early symptoms are often mistaken to be age-related problems. In the early stages, the most common symptom is difficulty in remembering recent events. When AD is suspected, the diagnosis is usually confirmed with functional tests that evaluate behaviour and cognitive abilities, often followed by imaging analysis of the brain. Imaging methods used for this purpose include computed tomography (CT), magnetic resonance imaging (MRI), single photon emission computed tomography (SPECT), and positron emission tomography (PET). In a patients already having dementia, SPECT appears to be superior in differentiating Alzheimer's disease from other possible causes, compared with the usual attempts employing mental testing and medical history analysis. A new technique known as PiB PET has been developed for directly and clearly imaging beta-amyloid deposits in vivo using a tracer that binds selectively to the beta-amyloid deposits. Beta-amyloid deposits. Recently, a miRNA diagnostic test from serum has been proposed (Geekiyanage et al., Exp Neurol. 2012 June; 235(2):491-6.)

Symptoms can be similar to other neurological disorders. Diagnosis can be time consuming, expensive and difficult. In particular, the reliable and early diagnosis of Alzheimer based on non-invasive molecular biomarkers remains a challenge. Till today, early diagnosis of AD remains a great challenge. So far, findings of an autopsy or biopsy represent the most reliable diagnostics for this common disease The attempt to report the presence of beta-amyloid not only in the brain, but also in other tissues, e.g. the skin, showed only limited relevance for diagnosing AD. (Malaplate-Armand C, Desbene C, Pillot T, Olivier J L. Diagnostic biologique de la maladie d'Alzheimer: avancées, limites et perspectives. Rev Neurol 2009; 165:511-520). Thus, in the recent past, different imaging as well as in vitro diagnostic markers have been proposed in order to improve the AD diagnosis. Most importantly, biomarkers that can detect AD in pre-clinical stages are in the focus, however, such markers can so far be only reliably detected in cerebrospinal fluid (CSF). One prominent example is the combination of beta-amyloid-1-42 and tau. In addition, molecular genetics analyses of single nucleotide polymorphisms (SNPs) in the DNA of patients have been proposed to provide a risk estimation of the presence of AD. In addition to variants in genes, several studies have described an association between AD and genetic variation of mitochondrial DNA (mtDNA). Here, no consistent evidence for the relation of mtDNA variants and AD could be reported Hudson G, Sims R, Harold D, et al.; GERAD1 Consortium. No consistent evidence for association between mtDNA variants and Alzheimer disease. Neurology 2012; 78:1038-1042. However, although the heritability of AD is comparably high (60-80%), epigenetic and persistent factors also may play an important role.

Therefore, there exists an unmet need for an efficient, simple, reliable diagnostic test for AD.

OBJECT OF THE INVENTION

The technical problem underlying the present invention is to provide biological markers allowing to diagnose, screen for or monitor Alzheimer's disease, predict the risk of developing Alzheimer's disease, or predict an outcome of Alzheimer's disease.

SUMMARY OF THE INVENTION

Before the invention is described in detail, it is to be understood that this invention is not limited to the particular component parts of the process steps of the methods described as such methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is also to be understood that plural forms include singular and/or plural referents unless the context clearly dictates otherwise. It is moreover to be understood that, in case parameter ranges are given which are delimited by numeric values, the ranges are deemed to include these limitation values.

In its most general terms, the invention relates to a collection of miRNA markers useful for the diagnosis, prognosis and prediction of Alzheimer's Disease.

BRIEF DESCRIPTION OF THE FIGURES

FIG. 7 shows the qRT-PCR validation of selected miR-NAs, the up-regulated miRNAs brain-mir-112, brain-mir-161, hsa-let-7d-3p, hsa-miR-5010-3p, hsa-miR-26b-3p, hsa-miR-26a-5p, hsa-miR-1285-5p, and hsa-miR-151a-3p as well as the down-regulated markers hsa-miR-103a-3p, hsa-miR-107, hsa-miR-532-5p, and hsa-let-7f-5p. X-axis: expression of AD samples vs. control determined by NGS, y-axis: expression of AD samples vs. control determined by qRT-PCR.

DETAILED DESCRIPTION OF THE INVENTION

Definitions

Figure 1:
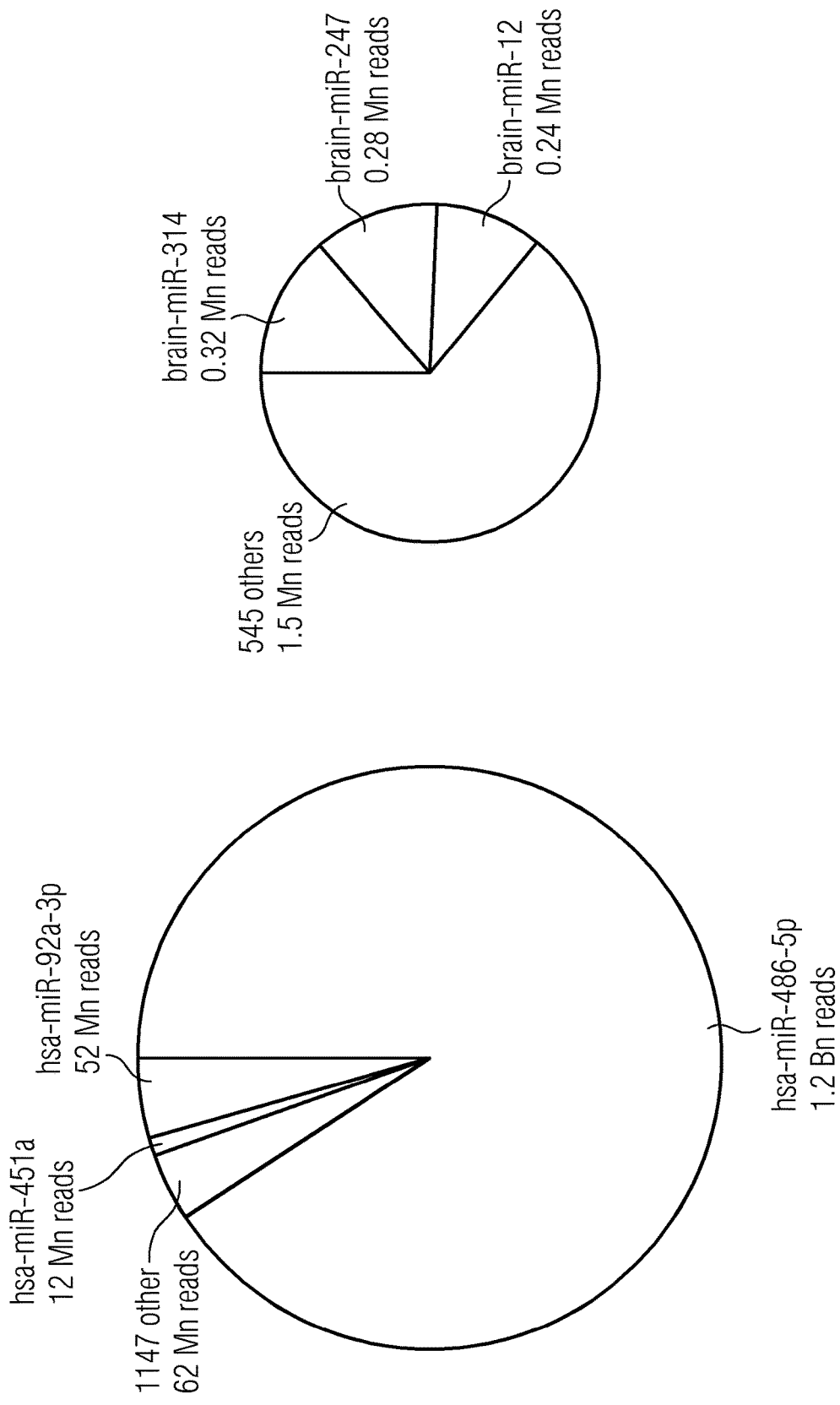
FIG. 1 shows the distribution of reads obtained by high throughput sequencing. The left pie chart shows that 95% of known miRNAs belong to one miRNA while all other 1.000 detected known markers make up only 5%. The novel detected miRNAs on the right hand side are much less abundant than the most frequently detected miRNA.

Unless defined otherwise, technical and scientific terms used herein have the same meaning as commonly understood by one of ordinary skill in the art to which this invention belongs.

The term "predicting an outcome" of a disease, as used herein, is meant to include both a prediction of an outcome of a patient undergoing a given therapy and a prognosis of a patient who is not treated.

An "outcome" within the meaning of the present invention is a defined condition attained in the course of the disease. This disease outcome may e.g. be a clinical condition such as "relapse of disease", "remission of disease", "response to therapy", a disease stage or grade or the like.

A "risk" is understood to be a probability of a subject or a patient to develop or arrive at a certain disease outcome. The term "risk" in the context of the present invention is not meant to carry any positive or negative connotation with regard to a patient's wellbeing but merely refers to a probability or likelihood of an occurrence or development of a given event or condition.

The term "clinical data" relates to the entirety of available data and information concerning the health status of a patient including, but not limited to, age, sex, weight, menopausal/hormonal status, etiopathology data, anamnesis data, data obtained by in vitro diagnostic methods such as blood or urine tests, data obtained by imaging methods, such as x-ray, computed tomography, MRI, PET, spect, ultrasound, electrophysiological data, genetic analysis, gene expression analysis, biopsy evaluation, intraoperative findings.

The term "classification of a sample" of a patient, as used herein, relates to the association of said sample with at least one of at least two categories. These categories may be for example "high risk" and "low risk"; or high, intermediate and low risk; wherein risk is the probability of a certain event occurring in a certain time period, e.g. occurrence of disease, progression of disease, etc. It can further mean a category of favourable or unfavourable clinical outcome of disease, responsiveness or non-responsiveness to a given treatment or the like. Classification may be performed by use of an algorithm, in particular a discriminate function. A simple example of an algorithm is classification according to a first quantitative parameter, e.g. expression level of a nucleic acid of interest, being above or below a certain threshold value. Classification of a sample of a patient may be used to predict an outcome of disease or the risk of developing a disease. Instead of using the expression level of a single nucleic acid of interest, a combined score of several nucleic acids of interest of interest may be used. Further, additional data may be used in combination with the first quantitative parameter. Such additional data may be clinical data from the patient, such as sex, age, weight of the patient, disease grading etc.

A "discriminant function" is a function of a set of variables used to classify an object or event. A discriminant function thus allows classification of a patient, sample or event into a category or a plurality of categories according to data or parameters available from said patient, sample or event. Such classification is a standard instrument of statistical analysis well known to the skilled person. E.g. a patient may be classified as "high risk" or "low risk", "in need of treatment" or "not in need of treatment" or other categories according to data obtained from said patient, sample or event. Classification is not limited to "high vs. low", but may be performed into a plurality of categories, grading or the like. Examples for discriminant functions which allow a classification include, but are not limited to discriminant functions defined by support vector machines (SVM), k-nearest neighbors (kNN), (naive) Bayes models, or piecewise defined functions such as, for example, in subgroup discovery, in decision trees, in logical analysis of data (LAD) an the like.

The term "expression level" refers, e.g., to a determined level of expression of a nucleic acid of interest. The term "pattern of expression levels" refers to a determined level of expression com-pared either to a reference nucleic acid, e.g. from a control, or to a computed average expression value, e.g. in DNA-chip analyses. A pattern is not limited to the comparison of two genes but is also related to multiple comparisons of genes to reference genes or samples. A certain "pattern of expression levels" may also result and be determined by comparison and measurement of several nucleic acids of interest disclosed hereafter and display the relative abundance of these transcripts to each other. Expression levels may also be assessed relative to expression in different tissues, patients versus healthy controls, etc.

A "reference pattern of expression levels", within the meaning of the invention shall be understood as being any pattern of expression levels that can be used for the comparison to another pattern of expression levels. In a preferred embodiment of the invention, a reference pattern of expression levels is, e.g., an average pattern of expression levels observed in a group of healthy or diseased individuals, serving as a reference group.

In the context of the present invention a "sample" or a "biological sample" is a sample which is derived from or has been in contact with a biological organism. Examples for biological samples are: cells, tissue, body fluids, biopsy specimens, blood, urine, saliva, sputum, plasma, serum, cell culture supernatant, and others.

A "probe" is a molecule or substance capable of specifically binding or interacting with a specific biological molecule. The term "primer", "primer pair" or "probe", shall have ordinary meaning of these terms which is known to the person skilled in the art of molecular biology. In a preferred embodiment of the invention "primer", "primer pair" and "probes" refer to oligonucleotide or polynucleotide molecules with a sequence identical to, complementary too, homologues of, or homologous to regions of the target molecule or target sequence which is to be detected or quantified, such that the primer, primer pair or probe can specifically bind to the target molecule, e.g. target nucleic acid, RNA, DNA, cDNA, gene, transcript, peptide, polypeptide, or protein to be detected or quantified. As understood herein, a primer may in itself function as a probe. A "probe" as understood herein may also comprise e.g. a combination of primer pair and internal labeled probe, as is common in many commercially available qPCR methods.

A "gene" is a set of segments of nucleic acid that contains the information necessary to produce a functional RNA product in a controlled manner. A "gene product" is a biological molecule produced through transcription or expression of a gene, e.g. an mRNA or the translated protein.

A "miRNA" is a short, naturally occurring RNA molecule and shall have the ordinary meaning understood by a person skilled in the art. A "molecule derived from an miRNA" is a molecule which is chemically or enzymatically obtained from an miRNA template, such as cDNA.

The term "array" refers to an arrangement of addressable locations on a device, e.g. a chip device. The number of locations can range from several to at least hundreds or thousands. Each location represents an independent reaction site. Arrays include, but are not limited to nucleic acid arrays, protein arrays and antibody-arrays. A "nucleic acid array" refers to an array containing nucleic acid probes, such as oligonucleotides, polynucleotides or larger portions of genes. The nucleic acid on the array is preferably single stranded. A "microarray" refers to a biochip or biological chip, i.e. an array of regions having a density of discrete regions with immobilized probes of at least about 100/cm2.

A "PCR-based method" refers to methods comprising a polymerase chain reaction PCR. This is a method of exponentially amplifying nucleic acids, e.g. DNA or RNA by enzymatic replication in vitro using one, two or more primers. For RNA amplification, a reverse transcription may be used as a first step. PCR-based methods comprise kinetic or quantitative PCR (qPCR) which is particularly suited for the analysis of expression levels). When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR). The term "PCR based method" comprises both end-point PCR applications as well as kinetic/real time PCR techniques applying special fluorophors or intercalating dyes which emit fluorescent signals as a function of amplified target and allow monitoring and quantification of the target. Quantification methods could be either absolute by external standard curves or relative to a comparative internal standard.

The term "next generation sequencing" or "high throughput sequencing" refers to high-throughput sequencing technologies that parallelize the sequencing process, producing thousands or millions of sequences at once. Examples include Massively Parallel Signature Sequencing (MPSS) Polony sequencing, 454 pyrosequencing, Illumina (Solexa) sequencing, SOLiD sequencing, Ion semiconductor sequencing, DNA nanoball sequencing, Helioscope™ single molecule sequencing, Single Molecule SMR™ sequencing, Single Molecule real time (RNAP) sequencing, Nanopore DNA sequencing.

The term "marker" or "biomarker" refers to a biological molecule, e.g., a nucleic acid, peptide, protein, hormone, etc., whose presence or concentration can be detected and correlated with a known condition, such as a disease state, or with a clinical outcome, such as response to a treatment.

In particular, the invention relates to a method of classifying a sample of a patient suffering from or at risk of developing Alzheimer's Disease, wherein said sample is a blood sample, said method comprising the steps of:

a) determining in said sample an expression level of at least one miRNA selected from the group consisting of miRNAs having the sequence SEQ ID NO 59, SEQ ID NO 65, SEQ ID NO 1 to SEQ ID NO 58, SEQ ID NO 60 to SEQ ID NO 64 and SEQ ID NO 66 to SEQ ID NO 170, b) comparing the pattern of expression level(s) determined in step a) with one or several reference pattern(s) of expression levels; and c) classifying the sample of said patient from the outcome of the comparison in step b) into one of at least two classes.

A reference pattern of expression levels may, for example, be obtained by determining in at least one healthy subject the expression level of at least one miRNA selected from the group consisting of miRNAs having the sequence SEQ ID NO 59, SEQ ID NO 65, SEQ ID NO 1 to SEQ ID NO 58, SEQ ID NO 60 to SEQ ID NO 64 and SEQ ID NO 66 to SEQ ID NO 170.

It is within the scope of the invention to assign a numerical value to an expression level of the at least one miRNA determined in step a).

It is further within the scope of the invention to mathematically combine expression level values to obtain a pattern of expression levels in step (b), e.g. by applying an algorithm to obtain a normalized expression level relative to a reference pattern of expression level(s).

In a further aspect the invention relates to a method for diagnosing Alzheimer's Disease, predicting risk of developing Alzheimer's Disease, or predicting an outcome of Alzheimer's Disease in a patient suffering from or at risk of developing Alzheimer's Disease, said method comprising the steps of:

a) determining in a blood sample from said patient, the expression level of at least one miRNA selected from the group consisting of miRNAs with the sequence SEQ ID NO 59, SEQ ID NO 65, SEQ ID NO 1 to SEQ ID NO 58, SEQ ID NO 60 to SEQ ID NO 64 and SEQ ID NO 66 to SEQ ID NO 170, b) comparing the pattern of expression level(s) determined in step a) with one or several reference pattern(s) of expression levels; and c) diagnosing Alzheimer's Disease, predicting a risk of developing Alzheimer's Disease, or predicting an outcome of Alzheimer's Disease from the outcome of the comparison in step b).

According to an aspect of the invention, said at least one miRNA is selected from the group consisting of miRNAs with the sequence SEQ ID NO 59, SEQ ID NO 65, SEQ ID NO 1 and SEQ ID NO 56.

According to an aspect of the invention, step a) comprises determining the expression level of the miRNAs: brain-mir-112, hsa-miR-5010-3p, hsa-miR-103a-3p, hsa-miR-107, hsa-let-7d-3p, hsa-miR-532-5p, and brain-mir-161.

According to an aspect of the invention, step a) comprises in step a) determining the expression level of 5 miRNAs selected from the signatures consisting of brain-mir-112 hsa-miR-5010-3p hsa-miR-1285-5p hsa-miR-151a-3p hsa-let-7f-5p,
hsa-miR-3127-3p hsa-miR-1285-5p hsa-miR-425-5p hsa-miR-148b-5p hsa-miR-144-5p,
hsa-miR-3127-3p hsa-miR-3157-3p hsa-miR-148b-5p hsa-miR-151a-3p hsa-miR-144-5p,
hsa-miR-3127-3p hsa-miR-1285-5p hsa-miR-425-5p hsa-miR-151a-3p hsa-miR-144-5p,
hsa-miR-1285-5p brain-mir-112 hsa-miR-5010-3p hsa-miR-151a-3p hsa-let-7a-5p,
hsa-miR-5001-3p hsa-miR-1285-5p hsa-miR-425-5p hsa-miR-148b-5p hsa-miR-144-5p,
hsa-miR-3127-3p hsa-miR-1285-5p hsa-miR-148b-5p hsa-miR-151a-3p hsa-miR-144-5p,
hsa-miR-1285-5p hsa-miR-5010-3p hsa-miR-425-5p hsa-miR-148b-5p hsa-miR-144-5p,
hsa-miR-1285-5p hsa-miR-5010-3p hsa-miR-151a-3p hsa-miR-144-5p hsa-let-7a-5p,
hsa-miR-1285-5p brain-mir-112 hsa-miR-425-5p hsa-miR-151a-3p hsa-miR-144-5p,
hsa-miR-5001-3p hsa-miR-1285-5p brain-mir-112 hsa-miR-151a-3p hsa-let-7f-5p,
hsa-miR-1285-5p hsa-miR-5010-3p hsa-miR-148b-5p hsa-miR-144-5p hsa-let-7f-5p,
hsa-miR-1285-5p hsa-miR-3157-3p hsa-miR-148b-5p hsa-miR-151a-3p hsa-miR-144-5p,
hsa-miR-5001-3p hsa-miR-1285-5p hsa-miR-5010-3p hsa-miR-151a-3p hsa-let-7f-5p,
brain-mir-431 hsa-miR-1285-5p hsa-miR-3157-3p hsa-miR-151a-3p hsa-miR-144-5p,
hsa-miR-3127-3p hsa-miR-1285-5p brain-mir-112 hsa-miR-425-5p hsa-miR-151a-3p,
hsa-miR-1285-5p hsa-miR-5010-3p hsa-miR-151a-3p hsa-miR-144-5p hsa-let-7f-5p,
hsa-miR-550a-5p hsa-miR-1285-5p brain-mir-112 hsa-miR-151a-3p hsa-let-7f-5p,
hsa-miR-1285-5p brain-mir-112 hsa-miR-148b-5p hsa-miR-151a-3p hsa-miR-144-5p, and
hsa-miR-5001-3p brain-mir-112 hsa-miR-5010-3p hsa-miR-151a-3p hsa-let-7f-5p.

According to an aspect of the invention, the expression levels of a plurality of miRNAs are determined as expression level values and step (b) comprises mathematically combining the expression level values of said plurality of miRNAs.

It is within the scope of the invention to apply an algorithm to the numerical value of the expression level of the at least one miRNA determined in step a) to obtain a disease score to allow classification of the sample or diagnosis, prognosis or prediction of the risk of developing Alzheimer's Disease, or prediction of an outcome of Alzheimer's Disease. A non-limiting example of such an algorithm is to compare the numerical value of the expression level against a threshold value in order to classify the result into one of two categories, such as high risk/low risk, diseased/healthy or the like. A further non-limiting example of such an algorithm is to combine a plurality of numerical values of expression levels, e.g. by summation, to obtain a combined score. Individual summands may be normalized or weighted by multiplication with factors or numerical values representing the expression level of an miRNA, numerical values representing clinical data, or other factors.

It is within the scope of the invention to apply a discriminant function to classify a result, diagnose disease, predict an outcome or a risk.

According to an aspect of the invention, the expression level in step (a) is obtained by use of a method selected from the group consisting of a Sequencing-based method, an array based method and a PCR-based method.

According to an aspect of the invention, the expression levels of at least 2, 3, 4, 5, 6, 7, 8, 9, 10, 11, or 12 miRNAs are determined to obtain a pattern of expression levels.

According to an aspect of the invention, step a) comprises in step a) determining the expression level of the miRNAs: hsa-let-7f-5p, hsa-miR-1285-5p, hsa-miR-107, hsa-miR-103a-3p, hsa-miR-26b-3p, hsa-miR-26a-5p, hsa-miR-532-5p, hsa-miR-151a-3p, brain-mir-161, hsa-let-7d-3p, brain-mir-112, and hsa-miR-5010-3p.

The invention further relates to a kit for performing the methods of the invention, said kit comprising means for determining in said blood sample from said patient, an expression level of at least one miRNA selected from the group consisting of miRNAs with the sequence SEQ ID NO 59, SEQ ID NO 65, SEQ ID NO 1 to SEQ ID NO 58, SEQ ID NO 60 to SEQ ID NO 64 and SEQ ID NO 66 to SEQ ID NO 170.

The means for determining the expression level of said at least one miRNA may comprise an oligonucleotide probe for detecting or amplifying said at least one miRNA, means for determining the expression level based on an array-based method, a PCR-based method, a sequencing-based method or any other suitable means for determining the expression level.

According to an aspect of the invention, the kit further comprises at least one reference pattern of expression levels for comparing with the expression level of the at least one miRNA from said sample. The reference pattern of expression may include at least one digital or numerical information and may be provided in any readable or electronically readable form, including, but not limited to printed form, electronically stored form on a computer readable medium, such as CD, smart card, or provided in downloadable form, e.g. in a computer network such as the internet.

The invention further relates to computer program product useful for performing the methods of the invention, comprising
  means for receiving data representing an expression level of at least one miRNA in a patient blood sample selected from the group consisting of miRNAs with the sequence SEQ ID NO 59, SEQ ID NO 65, SEQ ID NO 1 to SEQ ID NO 58, SEQ ID NO 60 to SEQ ID NO 64 and SEQ ID NO 66 to SEQ ID NO 170,
  means for receiving data representing at least one reference pattern of expression levels for comparing with the expression level of the at least one miRNA from said sample,
  means for comparing said data representing the expression level of the at least one miRNA in a patient sample, and
  optionally means for determining a diagnosis of Alzheimer's Disease, a prediction of a risk of developing Alzheimer's Disease, or a prediction of an outcome of Alzheimer's Disease from the outcome of the comparison in step b).

The computer program product may be provided on a storable electronic medium, such as a solid state memory, disk, CD or other. It may be stored locally on a computer. It may be implemented as network-based program or application, including a web- or internet-based application. It may be implemented in a diagnostic device, such as an analyzer instrument. It may be operably connected to a device for outputting information, such as a display, printer or the like.

EXAMPLES

Additional details, features, characteristics and advantages of the object of the invention are further disclosed in the following description and figures of the respective examples, which, in an exemplary fashion, show preferred embodiments of the present invention. However, these examples should by no means be understood as to limit the scope of the invention.

The invention relates to methods for diagnosing Alheimer's Disease with miRNA markers.

Diagnosis of Alzheimer's Disease can be challenging in patients presenting with generally age-related syndromes such as forgetfulness. In particular, it is difficult to diagnose the earliest stages of disease. However, it would be particularly desirable to have a reliable diagnostic test for this stage of disease, as the chance of therapeutic and social intervention is better during this early disease stage.

Here, the abundance of miRNAs in blood samples of Alzheimer's Disease patients has been compared in an unbiased approach against healthy controls and patients suffering from other neuronal disorders. This approach involved a massive effort of sequencing miRNAs from samples and thus was open to the discovery of novel markers not yet described in the prior art. Further, the use of blood samples as a source of expression information of miRNA markers has several tangible advances which are not available in other sample sources such as serum or tissue, such as ease of sample procurement and handling, sample preparation, and robustness and consistency of expression patterns.

Materials and Methods

Patient Cohorts

The expression of miRNAs in peripheral blood of a total of 219 patients and healthy controls was determined, either by NGS or by qRT-PCR or both. Blood was obtained from patients with Alzheimer's Disease (AD) (n=106), patients with Mild Cognitive Impairment (MCI) (n=21), patients with Multiple Sclerosis (Clinically Isolated Syndrome, CIS) (n=17), patients with Parkinson's Disease (PD) (n=9), patients with Mild Depression (DEP) (n=15), Bipolar Disorder (BD) (n=15), Schizophrenia (Schiz) (n=14), and from healthy controls (n=22).

First, samples from AD patients (n=48), MCI patients (n=20) and healthy controls (n=22) were analyzed by Next-generation sequencing. For validation purposes the expression of single miRNAs was analyzed using qRT-PCR in the same samples as used for NGS, if enough RNA was available. The number of samples was further expanded by further samples from patients with AD, CIS, PD, DEP, BD, and Schiz, resulting in a total of 205 samples analyzed by qRT-PCR. In detail, a total of 95 samples from AD patients, 19 samples from MCI patients, 17 samples from CIS patients, 9 samples from PD patients, 15 samples from DEP patients, 15 samples from BD patients, 14 samples from Schiz patients, and 21 samples from healthy controls were analyzed.

RNA Isolation

Total RNA including miRNA was isolated using the PAXgene Blood miRNA Kit (Qiagen) following the manufacturer's recommendations. Isolated RNA was stored at −80° C. RNA integrity was analyzed using Bioanalyzer 2100 (Agilent) and concentration and purity were measured using NanoDrop 2000 (Thermo Scientific). A total of four samples (three controls and one RRMS) failed the quality criteria and were excluded from the study.

Library Preparation and Next-Generation Sequencing

For the library preparation, 200 ng of total RNA was used per sample, as determined with a RNA 6000 Nano Chip on the Bioanalyzer 2100 (Agilent). Preparation was performed following the protocol of the TruSeq Small RNA Sample Prep Kit (Illumina). Concentration of the ready prepped libraries was measured on the Bioanalyzer using the DNA 1000 Chip. Libraries were then pooled in batches of six samples in equal amounts and clustered with a concentration of 9 pmol in one lane each of a single read flowcell using the cBot (Illumina). Sequencing of 50 cycles was performed on a HiSeq 2000 (Illumina). Demultiplexing of the raw sequencing data and generation of the fastq files was done using CASAVA v.1.8.2.

NGS Data Analysis

The raw illumina reads were first preprocessed by cutting the 3' adapter sequence using the programm fastx_clipper from the FASTX-Toolkit (http://hannonlab.cshl.edu/fastx_toolkit/). Reads shorter than 18 nts after clipping were removed. The remaining reads are reduced to unique reads and their frequency per sample to make the mapping steps more time efficient. For the remaining steps, we used the miRDeep2 pipeline. These steps consist of mapping the reads against the genome (hg19), mapping the reads against miRNA precursor sequences from mirbase release v18, summarizing the counts for the samples, and the prediction of novel miRNAs. Since the miRDeep2 pipeline predicts novel miRNAs per sample, the miRNAs were merged afterwards as follows: first, the novel miRNAs per sample that have a signal-to-noise ratio of more than 10 were extracted. Subsequently, only those novel miRNAs that are located on the same chromosome were merged, and both their mature forms share an overlap of at least 11 nucleotides.

Quantitative Real Time-PCR (qRT-PCR)

Out of the NGS results 7 miRNAs were selected that were deregulated in both, the comparison between patients with Alzheimer's Disease and patients with Mild Cognitive Impairment, and the comparison between patients with Alzheimer's Disease and healthy individuals. Five of the seven miRNAs, namely hsa-miR-5010-3p, hsa-miR-103a-3p, hsa-miR-107, hsa-let-7d-3p, and hsa-miR-532-5p were already known mature miRNAs included in miRBase, two miRNAs, namely brain-mir-112 and brain-mir-161, were newly identified and not yet included in miRBase. As endogenous control the small nuclear RNA RNU48 as used.

The miScript PCR System (Qiagen) was used for reverse transcription and qRT-PCR. A total of 200 ng RNA was converted into cDNA using the miScript Reverse Transcription Kit according to the manufacturers' protocol. For each RNA we additionally prepared 5 µl reactions containing 200 ng RNA and 4 µl of the 5× miScript RT Buffer but no miScript Reverse Transcriptase Mix, as negative control for the reverse transcription (RT– control). The qRT-PCR was performed with the miScript SYBR® Green PCR Kit in a total volume of 20 µl per reaction containing 1 µl cDNA according to the manufacturers' protocol. For each miScript Primer Assay we additionally prepared a PCR negative-control with water instead of cDNA (non-template control, NTC).

Bioinformatics Analysis

First the read counts were normalized using standard quantile normalization. All miRNAs with less than 50 read counts were excluded from further considerations. Next, we calculated for each miRNA the area under the receiver operator characteristic curve (AUC), the fold-change, and the significance value (p-value) using t-tests. All significance values were adjusted for multiple testing using the Benjamini Hochberg approach. The bioinformatics analyses have been carried out using the freely available tool. R. Furthermore, we carried out a miRNA enrichment analysis using the TAM tool (http://202.38.126.151/hmdd/tools/tam.html).

Computing Combined Scores

Briefly, to compute a combined expression score for n up-regulated markers and m down-regulated markers the difference d between the expression value $x_{(a)}$ of a patient a and the average expression value of all controls µ is determined. For down-regulated markers, the difference can be multiplied by (−1), thus yielding a positive value. The differences for n markers can be added up to yield a combined score Z, such that $Z_{(a)} = \Sigma d_{(1-n)}(\text{upregulated}) + \Sigma(-1)d_{(1-m)}(\text{down-regulated})$ Wherein $d = x_{(a)} - \mu$ To make combined scores between different marker scores comparable (e.g. to compare a (n+m)=7 marker score against a (n+m)=12 marker score, the combined score can be divided by (n+m):

$Z\text{comp} = 1/(n+m)(\Sigma d_{(1-n)}(\text{upregulated}) + \Sigma(-1)d_{(1-m)}(\text{down-regulated}))$ Other factors can be applied to the individual summands d of the combined score or the combined score Z as a whole.

Results

Screening Using High-Throughput Sequencing

To detect potential Alzheimer biomarkers a high-throughput sequencing of n=22 controls samples (C), n=48 Alzheimer patient (AD) samples and n=20 Mild Cognitive Impairment (MCI) samples was carried out. Precisely, Illumina HiSeq 2000 sequencing and multiplexed 8 samples on each sequencing lane was carried out. Thereby, 1150 of all human mature miRNAs in at least a single sample could be detected.

TABLE 1

Patient Cohorts

| Disease | Cohort Size Screening | Cohort Size Replication |
|---|---|---|
| Controls | 22 | 21 |
| Alzheimer (US) | 48 | 86 |
| Alzheimer (GER) | 0 | 9 |
| Parkinson Disease | 0 | 9 |
| Mild Cognitive Impairment | 20 | 18 |
| Schizophrenia | 0 | 14 |
| Bipolar disease | 0 | 15 |
| Multiple Sclerosis (CIS) | 0 | 17 |
| Depression | 0 | 15 |
| SUM | 90 | 204 |

The most abundant miRNAs were hsa-miR-486-5p with an average read-count of 13,886,676 and a total of 1.2 billion reads mapping to this miRNA, hsa-miR-92a-3p with an average of 575,359 reads and a total of 52 million reads mapping to this miRNA and miR-451a with an average of 135,012 reads and a total of 12 million reads mapping to this miRNA. The distribution of reads mapping to the three most abundant and all other miRNAs is shown in FIG. 1 (left pie chart). Additionally, 548 novel mature miRNA candidates were detected that have been previously not present in the Sanger miRBase. These miRNA candidates have generally however been much less abundant as compared to the known human miRNAs. The most abundant one, denoted as brain-miR-314 was detected on average with 3,587 reads per sample and a total of 322,868 reads. Second highest expressed miRNA, brain-miR-247 was present on average with 3,112 and with a total of 280,115 reads, third most abundant miRNA brain-miR-12 at an average of 2,630 and a total of 236,728 reads. In the list of all, novel and known miRNAs, brain-miR-314 would be ranked on position 37, i.e., 36 known human miRNAs were more abundant than the highest abundant novel one. While a total of 1.4 Bn reads mapped to the known miRNAs, only 2.3 Mn mapped to the novel miRNA candidates. This relation shows that a very high sequencing capacity is required to reach the sensitivity in order to detect rare variants of novel miRNAs in human blood samples. Interestingly, as the right pie chart in FIG. 1 denotes, the candidate miRNAs are much more equally distributed as compared to the known ones, where the most abundant miRNA was responsible for 91% of all reads.

To detect potential biomarker candidates two-tailed t-tests and adjusted the significance values for multiple testing using Benjamini Hochberg adjustment were computed. All markers with adjusted significance values below 0.05 were considered statistically significant. Additionally, the area under the receiver operator characteristics curve (AUC) was computed to understand the specificity and sensitivity of miRNAs for Alzheimer diagnosis. Altogether, 170 significantly dys-regulated miRNAs we detected, 55 markers were significantly down-regulated in Alzheimer, while 115 were significantly up-regulated. A list of the respective 170 markers is presented in Supplemental Table 1 a and b. These 170 miRNA markers have the corresponding sequences SEQ ID NO 1 to SEQ ID NO 170 in the attached sequence protocol.

A list of all miRNA molecules described herein is given in Supplemental Table 4 containing an overview of the miRNA markers, including sequence information.

It is noted that the mature miRNa originate from miRNA precursor molecules of length of around 120 bases. Several examples exists where the miRNA precursors vary from each other while the subset of the around 20 bases belonging to the mature miRNA are identical. Thus, novel mature miRNAs can have the same sequence but different SEQ ID NO identifiers.

MiRNA markers are denoted by their common name (e.g. has-miR-144-5p or hsa-let 7f-5p) and are searchable in publically available databases. In this invention there are also described novel miRNA markers which have been named with names beginning with the prefix "brain-miR". They are listed in supplemental table 2 with their sequence and their SEQ ID NO according to the sequence protocol.

Figure 2:
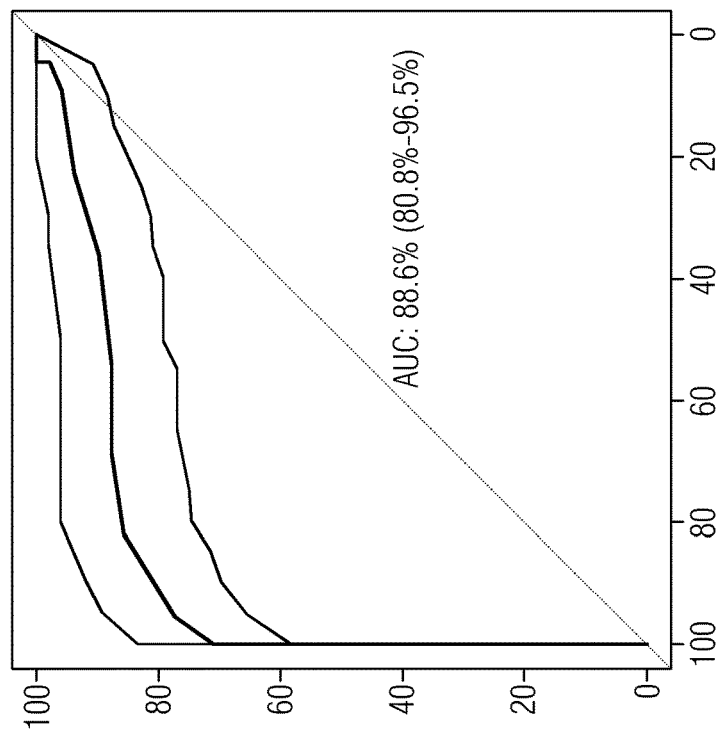
FIG. 2 shows the ROC curve for the most up-regulated miRNA, gene expression data obtained by NGS. X-axis: specificity, y-axis: sensitivity.
Figure 3:
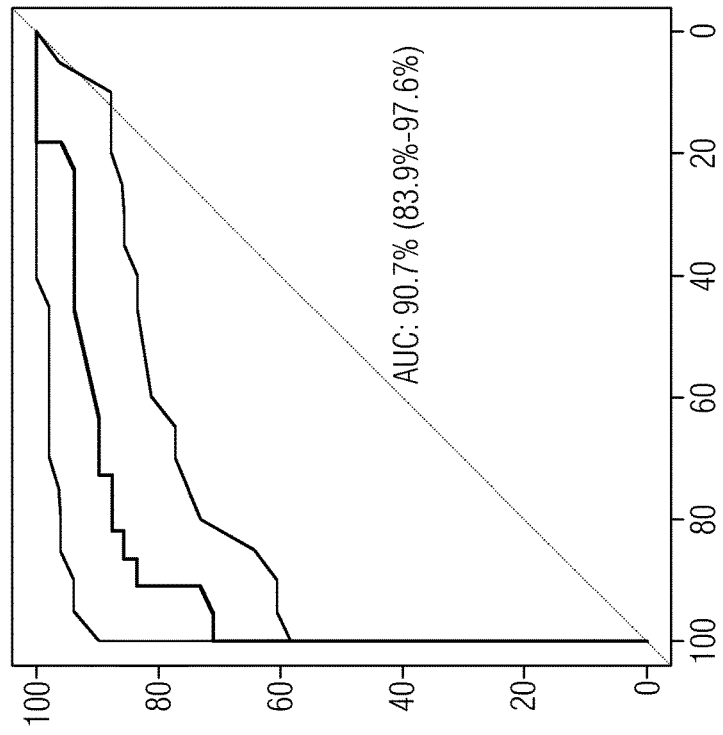
FIG. 3 shows the ROC curve for the most down-regulated miRNA, gene expression data obtained by NGS. X-axis: specificity, y-axis: sensitivity.

The ROC curves for the most up-regulated marker (hsa-miR-30d-5p with p-value of $8*10^{-9}$) as well as the most down-regulated marker (hsa-miR-144-5p with p-value of $1.5*10^{-5}$) are presented in FIGS. 2 and 3, where the high AUC value indicates that already one single miRNA might have sufficient power to differentiate between cases and controls. Both miRNAs have however already been describe with many other human pathologies including different neoplasms and thus are non-specific for AD. Remarkably, the set of significant biomarkers also contained also 58 miRNAs that had so far not been reported, which have been designated with miRNA Names beginning with. Of these, only 10 were down-regulated while the majority of 48 miRNAs was highly up-regulated in AD.

To understand whether the detected biomarkers are also dys-regulated in MCI patients t-tests and AUC values for the comparison of healthy controls versus MCI were likewise computed. Here, ten markers remained statistically significant following adjustment for multiple testing. Of these, 8 were down-while 2 were up-regulated in MCI patients. Notably, 9 of them have been likewise significantly dys-regulated in MCI patients, namely hsa-miR-29c-3p, hsa-miR-29a-3p, hsa-let-7e-5p, hsa-let-7a-5p, hsa-let-7f-5p, hsa-miR-29b-3p, hsa-miR-98, hsa-miR-425-5p and hsa-miR-181a-2-3p. Only miRNA hsa-miR-223-3p was just significant in MCI patients while not in AD patients. A full list of all MCI biomarkers, identified as SEQ ID NO 171-235 in the attached sequence listing is presented in Supplemental Table 3. It is noted that mature miRNA originate from miRNA precursor molecules of length of around 120 bases. Several examples exists where the miRNA precursors vary from each other while the subset of the around 20 bases belonging to the mature miRNA are identical. Thus, novel mature miRNAs can have the same sequence but different identifiers.

Figure 4:
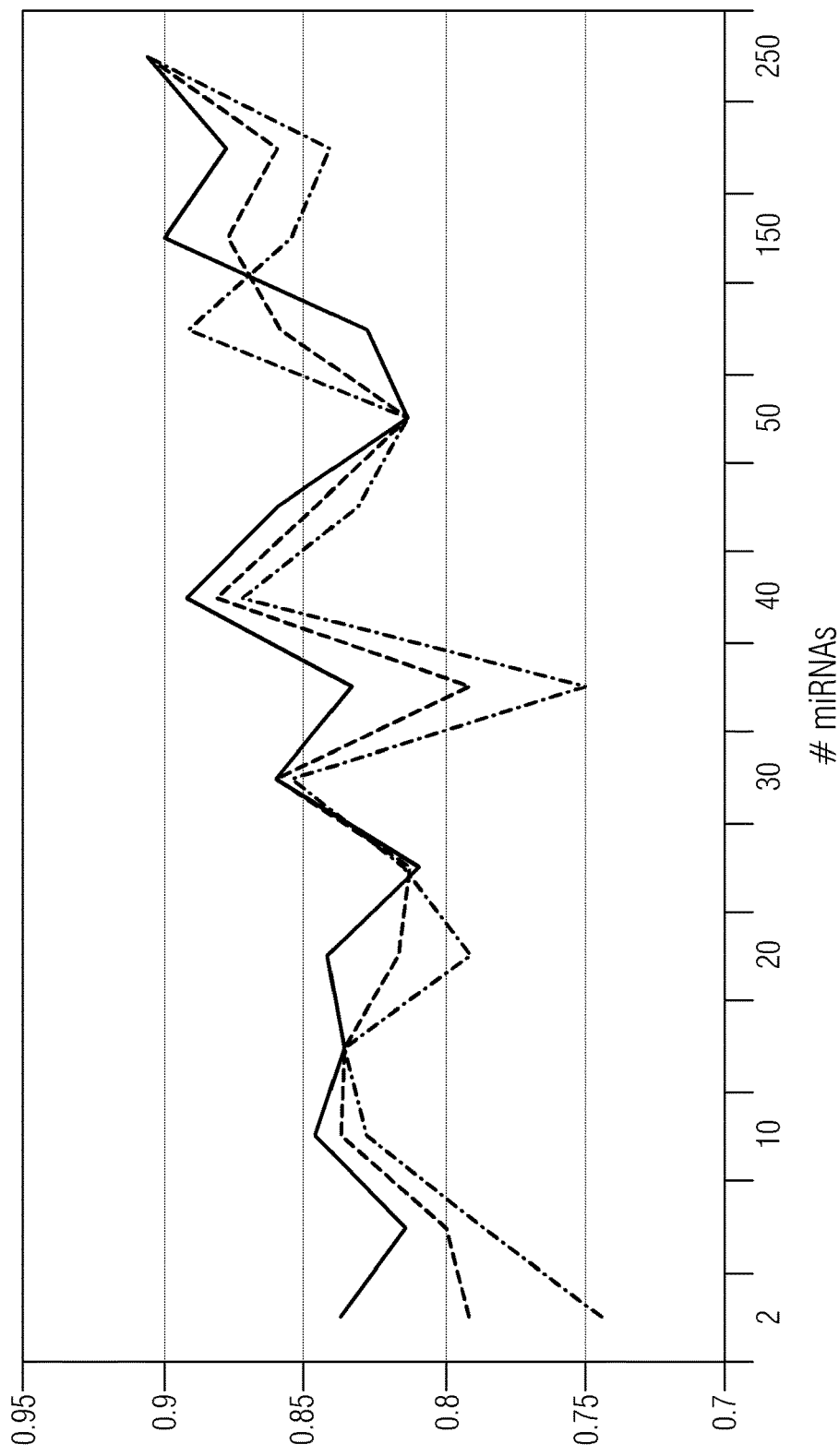
FIG. 4 shows increased performance by using marker combinations. The x-axis shows the number of miRNAs, the y axis shows the classification of performance, gene expression data obtained by NGS (solid line: sensitivity, broken line: accuracy, broken and dotted line: specificity).
Figure 6:
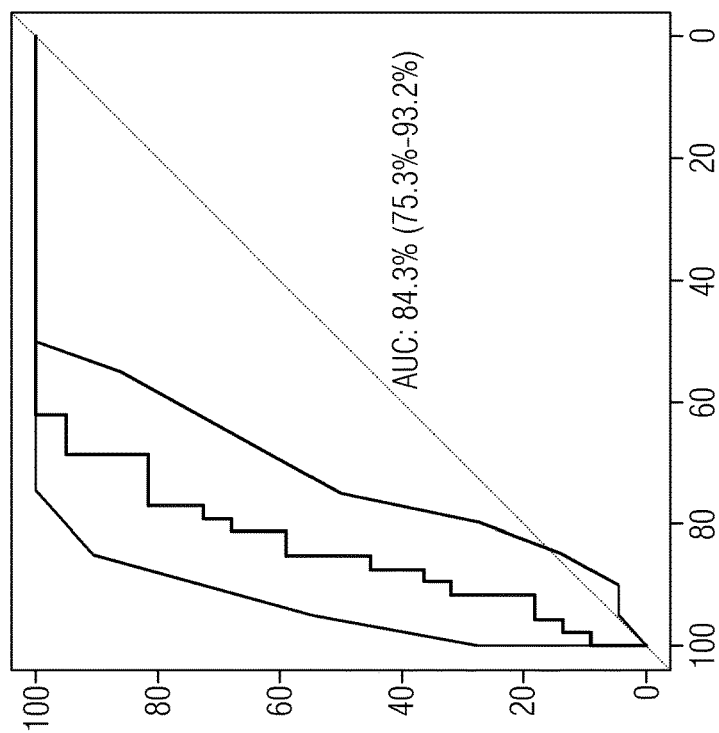
FIG. 6 shows the ROC curve for the 7-marker signature of FIG. 5, gene expression data obtained by NGS.
Figure 5:
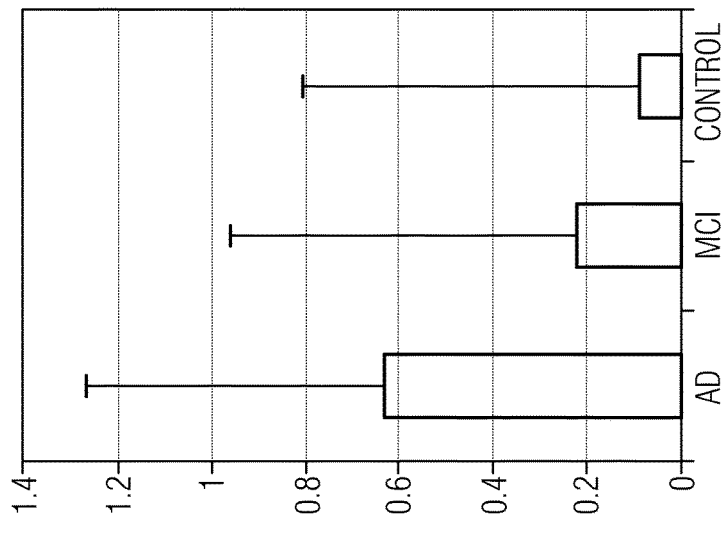
FIG. 5 shows a combined score of AD, MCI and controls for the 7-marker signature brain-mir-112, hsa-miR-5010-3p, hsa-miR-103a-3p, hsa-miR-107, hsa-let-7d-3p, hsa-miR-532-5p, and brain-mir-161. The combined score (y-axis) was obtained using high throughput sequencing.
Figure 9:
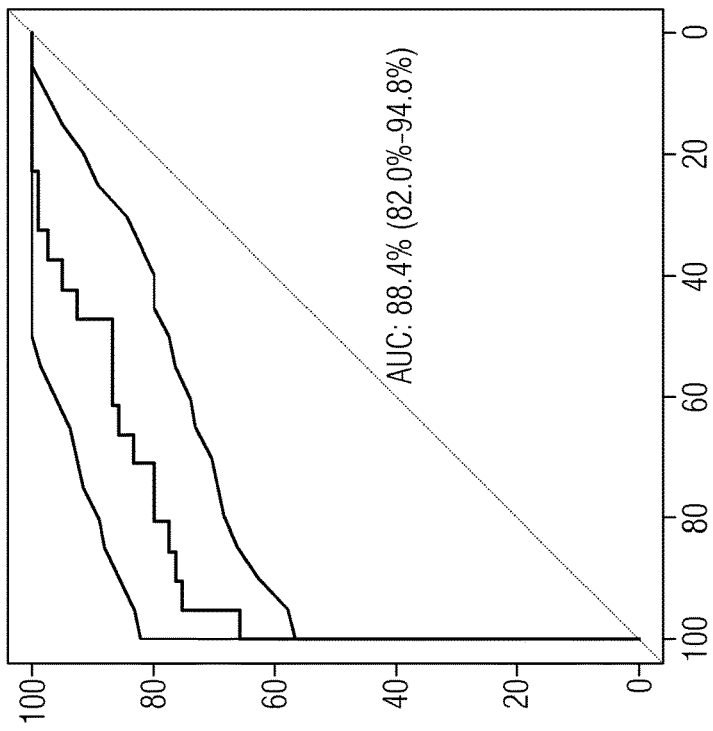
FIG. 9 shows the ROC curve for the 7-marker signature brain-mir-112, hsa-miR-5010-3p, hsa-miR-103a-3p, hsa-miR-107, hsa-let-7d-3p, hsa-miR-532-5p, and brain-mir-161, qRT-PCR. X-axis: specificity, y-axis: sensitivity.
Figure 8:
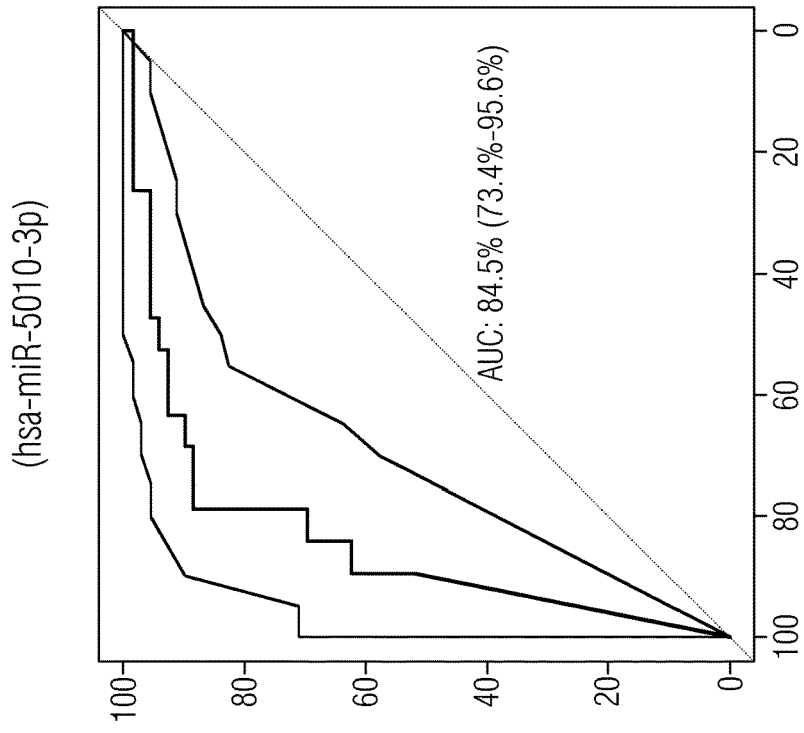
FIG. 8 shows the ROC curve for the best single miRNAs from the validation study, gene expression data obtained by qRT-PCR. X-axis: specificity, y-axis: sensitivity.

Besides single markers, combinations of multiple markers have demonstrated a potential to improve the diagnostic accuracy. To test this hypothesis, a standard machine learning approach was applied. In a cross-validation loop, the markers with lowest significance values were stepwise added and repeatedly radial basis function support vector machines were carried out. The accuracy, specificity and sensitivity depend on the number of biomarkers are presented in FIG. 4. As shown there, accuracy, specificity and sensitivity increase up to a signature number of 250 miRNAs and then converge to 90%. However, this set of miRNAs contains a significant amount of redundant biomarkers, i.e., markers that have almost identical information content to each other and are highly correlated such that even significantly smaller sets of markers can be expected to perform highly accurate distinction in Alzheimer samples and controls. We selected a signature of just 7 markers, namely the up-regulated miRNAs brain-mir-112, brain-mir-161, hsa-let-7d-3p and hsa-miR-5010-3p as well as the down-regulated markers hsa-miR-103a-3p, hsa-miR-107 and hsa-miR-532-5p. To combine the values of the 7 miRNAs in one score we calculated the average z-score as detailed in the Material & Methods section. While we reached averaged values of 0.087 and standard deviation of 0.72 for the controls and average values of 0.22 and standard deviation of 0.74 for the MCI patients, AD patients reached a much higher score of 0.63 at a standard deviation of 0.64. Thus, the Alzheimer patients have significantly higher scores as controls, indicated by the two-tailed t-test p-value of 0.025. These numbers are detailed as bar-chart in FIG. 5. The ROC curve for the signature showing an AUC of 84.3% with 95% CI of 75.3%-93.2% is presented in FIG. 6.

A further signature of 12 markers with limited cross-correlation was selected, including the most strongly dys-regulated markers that are less frequently dys-regulated in other diseases and show a potential to separate AD also from MCI. More precisely, this selected signature contains the up-regulated miRNAs brain-mir-112, brain-mir-161, hsa-let-7d-3p, hsa-miR-5010-3p, hsa-miR-26b-3p, hsa-miR-26a-5p, hsa-miR-1285-5p, and hsa-miR-151a-3p as well as the down-regulated markers hsa-miR-103a-3p, hsa-miR-107, hsa-miR-532-5p, and hsa-let-7f-5p. To combine the values of the 12 miRNAs in one score the combined score was computed as discussed above. While averaged values of 0 and standard deviation of 0.39 for the controls were reached and average values of 0.32 and standard deviation of 0.5 for the MCI patients were reached, AD patients reached a much higher score of 0.93 at a standard deviation of 0.54. Thus, the Alzheimer patients have significantly higher scores as controls, indicated by the two-tailed t-test p-value of $3.7*10^{-11}$ in case of AD versus C as well as $6*10^{-5}$ in case of AD versus MCI. In addition we computed the same scores for a set of 15 MS samples, showing a likewise decreased score of 0.1 at standard deviation of 0.34.

Biological Relevance of miRNAs for AD

To understand the biological function of the dys-regulated miRNAs better a miRNA enrichment analysis for the up- and down-regulated miRNAs was applied (Ming Lu, Bing Shi, Juan Wang, Qun Cao and Qinghua Cui. TAM: A method for enrichment and depletion analysis of a microRNA category in a list of microRNAs. BMC Bioinformatics 2010, 11:419 (9 Aug. 2010). The results of this analysis are detailed in Table 2. Altogether, for the 55 down-regulated miRNAs 11 significant categories after adjustment for multiple testing were detected while for the 115 up-regulated just a single category remained significant, the miR-30 family with 5 members being up-regulated. In contrast, for the down-regulated miRNAs 7 miRNAs of the let-7 family were found being significant. In addition, the set contained also 8 miRNAs belonging to anti-cell proliferation and 13 tumor suppressors. Finally, we were able to show that the down-regulated miRNAs correlate to 8 diseases, including Alzheimer. Here, we found 5 miRNAs being relevant, including hsa-miR-17, hsa-miR-29a, hsa-miR-29b, hsa-miR-106b and hsa-miR-107.

TABLE 2

Regulated Pathways and categories

| Term | down Count | down p-value | up Count | up p-value |
|---|---|---|---|---|
| anti-cell proliferation | 8 | 4.60-3 | n.s. | n.s. |
| miRNA tumor suppressors | 13 | 6.71-3 | n.s. | n.s. |
| let-7 family | 7 | 7.00-3 | n.s. | n.s. |
| Digestive System Neoplasms | 6 | 0.0144 | n.s. | n.s. |
| Pituitary Neoplasms | 7 | 0.0168 | n.s. | n.s. |
| Lymphoma, Primary Effusion | 7 | 0.0201 | n.s. | n.s. |
| Sarcoma, Kaposi | 7 | 0.021 | n.s. | n.s. |
| Carcinoma, Non-Small Cell Lung | 6 | 0.027 | n.s. | n.s. |
| Neoplasms | 14 | 0.028 | n.s. | n.s. |
| Colonic Neoplasms | 12 | 0.0388 | n.s. | n.s. |
| Alzheimer Disease | 5 | 0.0433 | n.s. | n.s. |
| mir-30 family | n.s. | n.s. | 5 | 8.95-3 |

Validation of Signature by q-RT-PCR

In order to transfer the signature to clinical routine settings it is essential that the proposed in-vitro diagnostic test can be applied in molecular diagnostic labs in reasonable time using standard equipment. To this end, qRT-PCR represents a suitable solution to replicate and validate our AD signature using this approach. In addition to measure just controls, AD and MCI patients, a wide range of other neurological disorders were also included. For AD, besides the US cohort also a set of samples collected in Germany were included. The full overview on measured samples is provided in Table 1.

First, the fold quotients of the initial screening cohort were compared and analyzed by next-generation sequencing and this was compared to the performance of the same miRNAs by qRT-PCR. As the scatter-plot in FIG. 7 presents, all miRNAs have been dys-regulated in the same direction by both approaches and in both cohorts, indicating a very high degree of concordance between screening and valida-tion study. As for the next generation sequencing screening approach AUC values were calculated for the validation qRT-PCR cohort. The best single miRNA was miR-5010-3p with an AUC of 84.5% (AUC of screening: 75.5%). On average, the 7 miRNAs reached an AUC value of 71%, indicating the high diagnostic information content. Next, the question was addressed whether the combination of the 7 miRNAs can further improve the diagnosis of AD. The same z-scored based approach was applied.

While averaged values of 0.087 and standard deviation of 0.72 for the controls and average values of 0.22 and standard deviation of 0.74 were reached for the MCI patients, AD patients reached a much higher score of 0.63 at a standard deviation of 0.64.

Figure 10:
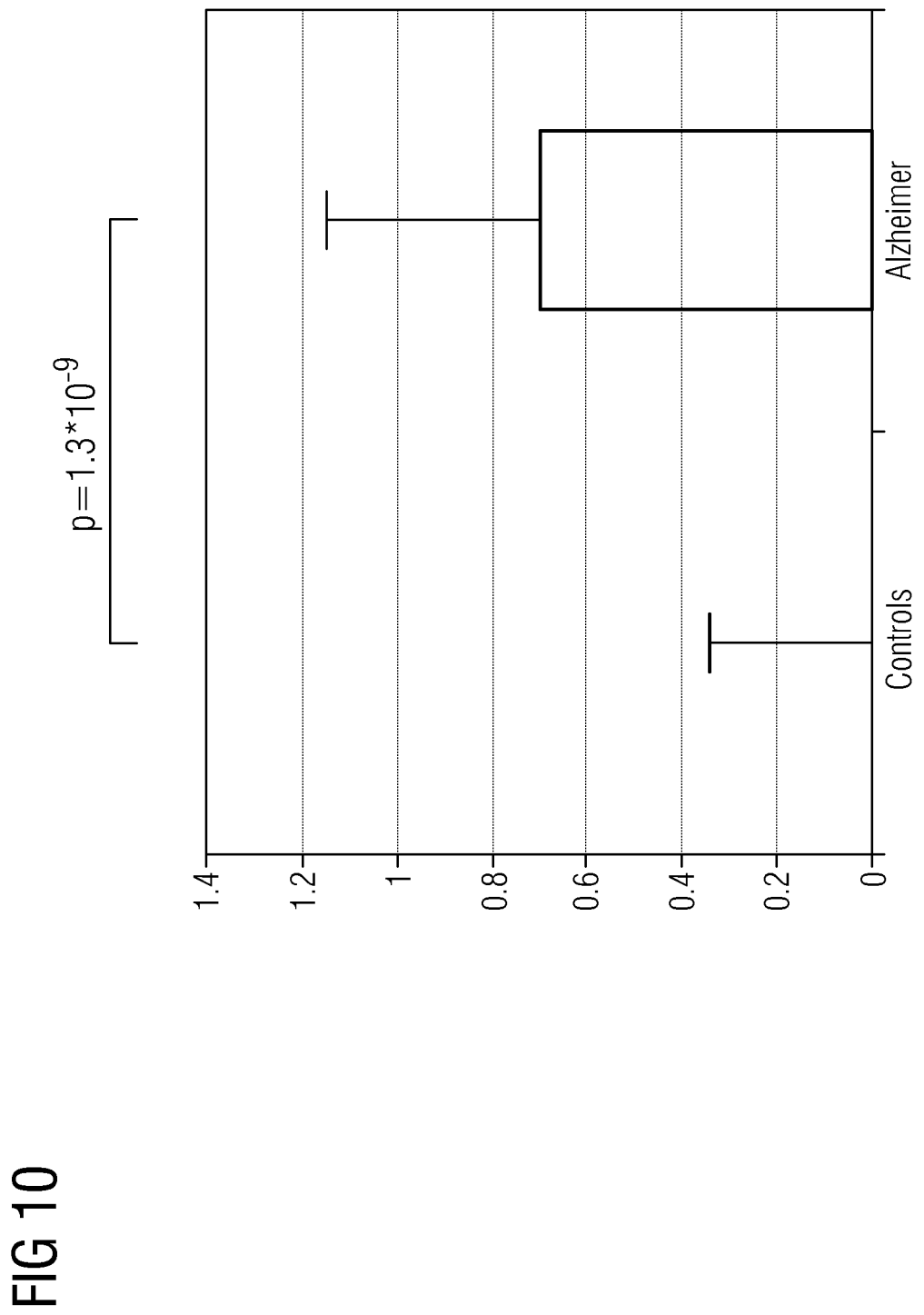
FIG. 10 shows the improved combined score of controls (left column) vs. AD patients (right column).

For controls an average value of 0 (screening: −0.087) at a standard deviation of 0.34 (screening: 0.72) was obtained, while for AD patients, the score was as high as 0.7 (screening 0.63) at standard deviation of 0.45 (screening: 0.64). Thus, AD patients have significantly higher values as compared to controls since the 2-tailed t-test p-value is as low as 1.3*10-9 (screening 0.025). The z-scores are presented as bar-diagram in FIG. 10. Here, it can be clearly seen that especially the standard deviations are much smaller for the qRT-PCR based validation cohort.

Scores of Other Neurological Disorders

Figure 11:
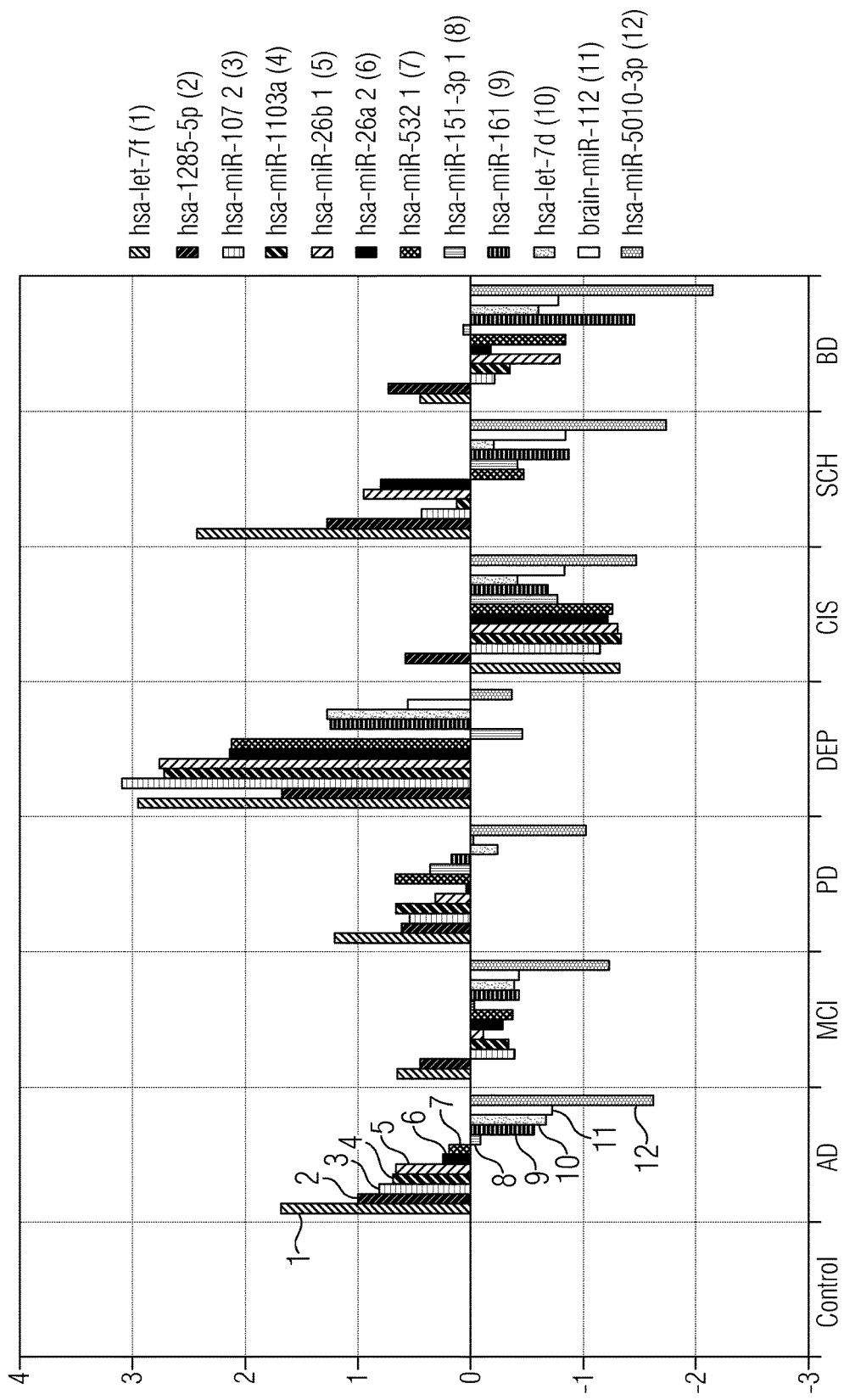
FIG. 11 shows the validation of 12 miRNAs in 7 diseases (AD, MCI, PD, DEP, CIS, SCH, and BD and controls). The 12 miRNAs are (denoted by columns 1-12, respectively) hsa-let-7f-5p, hsa-miR-1285-5p, hsa-miR-107, hsa-miR-103a-3p, hsa-miR-26b-3p, hsa-miR-26a-5p, hsa-miR-532-5p, hsa-miR-151a-3p, brain-mir-161, hsa-let-7d-3p, brain-mir-112, and hsa-miR-5010-3p.
Figure 12:
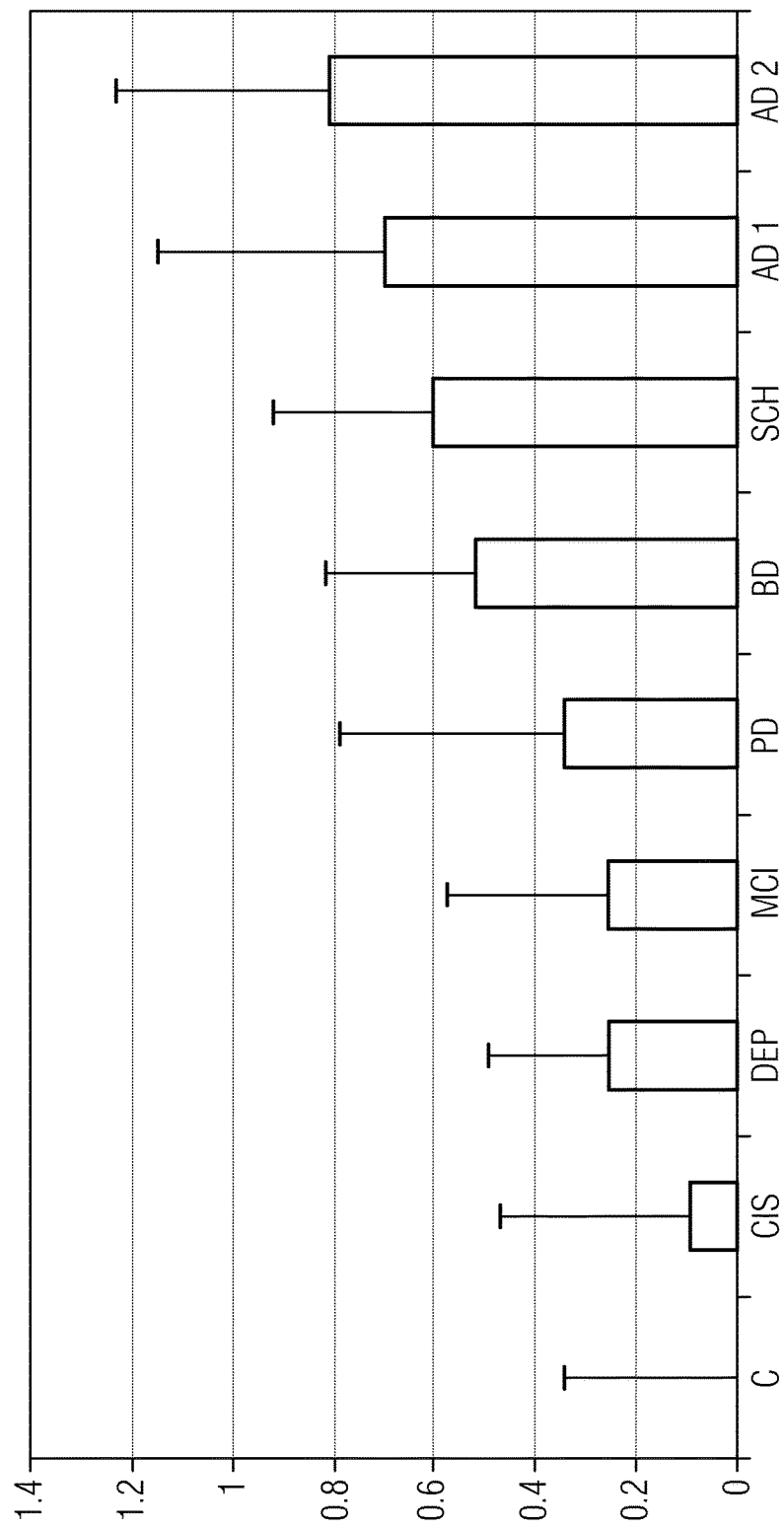
FIG. 12 shows the combined score of the 7-miRNA signature brain-mir-112, hsa-miR-5010-3p, hsa-miR-103a-3p, hsa-miR-107, hsa-let-7d-3p, hsa-miR-532-5p, and brain-mir-161 for all diseases. The combined score (y-axis) was obtained using quantitative RT PCR.
Figure 13:
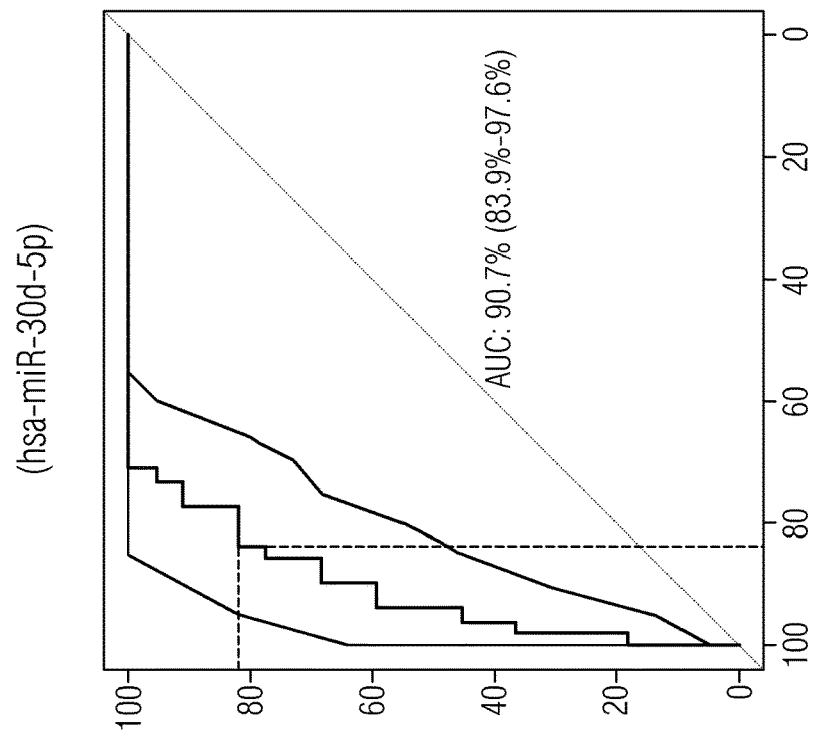
FIG. 13 shows a combined score of AD, MCI and controls for the 12-marker signature hsa-let-7f-5p, hsa-miR-1285-5p, hsa-miR-107, hsa-miR-103a-3p, hsa-miR-26b-3p, hsa-miR-26a-5p, hsa-miR-532-5p, hsa-miR-151a-3p, brain-mir-161, hsa-let-7d-3p, brain-mir-112, and hsa-miR-5010-3p. The combined score (y-axis) was obtained using high throughput sequencing.
Figure 14:
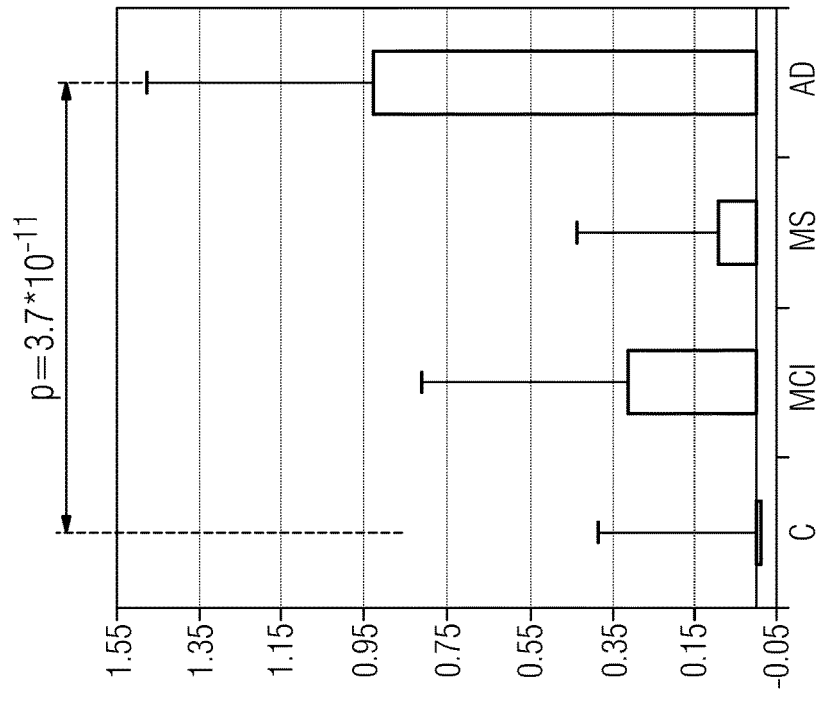
FIG. 14 shows the ROC curve for the 12-marker signature of FIG. 13, gene expression data obtained by NGS. X-axis: specificity, y-axis: sensitivity.
Figure 15:
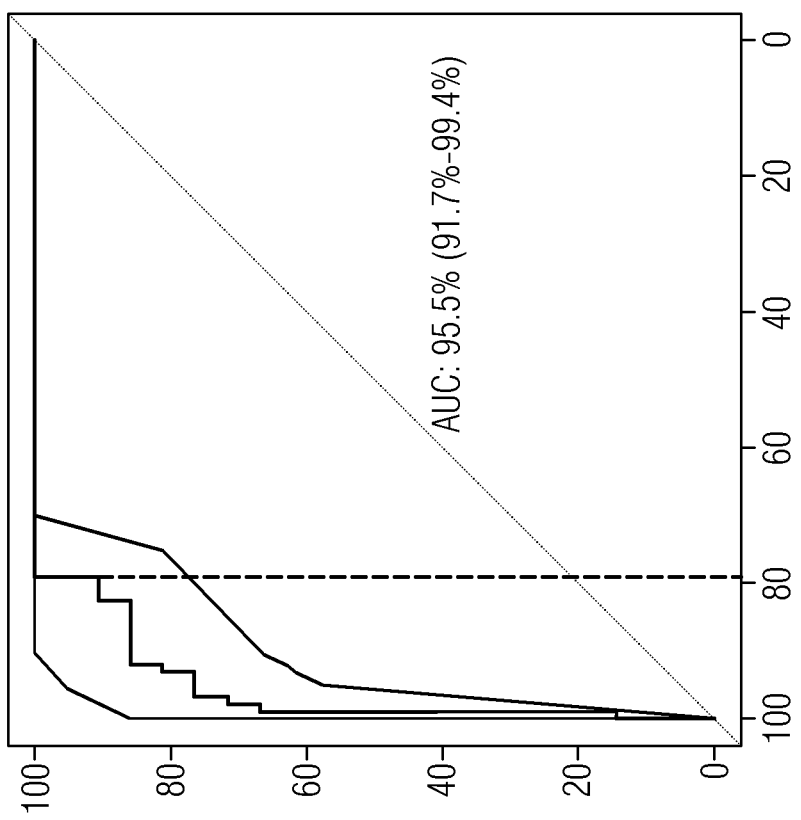
FIG. 15 shows the ROC curve for the 12-marker signature of FIG. 13, gene expression data obtained by qRT-PCR. X-axis: specificity, y-axis: sensitivity.
Figure 16:
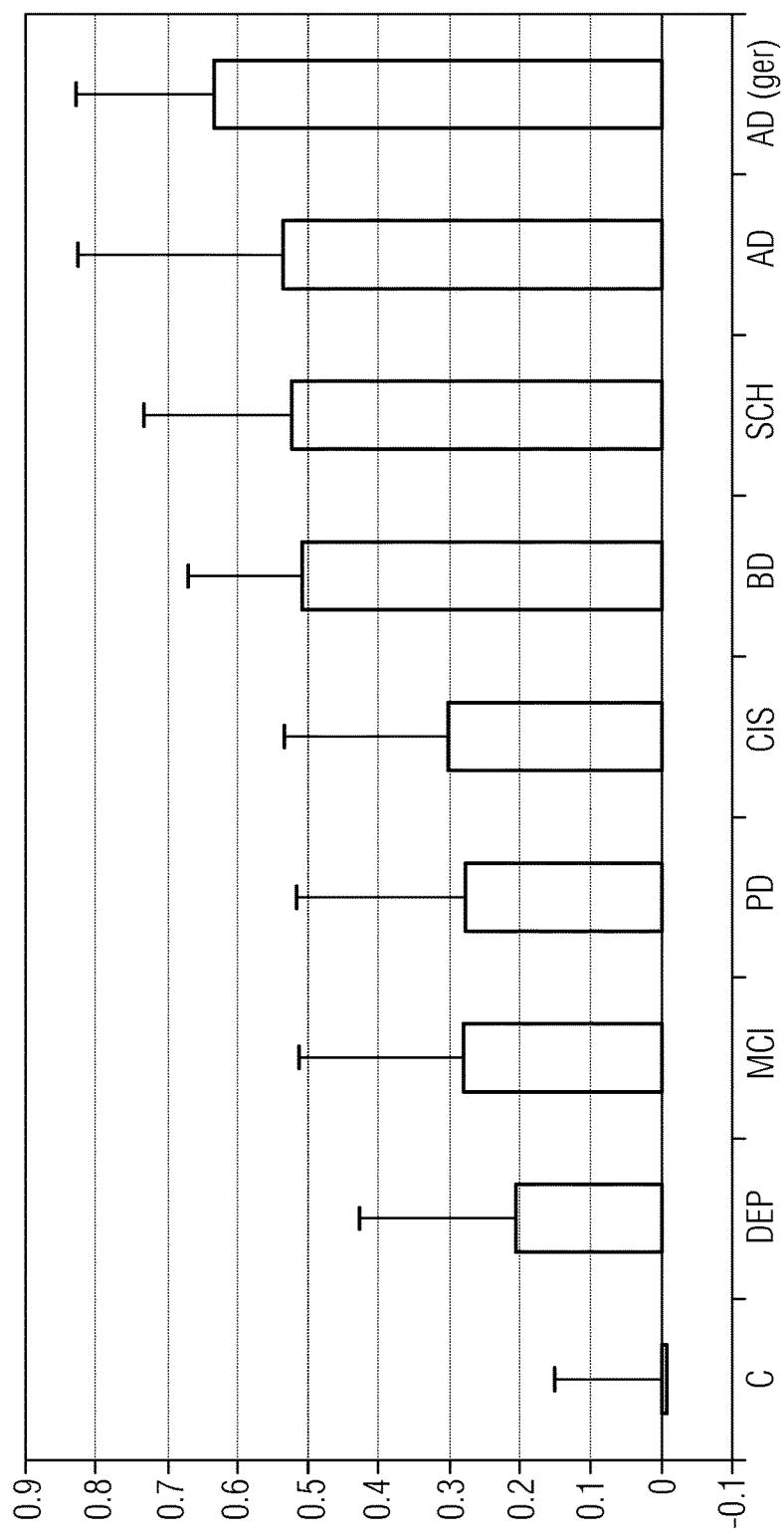
FIG. 16 shows the combined score of the 12-miRNA signature hsa-let-7f-5p, hsa-miR-1285-5p, hsa-miR-107, hsa-miR-103a-3p, hsa-miR-26b-3p, hsa-miR-26a-5p, hsa-miR-532-5p, hsa-miR-151a-3p, brain-mir-161, hsa-let-7d-3p, brain-mir-112, and hsa-miR-5010-3p for all diseases. The combined score (y-axis) was obtained using quantitative RT PCR.

Next the question was asked whether a cohort of other neurological disorders shows likewise significant deviations to controls. As detailed in Table 1 we measured a second cohort of Alzheimer patients, Parkinson disease, mild cognitive impairment, schizophrenia, bipolar disorder, multiple sclerosis (CIS) depression patients for the signature of 7 miRNAs. In FIG. 11, the bar diagrams for all diseases and all miRNAs are present. Here, the Alzheimer patients score is set to 0, as described earlier we have four down- and three up-regulated miRNAs for the controls. For mild cognitive impairment patients the same four miRNAs were down- and the same three miRNAs were up-regulated, providing strong evidence that the MCI signature is much closer to controls as compared to AD. For CIS patients only two miRNAs were down-regulated, while the third one was not dys-regulated and the remaining three were strongly up-regulated. For Parkinson disease, the first 5 miRNAs were down-while the remaining two were strongly up-regulated. For Schizophrenia and Bipolar Disease, almost all miRNAs were strongly up-regulated, in contrast, for Depression all miRNAs were significantly down-regulated. In summary, the results promise that AD can not only be distinguished from controls but also very well from other neurological disorders. Of course the same z-score based approach can be applied as for the Alzheimer and control patients in order to get an overall score for each cohort.

Further significant signatures of miRNA for differentiating between AD and controls have been found:
hsa-miR-1285-5p brain-mir-112 hsa-miR-5010-3p hsa-miR-151a-3p hsa-let-7f-5p,
hsa-miR-3127-3p hsa-miR-1285-5p hsa-miR-425-5p hsa-miR-148b-5p hsa-miR-144-5p,
hsa-miR-3127-3p hsa-miR-3157-3p hsa-miR-148b-5p hsa-miR-151a-3p hsa-miR-144-5p,
hsa-miR-3127-3p hsa-miR-1285-5p hsa-miR-425-5p hsa-miR-151a-3p hsa-miR-144-5p,
hsa-miR-1285-5p brain-mir-112 hsa-miR-5010-3p hsa-miR-151a-3p hsa-let-7a-5p,
hsa-miR-5001-3p hsa-miR-1285-5p hsa-miR-425-5p hsa-miR-148b-5p hsa-miR-144-5p,
hsa-miR-3127-3p hsa-miR-1285-5p hsa-miR-148b-5p hsa-miR-151a-3p hsa-miR-144-5p, hsa-miR-1285-5p hsa-miR-5010-3p hsa-miR-425-5p hsa-miR-148b-5p hsa-miR-144-5p, hsa-miR-1285-5p hsa-miR-5010-3p hsa-miR-151a-3p hsa-miR-144-5p hsa-let-7a-5p, hsa-miR-1285-5p brain-mir-112 hsa-miR-425-5p hsa-miR-151a-3p hsa-miR-144-5p, hsa-miR-5001-3p hsa-miR-1285-5p brain-mir-112 hsa-miR-151a-3p hsa-let-7f-5p, hsa-miR-1285-5p hsa-miR-5010-3p hsa-miR-148b-5p hsa-miR-144-5p hsa-let-7f-5p, hsa-miR-1285-5p hsa-miR-3157-3p hsa-miR-148b-5p hsa-miR-151a-3p hsa-miR-144-5p, hsa-miR-5001-3p hsa-miR-1285-5p hsa-miR-5010-3p hsa-miR-151a-3p hsa-let-7f-5p, brain-mir-431 hsa-miR-1285-5p hsa-miR-3157-3p hsa-miR-151a-3p hsa-miR-144-5p, hsa-miR-3127-3p hsa-miR-1285-5p brain-mir-112 hsa-miR-425-5p hsa-miR-151a-3p, hsa-miR-1285-5p hsa-miR-5010-3p hsa-miR-151a-3p hsa-miR-144-5p hsa-let-7f-5p, hsa-miR-550a-5p hsa-miR-1285-5p brain-mir-112 hsa-miR-151a-3p hsa-let-7f-5p, hsa-miR-1285-5p brain-mir-112 hsa-miR-148b-5p hsa-miR-151a-3p hsa-miR-144-5p, and hsa-miR-5001-3p brain-mir-112 hsa-miR-5010-3p hsa-miR-151a-3p hsa-let-7f-5p.

These are further preferred combinations for classifying a sample of a patient suffering from or at risk of developing Alzheimer's Disease or diagnosing AD, or predicting an outcome of AD (ca. Table 3)

TABLE 3

Further preferred signatures for diagnosing AD.

| Signature | AUC | Mean AD | mean Control | mean MCI | mean AD replication | miRNA 1 | miRNA 2 | miRNA 3 | miRNA 4 | miRNA 5 |
|---|---|---|---|---|---|---|---|---|---|---|
| sig #1 | 0.011 | 1.123 | −0.019 | 0.557 | 1.190 | hsa-miR-1285-5p | brain-mir-112 | hsa-miR-5010-3p | hsa-miR-151a-3p | hsa-let-7f-5p |
| sig #2 | 0.011 | 1.054 | −0.012 | 0.549 | 1.281 | hsa-miR-3127-3p | hsa-miR-1285-5p | hsa-miR-425-5p | hsa-miR-148b-5p | hsa-miR-144-5p |
| sig #3 | 0.015 | 1.101 | −0.028 | 0.454 | 1.137 | hsa-miR-3127-3p | hsa-miR-3157-3p | hsa-miR-148b-5p | hsa-miR-151a-3p | hsa-miR-144-5p |
| sig #4 | 0.015 | 1.097 | −0.015 | 0.663 | 1.325 | hsa-miR-3127-3p | hsa-miR-1285-5p | hsa-miR-425-5p | hsa-miR-151a-3p | hsa-miR-144-5p |
| sig #5 | 0.016 | 1.111 | −0.020 | 0.561 | 1.187 | hsa-miR-1285-5p | brain-mir-112 | hsa-miR-5010-3p | hsa-miR-151a-3p | hsa-let-7a-5p |
| sig #6 | 0.018 | 1.078 | 0.003 | 0.515 | 1.318 | hsa-miR-5001-3p | hsa-miR-1285-5p | hsa-miR-425-5p | hsa-miR-148b-5p | hsa-miR-144-5p |
| sig #7 | 0.020 | 1.097 | −0.015 | 0.490 | 1.140 | hsa-miR-3127-3p | hsa-miR-1285-5p | hsa-miR-148b-5p | hsa-miR-151a-3p | hsa-miR-144-5p |
| sig #8 | 0.020 | 1.062 | −0.010 | 0.493 | 1.299 | hsa-miR-1285-5p | hsa-miR-5010-3p | hsa-miR-425-5p | hsa-miR-148b-5p | hsa-miR-144-5p |
| sig #9 | 0.021 | 1.152 | 0.002 | 0.645 | 1.332 | hsa-miR-1285-5p | hsa-miR-5010-3p | hsa-miR-151a-3p | hsa-miR-144-5p | hsa-let-7a-5p |
| sig #10 | 0.021 | 1.139 | −0.014 | 0.614 | 1.217 | hsa-miR-1285-5p | brain-mir-112 | hsa-miR-425-5p | hsa-miR-151a-3p | hsa-miR-144-5p |
| sig #11 | 0.021 | 1.139 | −0.006 | 0.579 | 1.209 | hsa-miR-5001-3p | hsa-miR-1285-5p | brain-mir-112 | hsa-miR-151a-3p | hsa-let-7f-5p |
| sig #12 | 0.021 | 1.120 | 0.006 | 0.527 | 1.291 | hsa-miR-1285-5p | hsa-miR-5010-3p | hsa-miR-148b-5p | hsa-miR-144-5p | hsa-let-7f-5p |
| sig #13 | 0.021 | 1.111 | −0.015 | 0.400 | 1.031 | hsa-miR-1285-5p | hsa-miR-3157-3p | hsa-miR-148b-5p | hsa-miR-151a-3p | hsa-miR-144-5p |
| sig #14 | 0.021 | 1.105 | −0.004 | 0.572 | 1.335 | hsa-miR-5001-3p | hsa-miR-1285-5p | hsa-miR-5010-3p | hsa-miR-151a-3p | hsa-let-7f-5p |
| sig #15 | 0.021 | 1.098 | −0.021 | 0.492 | 0.767 | brain-mir-431 | hsa-miR-1285-5p | hsa-miR-3157-3p | hsa-miR-151a-3p | hsa-miR-144-5p |
| sig #16 | 0.021 | 1.056 | −0.038 | 0.579 | 1.180 | hsa-miR-3127-3p | hsa-miR-1285-5p | brain-mir-112 | hsa-miR-425-5p | hsa-miR-151a-3p |
| sig #17 | 0.022 | 1.164 | 0.003 | 0.641 | 1.335 | hsa-miR-1285-5p | hsa-miR-5010-3p | hsa-miR-151a-3p | hsa-miR-144-5p | hsa-let-7f-5p |
| sig #18 | 0.022 | 1.140 | −0.015 | 0.691 | 0.649 | hsa-miR-550a-5p | hsa-miR-1285-5p | brain-mir-112 | hsa-miR-151a-3p | hsa-let-7f-5p |
| sig #19 | 0.022 | 1.140 | −0.014 | 0.441 | 1.033 | hsa-miR-1285-5p | brain-mir-112 | hsa-miR-148b-5p | hsa-miR-151a-3p | hsa-miR-144-5p |
| sig #20 | 0.022 | 1.137 | −0.016 | 0.576 | 1.333 | hsa-miR-5001-3p | brain-mir-112 | hsa-miR-5010-3p | hsa-miR-151a-3p | hsa-let-7f-5p |

SUPPLEMENTAL TABLE 1 a

Significantly down-regulated miRNAs in AD vs. controls.

| SEQ ID NO | miRNA | median AD | median Control | t-test p-value single | AUC |
|---|---|---|---|---|---|
| 1 | hsa-miR-144-5p | 179.3082706767 | 913.7744360902 | 8.76E−08 | 0.0928030303 |
| 2 | hsa-let-7f-5p | 8334.1804511278 | 12867.954887218 | 7.60E−07 | 0.0710227273 |
| 3 | hsa-let-7e-5p | 4971.7669172932 | 8212.9360902256 | 8.58E−07 | 0.1382575758 |
| 4 | hsa-let-7a-5p | 8868.4511278196 | 15370.052631579 | 4.43E−06 | 0.0880681818 |
| 5 | hsa-miR-107 | 2433.0413533835 | 4822.3984962406 | 1.82E−05 | 0.203125 |
| 6 | hsa-let-7g-5p | 1352.3684210526 | 3403.3759398496 | 2.69E−05 | 0.1259469697 |
| 7 | hsa-miR-103a-3p | 2810.8458646617 | 5290.1278195489 | 3.89E−05 | 0.2088068182 |
| 8 | hsa-miR-98 | 106.0864661654 | 217.3533834586 | 4.28E−05 | 0.1515151515 |
| 9 | hsa-miR-29c-3p | 40.8327067669 | 74.8402255639 | 6.87E−05 | 0.1922348485 |
| 10 | hsa-miR-101-3p | 56.1090225564 | 417.7105263158 | 0.0001143344 | 0.1463068182 |
| 11 | hsa-miR-548h-5p | 3.6296992481 | 10.0845864662 | 0.000139166 | 0.1770833333 |
| 12 | hsa-miR-106b-3p | 1685.5864661654 | 2614.7518796993 | 0.0001453506 | 0.2097537879 |
| 13 | hsa-miR-15a-5p | 598.484962406 | 1472.9962406015 | 0.0001554169 | 0.1557765152 |
| 14 | hsa-miR-548g-5p | 3.0338345865 | 9.6296992481 | 0.0002158917 | 0.1979166667 |
| 15 | hsa-miR-548ar-5p | 3.0338345865 | 9.6296992481 | 0.0002158917 | 0.1979166667 |
| 16 | hsa-miR-548x-5p | 3.0338345865 | 9.6296992481 | 0.0002158917 | 0.1979166667 |
| 17 | hsa-miR-548aj-5p | 3.0338345865 | 9.6296992481 | 0.0002158917 | 0.1979166667 |
| 18 | hsa-let-7c | 6147.5714285714 | 11249.522556391 | 0.0002796738 | 0.1661931818 |
| 19 | brain-mir-394 | 2.8026315789 | 7.8364661654 | 0.0003164566 | 0.2059659091 |
| 20 | hsa-miR-1294 | 8.765037594 | 25.9379699248 | 0.0003239282 | 0.2026515152 |
| 21 | brain-mir-170 | 2.8026315789 | 7.8364661654 | 0.0003241053 | 0.2069128788 |
| 22 | hsa-miR-199a-3p | 4.0883458647 | 12.454887218 | 0.0003438893 | 0.1595643939 |
| 23 | brain-mir-149 | 2.8157894737 | 7.8364661654 | 0.000344696 | 0.2097537879 |
| 24 | brain-mir-151 | 2.8157894737 | 7.8364661654 | 0.000344696 | 0.2097537879 |
| 25 | brain-mir-370 | 178.4586466165 | 778.2894736842 | 0.0003625216 | 0.1553030303 |
| 26 | hsa-miR-199b-3p | 4.0883458647 | 12.6259398496 | 0.0003732986 | 0.1652462121 |
| 27 | brain-mir-333 | 2.8026315789 | 7.8364661654 | 0.0004122695 | 0.2069128788 |
| 28 | hsa-miR-628-3p | 2.954887218 | 7.1165413534 | 0.0004263003 | 0.2320075758 |
| 29 | hsa-miR-190a | 1.0488721805 | 5.5977443609 | 0.0004511324 | 0.1837121212 |
| 30 | hsa-miR-29b-3p | 11.8120300752 | 23.6503759398 | 0.0005076275 | 0.228219697 |
| 31 | hsa-miR-660-5p | 20.2537593985 | 72.9116541353 | 0.0006111848 | 0.1766098485 |
| 32 | hsa-miR-143-3p | 81.0676691729 | 168.0714285714 | 0.0006300042 | 0.2277462121 |
| 33 | hsa-miR-548av-5p | 3.2593984962 | 9.6541353383 | 0.0006819514 | 0.2196969697 |
| 34 | hsa-miR-548k | 3.2593984962 | 9.6541353383 | 0.0006819514 | 0.2196969697 |
| 35 | hsa-miR-29a-3p | 43.6917293233 | 74.4943609023 | 0.0008592211 | 0.2414772727 |
| 36 | hsa-miR-548i | 0.1992481203 | 1.1090225564 | 0.0009595931 | 0.1482007576 |
| 37 | hsa-miR-17-3p | 32.5563909774 | 80.7781954887 | 0.0015924698 | 0.1410984848 |
| 38 | brain-mir-398 | 10.0338345865 | 29.5526315789 | 0.0016819805 | 0.1964962121 |
| 39 | hsa-miR-148a-3p | 274.1748120301 | 845.5263157895 | 0.001762298 | 0.1586174242 |
| 40 | hsa-miR-126-3p | 39.045112782 | 108.8195488722 | 0.0028031688 | 0.2135416667 |
| 41 | brain-mir-150 | 6.4266917293 | 19.4812030075 | 0.0034501841 | 0.2201704545 |
| 42 | hsa-let-7i-5p | 2907.4210526316 | 6027.2030075188 | 0.0034616244 | 0.2059659091 |
| 43 | hsa-miR-33b-5p | 0.227443609 | 2.1240601504 | 0.0035364268 | 0.2580492424 |
| 44 | hsa-miR-3200-3p | 16.765037594 | 23.5037593985 | 0.0045456431 | 0.3233901515 |
| 45 | hsa-miR-548o-5p | 0.3834586466 | 1.7593984962 | 0.0047156877 | 0.2831439394 |
| 46 | hsa-miR-152 | 11.2142857143 | 22.2312030075 | 0.0052379113 | 0.1983901515 |
| 47 | hsa-miR-548am-5p | 0.4887218045 | 1.7593984962 | 0.0053080221 | 0.2878787879 |
| 48 | hsa-miR-548au-5p | 0.4887218045 | 1.7593984962 | 0.0053080221 | 0.2878787879 |
| 49 | hsa-miR-548c-5p | 0.4887218045 | 1.7593984962 | 0.0053080221 | 0.2878787879 |
| 50 | brain-mir-248S | 0.2443609023 | 0.9285714286 | 0.0065438684 | 0.2547348485 |
| 51 | hsa-miR-215 | 2042.3909774436 | 2997.969924812 | 0.008661199 | 0.3072916667 |
| 52 | hsa-miR-340-5p | 7.5977443609 | 21.984962406 | 0.0088183152 | 0.271780303 |
| 53 | hsa-miR-1301 | 6.7330827068 | 9.5488721805 | 0.0089721175 | 0.2845643939 |
| 54 | brain-mir-145 | 13.9511278195 | 17.7556390977 | 0.008979579 | 0.3143939394 |
| 55 | hsa-miR-504 | 0.3834586466 | 1.8026315789 | 0.0093874443 | 0.3697916667 |

SUPPLEMENTAL TABLE 1 b

Significantly up-regulated miRNAs in AD vs. controls.

| SEQ ID NO | miRNA | median AD | median Control | t-test p-value single | AUC |
|---|---|---|---|---|---|
| 56 | hsa-miR-30d-5p | 11759.6691729323 | 7038.4962406015 | 9.25E−12 | 0.8863636364 |
| 57 | hsa-miR-4781-3p | 20.1597744361 | 10.0714285714 | 8.76E−10 | 0.8726325758 |
| 58 | hsa-miR-151a-3p | 3303.037593985 | 1892.6616541353 | 3.49E−08 | 0.8645833333 |
| 59 | brain-mir-112 | 10.242481203 | 3.2687969925 | 4.77E−08 | 0.8735795455 |
| 60 | hsa-miR-28-3p | 1009.6466165414 | 537.7894736842 | 1.17E−07 | 0.7845643939 |
| 61 | hsa-miR-26b-3p | 73.6240601504 | 29.2105263158 | 1.18E−07 | 0.8333333333 |
| 62 | hsa-miR-1468 | 80.1296992481 | 34.6466165414 | 9.00E−07 | 0.7732007576 |
| 63 | hsa-miR-128 | 1204.3533834587 | 761.5676691729 | 9.93E−07 | 0.8238636364 |
| 64 | hsa-miR-550a-5p | 61.6052631579 | 39.4135338346 | 1.93E−06 | 0.8143939394 |
| 65 | hsa-miR-5010-3p | 134.5263157895 | 77.8684210526 | 2.52E−06 | 0.8191287879 |
| 66 | hsa-miR-148b-5p | 24.1278195489 | 12.8928571429 | 2.85E−06 | 0.8096590909 |
| 67 | brain-mir-395 | 7.8759398496 | 4.3233082707 | 3.18E−06 | 0.7935606061 |
| 68 | brain-mir-308 | 7.8759398496 | 4.3233082707 | 3.18E−06 | 0.7935606061 |
| 69 | hsa-miR-1285-5p | 7.0695488722 | 3.2030075188 | 3.47E−06 | 0.7954545455 |
| 70 | hsa-miR-5001-3p | 14.8796992481 | 7.0714285714 | 4.41E−06 | 0.8077651515 |
| 71 | hsa-miR-3127-3p | 5.8421052632 | 2.4718045113 | 5.13E−06 | 0.7883522727 |
| 72 | hsa-miR-3157-3p | 7.3778195489 | 3.1616541353 | 7.70E−06 | 0.8181818182 |
| 73 | brain-mir-431 | 6.2462406015 | 2.9436090226 | 8.30E−06 | 0.7869318182 |
| 74 | hsa-miR-550a-3-5p | 53.4661654135 | 31.9680451128 | 8.51E−06 | 0.7987689394 |
| 75 | hsa-miR-361-5p | 51.6973684211 | 28.5733082707 | 1.18E−05 | 0.7940340909 |
| 76 | brain-mir-83 | 160.5808270677 | 95.3872180451 | 1.37E−05 | 0.7367424242 |
| 77 | hsa-miR-589-5p | 305.6390977444 | 227.015037594 | 1.54E−05 | 0.7698863636 |
| 78 | hsa-miR-425-5p | 5290.1278195489 | 2907.4210526316 | 1.61E−05 | 0.8020833333 |
| 79 | hsa-miR-30a-5p | 10739.3759398496 | 7557.4210526316 | 2.66E−05 | 0.7826704545 |
| 80 | brain-mir-79 | 3.5206766917 | 1.3026315789 | 2.85E−05 | 0.7552083333 |
| 81 | brain-mir-80 | 3.5206766917 | 1.3026315789 | 2.85E−05 | 0.7552083333 |
| 82 | hsa-miR-330-5p | 10.7312030075 | 6.3402255639 | 3.46E−05 | 0.7722537879 |
| 83 | hsa-miR-186-5p | 4206.2932330827 | 2433.0413533835 | 3.46E−05 | 0.775094697 |
| 84 | brain-mir-390 | 5.4191729323 | 3.1428571429 | 3.85E−05 | 0.7618371212 |
| 85 | hsa-let-7d-3p | 391.4060150376 | 208.9398496241 | 3.95E−05 | 0.7069128788 |
| 86 | hsa-miR-328 | 396.6992481203 | 204.6898496241 | 4.08E−05 | 0.7168560606 |
| 87 | hsa-miR-30c-5p | 3195.7781954887 | 1563.7631578947 | 4.79E−05 | 0.7769886364 |
| 88 | brain-mir-200 | 30.3740601504 | 15.8233082707 | 5.41E−05 | 0.7665719697 |
| 89 | hsa-miR-363-3p | 6371.4285714286 | 4971.7669172932 | 5.51E−05 | 0.7552083333 |
| 90 | hsa-miR-339-3p | 125.3120300752 | 87.8345864662 | 5.67E−05 | 0.7471590909 |
| 91 | brain-mir-114 | 1009.6466165414 | 543.5526315789 | 5.76E−05 | 0.6856060606 |
| 92 | hsa-miR-942 | 512.7142857143 | 306.2894736842 | 6.12E−05 | 0.6851325758 |
| 93 | hsa-miR-345-5p | 470.6090225564 | 317.9210526316 | 6.17E−05 | 0.7481060606 |
| 94 | brain-mir-247 | 2997.969924812 | 1634.6879699248 | 7.23E−05 | 0.7315340909 |
| 95 | hsa-miR-4742-3p | 43.2030075188 | 27.6635338346 | 7.99E−05 | 0.7201704545 |
| 96 | brain-mir-314 | 3614.8045112782 | 2124.5751879699 | 8.13E−05 | 0.7324810606 |
| 97 | brain-mir-12 | 2433.0413533835 | 1370.5338345865 | 9.13E−05 | 0.7220643939 |
| 98 | brain-mir-232 | 75.0733082707 | 39.9285714286 | 9.70E−05 | 0.6799242424 |
| 99 | brain-mir-424S | 4.8571428571 | 2.1503759398 | 0.0001134253 | 0.7608901515 |
| 100 | brain-mir-219 | 28.5751879699 | 15.7819548872 | 0.0001441433 | 0.7736742424 |
| 101 | hsa-miR-10a-5p | 827.0977443609 | 443.9586466165 | 0.0001696328 | 0.7334280303 |
| 102 | hsa-miR-3605-3p | 280.9135338346 | 187.6466165414 | 0.0001817728 | 0.6837121212 |
| 103 | brain-mir-52 | 9.2406015038 | 4.6503759398 | 0.0002065404 | 0.7817234848 |
| 104 | brain-mir-53 | 6.7462406015 | 3.8909774436 | 0.0002097674 | 0.7604166667 |
| 105 | hsa-miR-3157-5p | 0.3721804511 | 0.1240601504 | 0.0002118311 | 0.7277462121 |
| 106 | brain-mir-41S | 10.5733082707 | 5.9191729323 | 0.0002570966 | 0.7803030303 |
| 107 | brain-mir-201 | 15.4248120301 | 9.5469924812 | 0.000293033 | 0.7291666667 |
| 108 | hsa-miR-5006-3p | 2.5921052632 | 1.4210526316 | 0.0003127522 | 0.743844697 |
| 109 | hsa-miR-4659a-3p | 7.2255639098 | 4.0977443609 | 0.0003606508 | 0.7447916667 |
| 110 | brain-mir-279 | 10.1334586466 | 5.1541353383 | 0.000437069 | 0.6955492424 |
| 111 | brain-mir-111 | 986.477443609 | 590.4022556391 | 0.0004713764 | 0.7504734848 |
| 112 | brain-mir-88 | 2.3646616541 | 1.3778195489 | 0.0005681084 | 0.6912878788 |
| 113 | brain-mir-251 | 1.8909774436 | 0.8458646617 | 0.0005688548 | 0.7296401515 |
| 114 | hsa-miR-4435 | 51.0902255639 | 33.9661654135 | 0.0005693209 | 0.7230113636 |

SUPPLEMENTAL TABLE 1 b-continued

Significantly up-regulated miRNAs in AD vs. controls.

| SEQ ID NO | miRNA | median AD | median Control | t-test p-value single | AUC |
|---|---|---|---|---|---|
| 115 | hsa-miR-5690 | 11.3984962406 | 7.5281954887 | 0.0005745024 | 0.7253787879 |
| 116 | brain-mir-166 | 2.4210526316 | 1.0921052632 | 0.0006242931 | 0.7149621212 |
| 117 | brain-mir-193 | 1.6127819549 | 0.8402255639 | 0.0006339444 | 0.7002840909 |
| 118 | hsa-miR-625-5p | 7.3590225564 | 4.3571428571 | 0.0006972852 | 0.7575757576 |
| 119 | hsa-miR-10b-5p | 683.6766917293 | 406.3007518797 | 0.0008299916 | 0.7168560606 |
| 120 | brain-mir-299 | 3.9586466165 | 1.7857142857 | 0.000839426 | 0.7069128788 |
| 121 | brain-mir-153 | 0.5751879699 | 0.1428571429 | 0.0008478946 | 0.6860795455 |
| 122 | hsa-miR-758 | 0.5939849624 | 0.1240601504 | 0.0008889247 | 0.7589962121 |
| 123 | hsa-miR-30a-3p | 114.6278195489 | 67.3947368421 | 0.0009850641 | 0.7357954545 |
| 124 | brain-mir-220 | 36.4530075188 | 24.4511278195 | 0.0010085027 | 0.7182765152 |
| 125 | brain-mir-392 | 5.5695488722 | 3.1447368421 | 0.001117105 | 0.6586174242 |
| 126 | brain-mir-102 | 34.0526315789 | 22.9229323308 | 0.0011430551 | 0.7571022727 |
| 127 | hsa-let-7b-3p | 47.2894736842 | 26.0338345865 | 0.0011483131 | 0.7471590909 |
| 128 | hsa-miR-340-3p | 23.6879699248 | 9.4248120301 | 0.0011789284 | 0.7651515152 |
| 129 | hsa-miR-484 | 21682.0451127819 | 14260.5789473684 | 0.0012569269 | 0.7211174242 |
| 130 | hsa-miR-30e-3p | 169.3082706767 | 121.1917293233 | 0.0013440534 | 0.7381628788 |
| 131 | brain-mir-72S | 0.4436090226 | 0.1240601504 | 0.0014225572 | 0.7348484848 |
| 132 | hsa-miR-371b-5p | 4.7142857143 | 2.2706766917 | 0.0014389281 | 0.7258522727 |
| 133 | hsa-miR-5581-3p | 2.3327067669 | 1.5620300752 | 0.0015546337 | 0.7064393939 |
| 134 | brain-mir-399 | 19.1616541353 | 12.7706766917 | 0.0015845513 | 0.6619318182 |
| 135 | brain-mir-403 | 4.1842105263 | 2.8364661654 | 0.0016408632 | 0.6695075758 |
| 136 | brain-mir-73 | 21.1766917293 | 12.992481203 | 0.0016958209 | 0.6922348485 |
| 137 | brain-mir-190 | 4.3233082707 | 2.3590225564 | 0.0020611484 | 0.6903409091 |
| 138 | brain-mir-188 | 4.3233082707 | 2.3590225564 | 0.0020611484 | 0.6903409091 |
| 139 | brain-mir-189 | 4.3233082707 | 2.3590225564 | 0.0020611484 | 0.6903409091 |
| 140 | brain-mir-192 | 4.3233082707 | 2.3590225564 | 0.0020611484 | 0.6903409091 |
| 141 | brain-mir-311 | 382.2819548872 | 266.9248120301 | 0.0022861501 | 0.6373106061 |
| 142 | brain-mir-161 | 17.4887218045 | 10.5 | 0.0024185375 | 0.7424242424 |
| 143 | hsa-miR-3074-5p | 24.015037594 | 15.7105263158 | 0.002419588 | 0.740530303 |
| 144 | hsa-miR-30b-5p | 443.9586466165 | 292.2105263158 | 0.0024240637 | 0.712594697 |
| 145 | hsa-miR-576-5p | 291.3834586466 | 207.484962406 | 0.0024324256 | 0.7215909091 |
| 146 | brain-mir-23 | 16.2218045113 | 11.3665413534 | 0.0024712736 | 0.71875 |
| 147 | hsa-miR-943 | 2.0789473684 | 1.3984962406 | 0.0025973005 | 0.6903409091 |
| 148 | brain-mir-351 | 0.272556391 | 0.1278195489 | 0.0026770024 | 0.6439393939 |
| 149 | hsa-miR-4772-3p | 1.0601503759 | 0.219924812 | 0.0030588227 | 0.6884469697 |
| 150 | brain-mir-319 | 4.954887218 | 3.6860902256 | 0.0031658495 | 0.6912878788 |
| 151 | hsa-miR-937 | 13.8984962406 | 8.4323308271 | 0.0032014572 | 0.6174242424 |
| 152 | hsa-miR-181a-2-3p | 222.4135338346 | 173.3458646617 | 0.0034658731 | 0.6770833333 |
| 153 | hsa-miR-4755-5p | 6.4661654135 | 4.0789473684 | 0.003589103 | 0.6590909091 |
| 154 | hsa-miR-3909 | 7.7011278195 | 4.1691729323 | 0.0036634327 | 0.7466856061 |
| 155 | hsa-miR-1260b | 548 | 436.8947368421 | 0.0037982461 | 0.640625 |
| 156 | brain-mir-293 | 3.4022556391 | 2.0056390977 | 0.0043533661 | 0.6879734848 |
| 157 | brain-mir-160 | 13.1635338346 | 9.3646616541 | 0.0047314115 | 0.6496212121 |
| 158 | hsa-miR-2110 | 37.5056390977 | 20.3082706767 | 0.0048976896 | 0.7755681818 |
| 159 | hsa-miR-584-3p | 1.6184210526 | 0.8289473684 | 0.0049666999 | 0.6401515152 |
| 160 | brain-mir-129 | 1.2312030075 | 0.8139097744 | 0.0052865283 | 0.6557765152 |
| 161 | hsa-miR-1280 | 2.8233082707 | 1.1860902256 | 0.0054091313 | 0.6519886364 |
| 162 | hsa-miR-3180-5p | 1.0939849624 | 0.515037594 | 0.0064691451 | 0.6557765152 |
| 163 | hsa-miR-668 | 0.3289473684 | 0.1390977444 | 0.0064710752 | 0.640625 |
| 164 | hsa-miR-4512 | 2.0112781955 | 0.787593985 | 0.0068965461 | 0.6638257576 |
| 165 | hsa-miR-641 | 10.0902255639 | 7.5620300752 | 0.0069660105 | 0.6619318182 |
| 166 | hsa-miR-1233 | 2.0601503759 | 0.9285714286 | 0.007463631 | 0.6586174242 |
| 167 | hsa-miR-378a-5p | 10.0263157895 | 5.4755639098 | 0.0075454956 | 0.7149621212 |
| 168 | hsa-miR-26a-5p | 5634.0676691729 | 4206.2932330827 | 0.007829731 | 0.6789772727 |
| 169 | brain-mir-258 | 5.6973684211 | 0.8233082707 | 0.0079015891 | 0.7201704545 |
| 170 | hsa-miR-1260a | 553.045112782 | 456.4210526316 | 0.0091301492 | 0.6070075758 |

SUPPLEMENTAL TABLE 2

Newly discovered miRNA markers

| SEQ ID NO | miRNA | Sequence |
|---|---|---|
| 126 | brain-mir-102 | UAUGGAGGUCUCUGUCUGGCU |
| 111 | brain-mir-111 | CACUGCUAAAUUGGCUGGCUU |
| 59 | brain-mir-112 | AGCUCUGUCUGUGUCUCUAGG |
| 91 | brain-mir-114 | CACUGCAACCUCUGCCUCCGGU |
| 97 | brain-mir-12 | ACUCCCACUGCUUGACUUGACUAG |
| 160 | brain-mir-129 | CAUGGUCCAUUUUGCUCUGCU |
| 54 | brain-mir-145 | AAGCACUGCCUUUGAACCUGA |
| 23 | brain-mir-149 | AAAAGUAAUCGCACUUUUUG |
| 41 | brain-mir-150 | UGAGGUAGUAGGUGGUGUGC |
| 24 | brain-mir-151 | AAAAGUAAUCGCACUUUUUG |
| 121 | brain-mir-153 | CCUCUUCUCAGAACACUUCCUGG |
| 157 | brain-mir-160 | CACUGCAACCUCUGCCUCC |
| 142 | brain-mir-161 | CUUCGAAAGCGGCUUCGGCU |
| 116 | brain-mir-166 | CUGGCUGCUUCCCUUGGUCU |
| 21 | brain-mir-170 | AAAAGUAAUGGCAGUUUUUG |
| 138 | brain-mir-188 | CCUGACCCCAUGUCGCCUCUGU |
| 139 | brain-mir-189 | CCUGACCCCAUGUCGCCUCUGU |
| 137 | brain-mir-190 | CCUGACCCCAUGUCGCCUCUGU |
| 140 | brain-mir-192 | CCUGACCCCAUGUCGCCUCUGU |
| 117 | brain-mir-193 | AUCCCUUUAUCGUCCUCUAGG |
| 88 | brain-mir-200 | UUCCUGGCUCUCUGUUGCACA |
| 107 | brain-mir-201 | CACCCCACCAGUGCAGGCUG |
| 100 | brain-mir-219 | UCAAGUGUCAUCUGUCCCUAGG |
| 124 | brain-mir-220 | UCCGGAUCCGGCUCCGCGCCU |
| 146 | brain-mir-23 | UUAGUGGCUCCCUCUGCCUGCA |
| 98 | brain-mir-232 | UUGCUCUGCUCUCCCUUGUACU |
| 94 | brain-mir-247 | ACGCCCACUGCUUCACUUGACUAG |
| 50 | brain-mir-248S | GGCGGCGGAGGCGGCGGUG |
| 113 | brain-mir-251 | UGGCCCAAGACCUCAGACC |
| 169 | brain-mir-258 | AUCCCACCCCUGCCCCCA |
| 110 | brain-mir-279 | AUCCCACCGCUGCCACAC |
| 156 | brain-mir-293 | UUGGUGAGGACCCCAAGCUCGG |
| 120 | brain-mir-299 | CAUGCCACUGCACUCCAGCCU |
| 68 | brain-mir-308 | CACUGCACUCCAGCCUGGGUGA |
| 141 | brain-mir-311 | CACUGCAACCUCUGCCUCCCGA |
| 96 | brain-mir-314 | ACUCCCACUGCUUCACUUGAUUAG |
| 150 | brain-mir-319 | CUGCACUCCAGCCUGGGCGA |
| 27 | brain-mir-333 | AAAAGUAAUCGCAGGUUUUG |
| 148 | brain-mir-351 | UGUCUUGCUCUGUUGCCCAGGU |
| 25 | brain-mir-370 | GGCUGGUCUGAUGGUAGUGGGUUA |
| 84 | brain-mir-390 | ACUGCAACCUCCACCUCCUGGGU |
| 125 | brain-mir-392 | CCCGCCUGUCUCUCUCUUGCA |
| 19 | brain-mir-394 | AAAAGUAAUCGUAGUUUUUG |
| 67 | brain-mir-395 | CACUGCACUCCAGCCUGGGUGA |
| 38 | brain-mir-398 | GGCUGGUCCGAGUGCAGUGGUGUU |
| 134 | brain-mir-399 | CACUGCAACCUCUGCCUCC |
| 135 | brain-mir-403 | AAAGACUUCCUUCUCUCGCCU |
| 106 | brain-mir-41S | CCCCGCGCAGGUUCGAAUCCUG |
| 99 | brain-mir-424S | CACUGCACUCCAGCCUGGGUA |
| 73 | brain-mir-431 | CUCGGCCUUUGCUCGCAGCACU |
| 103 | brain-mir-52 | CUGCACUCCAGCCUGGGCGAC |
| 104 | brain-mir-53 | CCCAGGACAGUUUCAGUGAUG |
| 131 | brain-mir-72S | GACCACACUCCAUCCUGGGC |
| 136 | brain-mir-73 | UCCGGAUGUGCUGACCCCUGCG |
| 80 | brain-mir-79 | CACUGCACUCCAGCCUGGCU |
| 81 | brain-mir-80 | CACUGCACUCCAGCCUGGCU |
| 76 | brain-mir-83 | CAGGGUCUCGUUCUGUUGCC |
| 112 | brain-mir-88 | UCUUCACCUGCCUCUGCCUGCA |

SUPPLEMENTAL TABLE 3

Significantly up- or down-regulated miRNAs in MCI vs. controls.

| SEQ ID NO | Marker | median MCI | median Control | t-test p-value single | AUC |
|---|---|---|---|---|---|
| 171 | hsa-miR-29c-3p | 31.34210526 | 74.84022556 | 1.39E−07 | 0.061363636 |
| 172 | hsa-miR-29a-3p | 39.20676692 | 74.4943609 | 2.00E−06 | 0.093181818 |
| 173 | hsa-let-7e-5p | 5465.075188 | 8212.93609 | 5.97E−06 | 0.139772727 |
| 174 | hsa-let-7a-5p | 9288.364662 | 15370.05263 | 1.19E−05 | 0.110227273 |
| 175 | hsa-let-7f-5p | 8601.315789 | 12867.95489 | 1.48E−05 | 0.1125 |

SUPPLEMENTAL TABLE 3-continued

Significantly up- or down-regulated miRNAs in MCI vs. controls.

| SEQ ID NO | Marker | median MCI | median Control | t-test p-value single | AUC |
|---|---|---|---|---|---|
| 176 | hsa-miR-29b-3p | 9.746240602 | 23.65037594 | 9.48E−05 | 0.160227273 |
| 177 | hsa-miR-98 | 98.17293233 | 217.3533835 | 0.00019379 | 0.152272727 |
| 178 | hsa-miR-425-5p | 5634.067669 | 2907.421053 | 0.000351963 | 0.818181818 |
| 179 | hsa-miR-223-3p | 328.8571429 | 470.6090226 | 0.000468269 | 0.230681818 |
| 180 | hsa-miR-181a-2-3p | 241.5451128 | 173.3458647 | 0.000505662 | 0.805681818 |
| 181 | hsa-miR-148b-3p | 137.6541353 | 279.3120301 | 0.000811319 | 0.194318182 |
| 182 | brain-mir-145 | 9.477443609 | 17.7556391 | 0.000969848 | 0.209090909 |
| 183 | hsa-miR-548h-5p | 4.864661654 | 10.08458647 | 0.000996949 | 0.198863636 |
| 184 | hsa-miR-550a-5p | 64.54323308 | 39.41353383 | 0.001127581 | 0.807954545 |
| 185 | hsa-miR-374b-5p | 10.30639098 | 20.54511278 | 0.001150103 | 0.222727273 |
| 186 | hsa-miR-339-3p | 126.4360902 | 87.83458647 | 0.00120356 | 0.811363636 |
| 187 | hsa-miR-3661 | 1.357142857 | 3.716165414 | 0.001208331 | 0.210227273 |
| 188 | brain-mir-190 | 6.342105263 | 2.359022556 | 0.001522223 | 0.818181818 |
| 189 | brain-mir-188 | 6.342105263 | 2.359022556 | 0.001522223 | 0.818181818 |
| 190 | brain-mir-189 | 6.342105263 | 2.359022556 | 0.001522223 | 0.818181818 |
| 191 | brain-mir-192 | 6.342105263 | 2.359022556 | 0.001522223 | 0.818181818 |
| 192 | hsa-miR-550a-3-5p | 54.72368421 | 31.96804511 | 0.001581747 | 0.759090909 |
| 193 | hsa-miR-199a-3p | 4.171052632 | 12.45488722 | 0.001641108 | 0.204545455 |
| 194 | hsa-miR-199b-3p | 4.221804511 | 12.62593985 | 0.001650922 | 0.205681818 |
| 195 | hsa-miR-660-5p | 35.97744361 | 72.91165414 | 0.001678456 | 0.221590909 |
| 196 | hsa-miR-190a | 1.609022556 | 5.597744361 | 0.001784374 | 0.204545455 |
| 197 | brain-mir-220 | 48.59022556 | 24.45112782 | 0.002184462 | 0.790909091 |
| 198 | hsa-miR-548g-5p | 3.447368421 | 9.629699248 | 0.002357652 | 0.225 |
| 199 | hsa-miR-548ar-5p | 3.447368421 | 9.629699248 | 0.002357652 | 0.225 |
| 200 | hsa-miR-548x-5p | 3.447368421 | 9.629699248 | 0.002357652 | 0.225 |
| 201 | hsa-miR-548aj-5p | 3.447368421 | 9.629699248 | 0.002357652 | 0.225 |
| 202 | brain-mir-394 | 2.603383459 | 7.836466165 | 0.002559946 | 0.215909091 |
| 203 | brain-mir-149 | 2.603383459 | 7.836466165 | 0.002559946 | 0.215909091 |
| 204 | brain-mir-151 | 2.603383459 | 7.836466165 | 0.002559946 | 0.215909091 |
| 205 | hsa-let-7c | 6816.890977 | 11249.52256 | 0.002574232 | 0.196590909 |
| 206 | brain-mir-333 | 2.603383459 | 7.836466165 | 0.002690942 | 0.215909091 |
| 207 | brain-mir-170 | 2.603383459 | 7.836466165 | 0.002759117 | 0.225 |
| 208 | hsa-miR-152 | 12.7443609 | 22.23120301 | 0.00331602 | 0.222727273 |
| 209 | hsa-miR-15a-5p | 632.3984962 | 1472.996241 | 0.003376847 | 0.2 |
| 210 | hsa-miR-197-5p | 0.830827068 | 0.135338346 | 0.00340422 | 0.811363636 |
| 211 | brain-mir-399 | 21.7518797 | 12.77067669 | 0.003703683 | 0.781818182 |
| 212 | hsa-miR-3158-3p | 433.6691729 | 309.3571429 | 0.003815704 | 0.732954545 |
| 213 | brain-mir-150 | 12.15413534 | 19.48120301 | 0.003816641 | 0.284090909 |
| 214 | hsa-miR-424-3p | 194.537594 | 105.6146617 | 0.003852425 | 0.775 |
| 215 | hsa-miR-148a-3p | 578.1203008 | 845.5263158 | 0.004120012 | 0.240909091 |
| 216 | hsa-miR-3200-3p | 16.64473684 | 23.5037594 | 0.004405877 | 0.303409091 |
| 217 | hsa-miR-628-3p | 2.796992481 | 7.116541353 | 0.004410063 | 0.243181818 |
| 218 | hsa-let-7d-5p | 412.6240602 | 598.4849624 | 0.004602573 | 0.217045455 |
| 219 | hsa-miR-4781-3p | 13.96616541 | 10.07142857 | 0.004719502 | 0.769318182 |
| 220 | brain-mir-160 | 17.84210526 | 9.364661654 | 0.005169293 | 0.768181818 |
| 221 | hsa-miR-374a-5p | 1.793233083 | 5.186090226 | 0.005650498 | 0.276136364 |
| 222 | hsa-miR-338-3p | 0.593984962 | 2.716165414 | 0.006017454 | 0.302272727 |
| 223 | hsa-miR-340-5p | 8.187969925 | 21.98496241 | 0.006522277 | 0.252272727 |
| 224 | brain-mir-395 | 5.890977444 | 4.323308271 | 0.006577993 | 0.719318182 |
| 225 | brain-mir-308 | 5.890977444 | 4.323308271 | 0.006577993 | 0.719318182 |
| 226 | brain-mir-53 | 5.757518797 | 3.890977444 | 0.006988766 | 0.7125 |
| 227 | brain-mir-229 | 0.417293233 | 1.864661654 | 0.007037494 | 0.192045455 |
| 228 | hsa-miR-151a-3p | 3088.518797 | 1892.661654 | 0.00727488 | 0.713636364 |
| 229 | hsa-miR-1234 | 2.323308271 | 5.62406015 | 0.00831879 | 0.270454545 |
| 230 | hsa-miR-874 | 6.437969925 | 10.02631579 | 0.008872069 | 0.269318182 |
| 231 | hsa-miR-548av-5p | 3.906015038 | 9.654135338 | 0.008945083 | 0.245454545 |
| 232 | hsa-miR-548k | 3.906015038 | 9.654135338 | 0.008945083 | 0.245454545 |
| 233 | brain-mir-101 | 3.883458647 | 6.633458647 | 0.009086578 | 0.271590909 |
| 234 | hsa-miR-30d-5p | 10223.82707 | 7038.496241 | 0.009299073 | 0.729545455 |
| 235 | hsa-miR-3200-5p | 22 | 37.82706767 | 0.00954828 | 0.282954545 |

SUPPLEMENTAL TABLE 4

Overview of miRNA markers, including sequence information

| # | Name | Sequence |
|---|------|----------|
| 1 | hsa-miR-144-5p | GGAUAUCAUCAUAUACUGUAAG |
| 2 | hsa-let-7f-5p | UGAGGUAGUAGAUUGUAUAGUU |
| 3 | hsa-let-7e-5p | UGAGGUAGGAGGUUGUAUAGUU |
| 4 | hsa-let-7a-5p | UGAGGUAGUAGGUUGUAUAGUU |
| 5 | hsa-miR-107 | AGCAGCAUUGUACAGGGCUAUCA |
| 6 | hsa-let-7g-5p | UGAGGUAGUAGUUUGUACAGUU |
| 7 | hsa-miR-103a-3p | AGCAGCAUUGUACAGGGCUAUGA |
| 8 | hsa-miR-98 | UGAGGUAGUAAGUUGUAUUGUU |
| 9 | hsa-miR-29c-3p | UAGCACCAUUUGAAAUCGGUUA |
| 10 | hsa-miR-101-3p | UACAGUACUGUGAUAACUGAA |
| 11 | hsa-miR-548h-5p | AAAAGUAAUCGCGGUUUUUGUC |
| 12 | hsa-miR-106b-3p | CCGCACUGUGGGUACUUGCUGC |
| 13 | hsa-miR-15a-5p | UAGCAGCACAUAAUGGUUUGUG |
| 14 | hsa-miR-548g-5p | UGCAAAAGUAAUUGCAGUUUUUG |
| 15 | hsa-miR-548ar-5p | AAAAGUAAUUGCAGUUUUUGC |
| 16 | hsa-miR-548x-5p | UGCAAAAGUAAUUGCAGUUUUUG |
| 17 | hsa-miR-548aj-5p | UGCAAAAGUAAUUGCAGUUUUUG |
| 18 | hsa-let-7c | UGAGGUAGUAGGUUGUAUGGUU |
| 19 | brain-mir-394 | AAAAGUAAUCGUAGUUUUUG |
| 20 | hsa-miR-1294 | UGUGAGGUUGGCAUUGUUGUCU |
| 21 | brain-mir-170 | AAAAGUAAUGGCAGUUUUUG |
| 22 | hsa-miR-199a-3p | ACAGUAGUCUGCACAUUGGUUA |
| 23 | brain-mir-149 | AAAAGUAAUCGCACUUUUUG |
| 24 | brain-mir-151 | AAAAGUAAUCGCACUUUUUG |
| 25 | brain-mir-370 | GGCUGGUCUGAUGGUAGUGGGUUA |
| 26 | hsa-miR-199b-3p | ACAGUAGUCUGCACAUUGGUUA |
| 27 | brain-mir-333 | AAAAGUAAUCGCAGGUUUUG |
| 28 | hsa-miR-628-3p | UCUAGUAAGAGUGGCAGUCGA |
| 29 | hsa-miR-190a | UGAUAUGUUUGAUAUAUUAGGU |
| 30 | hsa-miR-29b-3p | UAGCACCAUUUGAAAUCAGUGUU |
| 31 | hsa-miR-660-5p | UACCCAUUGCAUAUCGGAGUUG |
| 32 | hsa-miR-143-3p | UGAGAUGAAGCACUGUAGCUC |
| 33 | hsa-miR-548av-5p | AAAAGUACUUGCGGAUUU |
| 34 | hsa-miR-548k | AAAAGUACUUGCGGAUUUUGCU |
| 35 | hsa-miR-29a-3p | UAGCACCAUCUGAAAUCGGUUA |
| 36 | hsa-miR-548i | AAAAGUAAUUGCGGAUUUUGCC |
| 37 | hsa-miR-17-3p | ACUGCAGUGAAGGCACUUGUAG |
| 38 | brain-mir-398 | GGCUGGUCCGAGUGCAGUGGUGUU |
| 39 | hsa-miR-148a-3p | UCAGUGCACUACAGAACUUUGU |
| 40 | hsa-miR-126-3p | UCGUACCGUGAGUAAUAAUGCG |
| 41 | brain-mir-150 | UGAGGUAGUAGGUUGUGUGC |
| 42 | hsa-let-7i-5p | UGAGGUAGUAGUUUGUGCUGUU |
| 43 | hsa-miR-33b-5p | GUGCAUUGCUGUUGCAUUGC |
| 44 | hsa-miR-3200-3p | CACCUUGCGCUACUCAGGUCUG |
| 45 | hsa-miR-548o-5p | AAAAGUAAUUGCGGUUUUUGCC |
| 46 | hsa-miR-152 | UCAGUGCAUGACAGAACUUGG |
| 47 | hsa-miR-548am-5p | AAAAGUAAUUGCGGUUUUUGCC |
| 48 | hsa-miR-548au-5p | AAAAGUAAUUGCGGUUUUUGC |
| 49 | hsa-miR-548c-5p | AAAAGUAAUUGCGGUUUUUGCC |
| 50 | brain-mir-248S | GGCGGCGGAGGCGGCGGUG |
| 51 | hsa-miR-215 | AUGACCUAUGAAUUGACAGAC |
| 52 | hsa-miR-340-5p | UUAUAAAGCAAUGAGACUGAUU |
| 53 | hsa-miR-1301 | UUGCAGCUGCCUGGGAGUGACUUC |
| 54 | brain-mir-145 | AAGCACUGCCUUUGAACCUGA |
| 55 | hsa-miR-504 | AGACCCUGGUCUGCACUCUAUC |
| 56 | hsa-miR-30d-5p | UGUAAACAUCCCCGACUGGAAG |
| 57 | hsa-miR-4781-3p | AAUGUUGGAAUCCUCGCUAGAG |
| 58 | hsa-miR-151a-3p | CUAGACUGAAGCUCCUUGAGG |
| 59 | brain-mir-112 | AGCUCUGUCUGUGUCUCUAGG |
| 60 | hsa-miR-28-3p | CACUAGAUUGUGAGCUCCUGGA |
| 61 | hsa-miR-26b-3p | CCUGUUCUCCAUUACUUGGCUC |
| 62 | hsa-miR-1468 | CUCCGUUUGCCUGUUUCGCUG |
| 63 | hsa-miR-128 | UCACAGUGAACCGGUCUCUUU |
| 64 | hsa-miR-550a-5p | AGUGCCUGAGGGAGUAAGAGCCC |
| 65 | hsa-miR-5010-3p | UUUUGUGUCUCCCAUUCCCCAG |
| 66 | hsa-miR-148b-5p | AAGUUCUGUUAUACACUCAGGC |
| 67 | brain-mir-395 | CACUGCACUCCAGCCUGGGUGA |
| 68 | brain-mir-308 | CACUGCACUCCAGCCUGGGUGA |
| 69 | hsa-miR-1285-5p | GAUCUCACUUUGUUGCCCAGG |
| 70 | hsa-miR-5001-3p | UUCUGCUCUGUCCAGGUCCUU |
| 71 | hsa-miR-3127-3p | UCCCCUUCUGCAGGCCUGCGG |
| 72 | hsa-miR-3157-3p | CUGCCCUAGUCUAGCUGAAGCU |
| 73 | brain-mir-431 | CUCGGCCUUUGCUCGCAGCACU |
| 74 | hsa-miR-550a-3-5p | AGUGCCUGAGGGAGUAAGAG |
| 75 | hsa-miR-361-5p | UUAUCAGAAUCUCCAGGGGUAC |
| 76 | brain-mir-83 | CAGGGUCUCGUUCUGUUGCC |
| 77 | hsa-miR-589-5p | UGAGAACCACGUCUGCUCUGAG |

SUPPLEMENTAL TABLE 4-continued

Overview of miRNA markers, including sequence information

| | | |
|---|---|---|
| 78 | hsa-miR-425-5p | AAUGACACGAUCACUCCCGUUGA |
| 79 | hsa-miR-30a-5p | UGUAAACAUCCUCGACUGGAAG |
| 80 | brain-mir-79 | CACUGCACUCCAGCCUGGCU |
| 81 | brain-mir-80 | CACUGCACUCCAGCCUGGCU |
| 82 | hsa-miR-330-5p | UCUCUGGGCCUGUGUCUUAGGC |
| 83 | hsa-miR-186-5p | CAAAGAAUUCUCCUUUUGGGCU |
| 84 | brain-mir-390 | ACUGCAACCUCCACCUCCUGGGU |
| 85 | hsa-let-7d-3p | CUAUACGACCUGCUGCCUUUCU |
| 86 | hsa-miR-328 | CUGGCCCUCUCUGCCCUUCCGU |
| 87 | hsa-miR-30c-5p | UGUAAACAUCCUACACUCUCAGC |
| 88 | brain-mir-200 | UUCCUGGCUCUCUGUUGCACA |
| 89 | hsa-miR-363-3p | AAUUGCACGGUAUCCAUCUGUA |
| 90 | hsa-miR-339-3p | UGAGCGCCUCGACGACAGAGCCG |
| 91 | brain-mir-114 | CACUGCAACCUCUGCCUCCGGU |
| 92 | hsa-miR-942 | UCUUCUCUGUUUUGGCCAUGUG |
| 93 | hsa-miR-345-5p | GCUGACUCCUAGUCCAGGGCUC |
| 94 | brain-mir-247 | ACGCCCACUGCUUCACUUGACUAG |
| 95 | hsa-miR-4742-3p | UCUGUAUUCUCCUUUGCCUGCAG |
| 96 | brain-mir-314 | ACUCCCACUGCUUCACUUGAUUAG |
| 97 | brain-mir-12 | ACUCCCACUGCUUGACUUGACUAG |
| 98 | brain-mir-232 | UUGCUCUGCUCUCCCUUGUACU |
| 99 | brain-mir-424S | CACUGCACUCCAGCCUGGGUA |
| 100 | brain-mir-219 | UCAAGUGUCAUCUGUCCCUAGG |
| 101 | hsa-miR-10a-5p | UACCCUGUAGAUCCGAAUUUGUG |
| 102 | hsa-miR-3605-3p | CCUCCGUGUUACCUGUCCUCUAG |
| 103 | brain-mir-52 | CUGCACUCCAGCCUGGGCGAC |
| 104 | brain-mir-53 | CCCAGGACAGUUUCAGUGAUG |
| 105 | hsa-miR-3157-5p | UUCAGCCAGGCUAGUGCAGUCU |
| 106 | brain-mir-41S | CCCCGCGCAGGUUCGAAUCCUG |
| 107 | brain-mir-201 | CACCCCACCAGUGCAGGCUG |
| 108 | hsa-miR-5006-3p | UUUCCCUUUCCAUCCUGGCAG |
| 109 | hsa-miR-4659a-3p | UUUCUUCUUAGACAUGGCAACG |
| 110 | brain-mir-279 | AUCCCACCGCUGCCACAC |
| 111 | brain-mir-111 | CACUGCUAAAUUUGGCUGGCUU |
| 112 | brain-mir-88 | UCUUACCUGCCUCUGCCUGCA |
| 113 | brain-mir-251 | UGGCCCAAGACCUCAGACC |
| 114 | hsa-miR-4435 | AUGGCCAGAGCUCACACAGAGG |
| 115 | hsa-miR-5690 | UCAGCUACUACCUCUAUUAGG |
| 116 | brain-mir-166 | CUGGCUGCUUCCCUUGGUCU |
| 117 | brain-mir-193 | AUCCCUUUAUCUGUCCUCUAGG |
| 118 | hsa-miR-625-5p | AGGGGGAAAGUUCUAUAGUCC |
| 119 | hsa-miR-10b-5p | UACCCUGUAGAACCGAAUUUGUG |
| 120 | brain-mir-299 | CAUGCCACUGCACUCCAGCCU |
| 121 | brain-mir-153 | CCUCUUCUCAGAACACUUCCUGG |
| 122 | hsa-miR-758 | UUUGUGACCUGGUCCACUAACC |
| 123 | hsa-miR-30a-3p | CUUUCAGUCGGAUGUUUGCAGC |
| 124 | brain-mir-220 | UCCGGAUCCGGCUCCGCGCCU |
| 125 | brain-mir-392 | CCCGCCUGUCUCUCUCUUGCA |
| 126 | brain-mir-102 | UAUGGAGGUCUCUGUCUGGCU |
| 127 | hsa-let-7b-3p | CUAUACAACCUACUGCCUUCCC |
| 128 | hsa-miR-340-3p | UCCGUCUCAGUUACUUUAUAGC |
| 129 | hsa-miR-484 | UCAGGCUCAGUCCCCUCCCGAU |
| 130 | hsa-miR-30e-3p | CUUUCAGUCGGAUGUUUACAGC |
| 131 | brain-mir-72S | GACCACACUCCAUCCUGGGC |
| 132 | hsa-miR-371b-5p | ACUCAAAAGAUGGCGGCACUUU |
| 133 | hsa-miR-5581-3p | UUCCAUGCCUCCUAGAAGUUCC |
| 134 | brain-mir-399 | CACUGCAACCUCUGCCUCC |
| 135 | brain-mir-403 | AAAGACUUCCUUCUCUCGCCU |
| 136 | brain-mir-73 | UCCGGAUGUGCUGACCCCUGCG |
| 137 | brain-mir-190 | CCUGACCCCAUGUCGCCUCUGU |
| 138 | brain-mir-188 | CCUGACCCCAUGUCGCCUCUGU |
| 139 | brain-mir-189 | CCUGACCCCAUGUCGCCUCUGU |
| 140 | brain-mir-192 | CCUGACCCCAUGUCGCCUCUGU |
| 141 | brain-mir-311 | CACUGCAACCUCUGCCUCCCGA |
| 142 | brain-mir-161 | CUUCGAAAGCGGCUUCGGCU |
| 143 | hsa-miR-3074-5p | GUUCCUGCUGAACUGAGCCAG |
| 144 | hsa-miR-30b-5p | UGUAAACAUCCUACACUCAGCU |
| 145 | hsa-miR-576-5p | AUUCUAAUUUCUCCACGUCUUU |
| 146 | brain-mir-23 | UUAGUGGCUCCCUCUGCCUGCA |
| 147 | hsa-miR-943 | CUGACUGUUGCCGUCCUCCAG |
| 148 | brain-mir-351 | UGUCUUGCUCUGUUGCCCAGGU |
| 149 | hsa-miR-4772-3p | CCUGCAACUUUGCCUGAUCAGA |
| 150 | brain-mir-319 | CUGCACUCCAGCCUGGGCGA |
| 151 | hsa-miR-937 | AUCCGCGCUCUGACUCUCUGCC |
| 152 | hsa-miR-181a-2-3p | ACCACUGACCGUUGACUGUACC |
| 153 | hsa-miR-4755-5p | UUUCCCUUCAGAGCCUGGCUUU |
| 154 | hsa-miR-3909 | UGUCCUCUAGGGCCUGCAGUCU |

SUPPLEMENTAL TABLE 4-continued

Overview of miRNA markers, including sequence information

| | | |
|---|---|---|
| 155 | hsa-miR-1260b | AUCCCACCACUGCCACCAU |
| 156 | brain-mir-293 | UUGGUGAGGACCCCAAGCUCGG |
| 157 | brain-mir-160 | CACUGCAACCUCUGCCUCC |
| 158 | hsa-miR-2110 | UUGGGGAAACGGCCGCUGAGUG |
| 159 | hsa-miR-584-3p | UCAGUUCCAGGCCAACCAGGCU |
| 160 | brain-mir-129 | CAUGGUCCAUUUGCUCUGCU |
| 161 | hsa-miR-1280 | UCCCACCGCUGCCACCC |
| 162 | hsa-miR-3180-5p | CUUCCAGACGCUCCGCCCCACGUCG |
| 163 | hsa-miR-668 | UGUCACUCGGCUCGGCCCACUAC |
| 164 | hsa-miR-4512 | CAGGGCCUCACUGUAUCGCCCA |
| 165 | hsa-miR-641 | AAAGACAUAGGAUAGAGUCACCUC |
| 166 | hsa-miR-1233 | UGAGCCCUGUCCUCCCGCAG |
| 167 | hsa-miR-378a-5p | CUCCUGACUCCAGGUCCUGUGU |
| 168 | hsa-miR-26a-5p | UUCAAGUAAUCCAGGAUAGGCU |
| 169 | brain-mir-258 | AUCCCACCCCUGCCCCCA |
| 170 | hsa-miR-1260a | AUCCCACCUCUGCCACCA |
| 171 | hsa-miR-29c-3p | UAGCACCAUUUGAAAUCGGUUA |
| 172 | hsa-miR-29a-3p | UAGCACCAUCUGAAAUCGGUUA |
| 173 | hsa-let-7e-5p | UGAGGUAGGAGGUUGUAUAGUU |
| 174 | hsa-let-7a-5p | UGAGGUAGUAGGUUGUAUAGUU |
| 175 | hsa-let-7f-5p | UGAGGUAGUAGAUUGUAUAGUU |
| 176 | hsa-miR-29b-3p | UAGCACCAUUUGAAAUCAGUGUU |
| 177 | hsa-miR-98 | UGAGGUAGUAAGUUGUAUUGUU |
| 178 | hsa-miR-425-5p | AAUGACACGAUCACUCCCGUUGA |
| 179 | hsa-miR-223-3p | UGUCAGUUUGUCAAAUACCCCA |
| 180 | hsa-miR-181a-2-3p | ACCACUGACCGUUGACUGUACC |
| 181 | hsa-miR-148b-3p | UCAGUGCAUCACAGAACUUUGU |
| 182 | brain-mir-145 | AAGCACUGCCUUUGAACCUGA |
| 183 | hsa-miR-548h-5p | AAAAGUAAUCGCGGUUUUUGUC |
| 184 | hsa-miR-550a-5p | AGUGCCUGAGGGAGUAAGAGCCC |
| 185 | hsa-miR-374b-5p | AUAUAAUACAACCUGCUAAGUG |
| 186 | hsa-miR-339-3p | UGAGCGCCUCGACGACAGAGCCG |
| 187 | hsa-miR-3661 | UGACCUGGGACUCGGACAGCUG |
| 188 | brain-mir-190 | CCUGACCCCAUGUCGCCUCUGU |
| 189 | brain-mir-188 | CCUGACCCCAUGUCGCCUCUGU |
| 190 | brain-mir-189 | CCUGACCCCAUGUCGCCUCUGU |
| 191 | brain-mir-192 | CCUGACCCCAUGUCGCCUCUGU |
| 192 | hsa-miR-550a-3-5p | AGUGCCUGAGGGAGUAAGAG |
| 193 | hsa-miR-199a-3p | ACAGUAGUCUGCACAUUGGUUA |
| 194 | hsa-miR-199b-3p | ACAGUAGUCUGCACAUUGGUUA |
| 195 | hsa-miR-660-5p | UACCCAUUGCAUAUCGGAGUUG |
| 196 | hsa-miR-190a | UGAUAUGUUUGAUAUAUUAGGU |
| 197 | brain-mir-220 | UCCGGAUCCGGCUCCGCGCCU |
| 198 | hsa-miR-548g-5p | UGCAAAAGUAAUUGCAGUUUUUG |
| 199 | hsa-miR-548ar-5p | AAAAGUAAUUGCAGUUUUUGC |
| 200 | hsa-miR-548x-5p | UGCAAAAGUAAUUGCAGUUUUUG |
| 201 | hsa-miR-548aj-5p | UGCAAAAGUAAUUGCAGUUUUUG |
| 202 | brain-mir-394 | AAAAGUAAUCGUAGUUUUUG |
| 203 | brain-mir-149 | AAAAGUAAUCGCACUUUUUG |
| 204 | brain-mir-151 | AAAAGUAAUCGCACUUUUUG |
| 205 | hsa-let-7c | UGAGGUAGUAGGUUGUAUGGUU |
| 206 | brain-mir-333 | AAAAGUAAUCGCAGGUUUUG |
| 207 | brain-mir-170 | AAAAGUAAUGGCAGUUUUUG |
| 208 | hsa-miR-152 | UCAGUGCAUGACAGAACUUGG |
| 209 | hsa-miR-15a-5p | UAGCAGCACAUAAUGGUUUGUG |
| 210 | hsa-miR-197-5p | CGGGUAGAGAGGGCAGUGGGAGG |
| 211 | brain-mir-399 | CACUGCAACCUCUGCCUCC |
| 212 | hsa-miR-3158-3p | AAGGGCUUCCUCUCUGCAGGAC |
| 213 | brain-mir-150 | UGAGGUAGUAGGUGGUGUGC |
| 214 | hsa-miR-424-3p | CAAAACGUGAGGCGCUGCUAU |
| 215 | hsa-miR-148a-3p | UCAGUGCACUACAGAACUUUGU |
| 216 | hsa-miR-3200-3p | CACCUUGCGCUACUCAGGUCUG |
| 217 | hsa-miR-628-3p | UCUAGUAAGAGUGGCAGUCGA |
| 218 | hsa-let-7d-5p | AGAGGUAGUAGGUUGCAUAGUU |
| 219 | hsa-miR-4781-3p | AAUGUUGGAAUCCUCGCUAGAG |
| 220 | brain-mir-160 | CACUGCAACCUCUGCCUCC |
| 221 | hsa-miR-374a-5p | UUAUAAUACAACCUGAUAAGUG |
| 222 | hsa-miR-338-3p | UCCAGCAUCAGUGAUUUUGUUG |
| 223 | hsa-miR-340-5p | UUAUAAAGCAAUGAGACUGAUU |
| 224 | brain-mir-395 | CACUGCACUCCAGCCUGGGUGA |
| 225 | brain-mir-308 | CACUGCACUCCAGCCUGGGUGA |
| 226 | brain-mir-53 | CCCAGGACAGUUUCAGUGAUG |
| 227 | brain-mir-229 | AUCCCACCUCUGCUACCA |
| 228 | hsa-miR-151a-3p | CUAGACUGAAGCUCCUUGAGG |
| 229 | hsa-miR-1234 | UCGGCCUGACCACCCACCCCAC |
| 230 | hsa-miR-874 | CUGCCCUGGCCCGAGGGACCGA |
| 231 | hsa-miR-548av-5p | AAAAGUACUUGCGGAUUU |

SUPPLEMENTAL TABLE 4-continued

Overview of miRNA markers, including sequence information

| 232 | hsa-miR-548k | AAAAGUACUUGCGGAUUUUGCU |
| 233 | brain-mir-101 | AGACCUACUUAUCUACCAACA |
| 234 | hsa-miR-30d-5p | UGUAAACAUCCCCGACUGGAAG |
| 235 | hsa-miR-3200-5p | AAUCUGAGAAGGCGCACAAGGU |

What is claimed is:
1. A method of treating Alzheimer's Disease in a patient in need thereof, said method comprising administering an anti-Alzheimer's Disease therapy to the patient, wherein a blood sample from the patient exhibits an expression level value of at least one miRNA selected from the group consisting of SEQ ID NO 1, SEQ ID NO 2, SEQ ID NO 4, SEQ ID NO 5, SEQ ID NO 7, SEQ ID NO 56, SEQ ID NO 58, SEQ ID NO 59, SEQ ID NO 64, SEQ ID NO 65, SEQ ID NO 66, SEQ

ID NO 69, SEQ ID NO 70, SEQ ID NO 71, SEQ ID NO 72, SEQ ID NO 73, SEQ ID NO 78, SEQ ID NO 85, SEQ ID NO 142 and SEQ ID NO 236 compared to a reference expression level value.

2. The method according to claim 1, wherein the at least one miRNA from the sample is selected from the group consisting of SEQ ID NO 59, SEQ ID NO 65, SEQ ID NO 1, and SEQ ID NO 56.

3. The method according to claim 1, wherein the at least one miRNA from the sample includes all seven of brain-miR-112, hsa-miR-5010-3p, hsa-miR-103a-3p, hsa-miR-107, hsa-let-7d-3p, hsa-miR-532-5p, and brain-miR-161.

4. The method according to claim 1, wherein the at least one miRNA from the sample includes a set of 5 miRNAs selected from the group consisting of

```
brain-mir-112 hsa-miR-5010-3p hsa-miR-1285-5p hsa-miR-151a-3p
hsa-let-7f-5p,
hsa-miR-3127-3p hsa-miR-1285-5p hsa-miR-425-5p hsa-miR-148b-5p
hsa-miR-144-5p,
hsa-miR-3127-3p hsa-miR-3157-3p hsa-miR-148b-5p hsa-miR-151a-3p
hsa-miR-144-5p,
hsa-miR-3127-3p hsa-miR-1285-5p hsa-miR-425-5p hsa-miR-151a-3p
hsa-miR-144-5p,
hsa-miR-1285-5p brain-mir-112 hsa-miR-5010-3p hsa-miR-151a-3p
hsa-let-7a-5p,
hsa-miR-5001-3p hsa-miR-1285-5p hsa-miR-425-5p hsa-miR-148b-5p
hsa-miR-144-5p,
hsa-miR-3127-3p hsa-miR-1285-5p hsa-miR-148b-5p hsa-miR-151a-3p
hsa-miR-144-5p,
hsa-miR-1285-5p hsa-miR-5010-3p hsa-miR-425-5p hsa-miR-148b-5p
hsa-miR-144-5p,
hsa-miR-1285-5p hsa-miR-5010-3p hsa-miR-151a-3p hsa-miR-144-5p
hsa-let-7a-5p,
hsa-miR-1285-5p brain-mir-112 hsa-miR-425-5p hsa-miR-151a-3p
hsa-miR-144-5p,
hsa-miR-5001-3p hsa-miR-1285-5p brain-mir-112 hsa-miR-151a-3p
hsa-let-7f-5p,
hsa-miR-1285-5p hsa-miR-5010-3p hsa-miR-148b-5p hsa-miR-144-5p
hsa-let-7f-5p,
hsa-miR-1285-5p hsa-miR-3157-3p hsa-miR-148b-5p hsa-miR-151a-3p
hsa-miR-144-5p,
hsa-miR-5001-3p hsa-miR-1285-5p hsa-miR-5010-3p hsa-miR-151a-3p
hsa-let-7f-5p,
brain-mir-431 hsa-miR-1285-5p hsa-miR-3157-3p hsa-miR-151a-3p
hsa-miR-144-5p,
hsa-miR-3127-3p hsa-miR-1285-5p brain-mir-112 hsa-miR-425-5p
hsa-miR-151a-3p,
hsa-miR-1285-5p hsa-miR-5010-3p hsa-miR-151a-3p hsa-miR-144-5p
hsa-let-7f-5p,
hsa-miR-550a- 5phsa-miR-1285-5p brain-mir-112 hsa-miR-151a-3p
hsa-let-7f-5p,
hsa-miR-1285-5p brain-mir-112 hsa-miR-148b-5p hsa-miR-151a-3p
hsa-miR-144-5p, and
hsa-miR-5001-3p brain-mir-112 hsa-miR-5010-3p hsa-miR-151a-3p
hsa-let-7f-5p.
```

5. The method according to claim 4, further comprising adding the expression level values of the set of five miRNAs.

6. The method according to claim 1, wherein the determination of the expression level value of the at least one miRNA from the sample is obtained by use of a method selected from the group consisting of a sequencing-based method, an array-based method and a PCR-based method.

7. The method according to claim 1, wherein the expression levels values of at least 2 miRNAs in the sample are determined.

8. The method according to claim 1, wherein the blood sample from the patient also exhibits an expression level value of at least one miRNA selected from the group consisting of hsa-miR-26b-3p, hsa-miR-26a-5p, brain-miR-161 and hsa-miR-5010-3p compared to a reference expression level value.

9. A kit for performing the method according to claim 1, said kit comprising
means for determining in said blood sample from said patient, an expression level value of at least one miRNA selected from the group consisting of miRNAs having the sequence SEQ ID NO 1, SEQ ID NO 2, SEQ ID NO 4, SEQ ID NO 5, SEQ ID NO 7, SEQ ID NO 56, SEQ ID NO 58, SEQ ID NO 59, SEQ ID NO 64, SEQ ID NO 65, SEQ ID NO 66, SEQ ID NO 69, SEQ ID NO 70, SEQ ID NO 71, SEQ ID NO 72, SEQ ID NO 73, SEQ ID NO 78, SEQ ID NO 85, SEQ ID NO 142 and SEQ ID NO 236.

10. The kit of claim 9, further comprising at least one reference pattern of expression levels values for comparing with the expression level values of the at least one miRNA from said sample.

11. The method according to claim 7, wherein the expression level values of at least 3 miRNAs in the sample are determined.

12. The method according to claim 11, wherein the expression level values of at least 4 miRNAs in the sample are determined.

13. The method according to claim 12, wherein the expression level values of at least 5 miRNAs in the sample are determined.

14. The method according to claim 13, wherein the expression level values of at least 6 miRNAs in the sample are determined.

15. The method according to claim 14, wherein the expression level values of at least 7 miRNAs in the sample are determined.

16. The method according to claim 15, wherein the expression level values of at least 8 miRNAs in the sample are determined.

17. The method according to claim 16, wherein the expression level values of at least 9 miRNAs in the sample are determined.

18. The method according to claim 17, wherein the expression level values of at least 10 miRNAs in the sample are determined.

19. The method according to claim 18, wherein the expression level values of at least 12 miRNAs in the sample are determined.

* * * * *

SEQUENCE LISTING

<160> NUMBER OF SEQ ID NOS: 235

<210> SEQ ID NO 1
<211> LENGTH: 22
<212> TYPE: RNA
<213> ORGANISM: Homo sapiens

<400> SEQUENCE: 1
ggauaucauc auauacugua ag                                          22

<210> SEQ ID NO 2
<211> LENGTH: 22
<212> TYPE: RNA
<213> ORGANISM: Homo sapiens

<400> SEQUENCE: 2
ugagguagua gauuguauag uu                                          22

<210> SEQ ID NO 3
<211> LENGTH: 22
<212> TYPE: RNA
<213> ORGANISM: Homo sapiens

<400> SEQUENCE: 3
ugagguagga gguuguauag uu                                          22

<210> SEQ ID NO 4
<211> LENGTH: 22
<212> TYPE: RNA
<213> ORGANISM: Homo sapiens

<400> SEQUENCE: 4
ugagguagua gguuguauag uu                                          22

<210> SEQ ID NO 5
<211> LENGTH: 23
<212> TYPE: RNA
<213> ORGANISM: Homo sapiens

<400> SEQUENCE: 5
agcagcauug uacagggcua uca                                         23

<210> SEQ ID NO 6
<211> LENGTH: 22
<212> TYPE: RNA
<213> ORGANISM: Homo sapiens

<400> SEQUENCE: 6
ugagguagua guuuguacag uu                                          22

<210> SEQ ID NO 7
<211> LENGTH: 23
<212> TYPE: RNA
<213> ORGANISM: Homo sapiens

```
<400> SEQUENCE: 7
agcagcauug uacagggcua uga                                           23

<210> SEQ ID NO 8
<211> LENGTH: 22
<212> TYPE: RNA
<213> ORGANISM: Homo sapiens

<400> SEQUENCE: 8
ugagguagua aguuguauug uu                                            22

<210> SEQ ID NO 9
<211> LENGTH: 22
<212> TYPE: RNA
<213> ORGANISM: Homo sapiens

<400> SEQUENCE: 9
uagcaccauu ugaaaucggu ua                                            22

<210> SEQ ID NO 10
<211> LENGTH: 21
<212> TYPE: RNA
<213> ORGANISM: Homo sapiens

<400> SEQUENCE: 10
uacaguacug ugauaacuga a                                             21

<210> SEQ ID NO 11
<211> LENGTH: 22
<212> TYPE: RNA
<213> ORGANISM: Homo sapiens

<400> SEQUENCE: 11
aaaaguaauc gcgguuuuug uc                                            22

<210> SEQ ID NO 12
<211> LENGTH: 22
<212> TYPE: RNA
<213> ORGANISM: Homo sapiens

<400> SEQUENCE: 12
ccgcacugug gguacuugcu gc                                            22

<210> SEQ ID NO 13
<211> LENGTH: 22
<212> TYPE: RNA
<213> ORGANISM: Homo sapiens

<400> SEQUENCE: 13
uagcagcaca uaaugguuug ug                                            22

<210> SEQ ID NO 14
<211> LENGTH: 23
<212> TYPE: RNA
<213> ORGANISM: Homo sapiens

<400> SEQUENCE: 14
ugcaaaagua auugcaguuu uug                                           23

<210> SEQ ID NO 15
<211> LENGTH: 21
<212> TYPE: RNA
```

```
<213> ORGANISM: Homo sapiens

<400> SEQUENCE: 15
aaaaguaauu gcaguuuuug c                                              21

<210> SEQ ID NO 16
<211> LENGTH: 23
<212> TYPE: RNA
<213> ORGANISM: Homo sapiens

<400> SEQUENCE: 16
ugcaaaagua auugcaguuu uug                                            23

<210> SEQ ID NO 17
<211> LENGTH: 23
<212> TYPE: RNA
<213> ORGANISM: Homo sapiens

<400> SEQUENCE: 17
ugcaaaagua auugcaguuu uug                                            23

<210> SEQ ID NO 18
<211> LENGTH: 22
<212> TYPE: RNA
<213> ORGANISM: Homo sapiens

<400> SEQUENCE: 18
ugagguagua gguuguaugg uu                                             22

<210> SEQ ID NO 19
<211> LENGTH: 20
<212> TYPE: RNA
<213> ORGANISM: Homo sapiens

<400> SEQUENCE: 19
aaaaguaauc guaguuuuug                                                20

<210> SEQ ID NO 20
<211> LENGTH: 22
<212> TYPE: RNA
<213> ORGANISM: Homo sapiens

<400> SEQUENCE: 20
ugugagguug gcauuguugu cu                                             22

<210> SEQ ID NO 21
<211> LENGTH: 20
<212> TYPE: RNA
<213> ORGANISM: Homo sapiens

<400> SEQUENCE: 21
aaaaguaaug gcaguuuuug                                                20

<210> SEQ ID NO 22
<211> LENGTH: 22
<212> TYPE: RNA
<213> ORGANISM: Homo sapiens

<400> SEQUENCE: 22
acaguagucu gcacauuggu ua                                             22

<210> SEQ ID NO 23
<211> LENGTH: 20
```

```
<212> TYPE: RNA
<213> ORGANISM: Homo sapiens

<400> SEQUENCE: 23
aaaaguaauc gcacuuuuug                                              20

<210> SEQ ID NO 24
<211> LENGTH: 20
<212> TYPE: RNA
<213> ORGANISM: Homo sapiens

<400> SEQUENCE: 24
aaaaguaauc gcacuuuuug                                              20

<210> SEQ ID NO 25
<211> LENGTH: 24
<212> TYPE: RNA
<213> ORGANISM: Homo sapiens

<400> SEQUENCE: 25
ggcuggucug augguagugg guua                                         24

<210> SEQ ID NO 26
<211> LENGTH: 22
<212> TYPE: RNA
<213> ORGANISM: Homo sapiens

<400> SEQUENCE: 26
acaguagucu gcacauuggu ua                                           22

<210> SEQ ID NO 27
<211> LENGTH: 20
<212> TYPE: RNA
<213> ORGANISM: Homo sapiens

<400> SEQUENCE: 27
aaaaguaauc gcagguuuug                                              20

<210> SEQ ID NO 28
<211> LENGTH: 21
<212> TYPE: RNA
<213> ORGANISM: Homo sapiens

<400> SEQUENCE: 28
ucuaguaaga guggcagucg a                                            21

<210> SEQ ID NO 29
<211> LENGTH: 22
<212> TYPE: RNA
<213> ORGANISM: Homo sapiens

<400> SEQUENCE: 29
ugauauguuu gauauauuag gu                                           22

<210> SEQ ID NO 30
<211> LENGTH: 23
<212> TYPE: RNA
<213> ORGANISM: Homo sapiens

<400> SEQUENCE: 30
uagcaccauu ugaaaucagu guu                                          23

<210> SEQ ID NO 31
```

```
<211> LENGTH: 22
<212> TYPE: RNA
<213> ORGANISM: Homo sapiens

<400> SEQUENCE: 31
uacccauugc auaucggagu ug                                              22

<210> SEQ ID NO 32
<211> LENGTH: 21
<212> TYPE: RNA
<213> ORGANISM: Homo sapiens

<400> SEQUENCE: 32
ugagaugaag cacuguagcu c                                               21

<210> SEQ ID NO 33
<211> LENGTH: 18
<212> TYPE: RNA
<213> ORGANISM: Homo sapiens

<400> SEQUENCE: 33
aaaaguacuu gcggauuu                                                   18

<210> SEQ ID NO 34
<211> LENGTH: 22
<212> TYPE: RNA
<213> ORGANISM: Homo sapiens

<400> SEQUENCE: 34
aaaaguacuu gcggauuuug cu                                              22

<210> SEQ ID NO 35
<211> LENGTH: 22
<212> TYPE: RNA
<213> ORGANISM: Homo sapiens

<400> SEQUENCE: 35
uagcaccauc ugaaaucggu ua                                              22

<210> SEQ ID NO 36
<211> LENGTH: 22
<212> TYPE: RNA
<213> ORGANISM: Homo sapiens

<400> SEQUENCE: 36
aaaaguaauu gcggauuuug cc                                              22

<210> SEQ ID NO 37
<211> LENGTH: 22
<212> TYPE: RNA
<213> ORGANISM: Homo sapiens

<400> SEQUENCE: 37
acugcaguga aggcacuugu ag                                              22

<210> SEQ ID NO 38
<211> LENGTH: 24
<212> TYPE: RNA
<213> ORGANISM: Homo sapiens

<400> SEQUENCE: 38
ggcugguccg agugcagugg uguu                                            24
```

```
<210> SEQ ID NO 39
<211> LENGTH: 22
<212> TYPE: RNA
<213> ORGANISM: Homo sapiens

<400> SEQUENCE: 39
ucagugcacu acagaacuuu gu                                                  22

<210> SEQ ID NO 40
<211> LENGTH: 22
<212> TYPE: RNA
<213> ORGANISM: Homo sapiens

<400> SEQUENCE: 40
ucguaccgug aguaauaaug cg                                                  22

<210> SEQ ID NO 41
<211> LENGTH: 20
<212> TYPE: RNA
<213> ORGANISM: Homo sapiens

<400> SEQUENCE: 41
ugagguagua ggugugugc                                                      20

<210> SEQ ID NO 42
<211> LENGTH: 22
<212> TYPE: RNA
<213> ORGANISM: Homo sapiens

<400> SEQUENCE: 42
ugagguagua guuugugcug uu                                                  22

<210> SEQ ID NO 43
<211> LENGTH: 20
<212> TYPE: RNA
<213> ORGANISM: Homo sapiens

<400> SEQUENCE: 43
gugcauugcu guugcauugc                                                     20

<210> SEQ ID NO 44
<211> LENGTH: 22
<212> TYPE: RNA
<213> ORGANISM: Homo sapiens

<400> SEQUENCE: 44
caccuugcgc uacucagguc ug                                                  22

<210> SEQ ID NO 45
<211> LENGTH: 22
<212> TYPE: RNA
<213> ORGANISM: Homo sapiens

<400> SEQUENCE: 45
aaaaguaauu gcgguuuuug cc                                                  22

<210> SEQ ID NO 46
<211> LENGTH: 21
<212> TYPE: RNA
<213> ORGANISM: Homo sapiens

<400> SEQUENCE: 46
ucagugcaug acagaacuug g                                                   21
```

-continued

```
<210> SEQ ID NO 47
<211> LENGTH: 22
<212> TYPE: RNA
<213> ORGANISM: Homo sapiens

<400> SEQUENCE: 47
aaaaguaauu gcgguuuuug cc                                                  22

<210> SEQ ID NO 48
<211> LENGTH: 21
<212> TYPE: RNA
<213> ORGANISM: Homo sapiens

<400> SEQUENCE: 48
aaaaguaauu gcgguuuuug c                                                   21

<210> SEQ ID NO 49
<211> LENGTH: 22
<212> TYPE: RNA
<213> ORGANISM: Homo sapiens

<400> SEQUENCE: 49
aaaaguaauu gcgguuuuug cc                                                  22

<210> SEQ ID NO 50
<211> LENGTH: 19
<212> TYPE: RNA
<213> ORGANISM: Homo sapiens

<400> SEQUENCE: 50
ggcggcggag gcggcggug                                                      19

<210> SEQ ID NO 51
<211> LENGTH: 21
<212> TYPE: RNA
<213> ORGANISM: Homo sapiens

<400> SEQUENCE: 51
augaccuaug aauugacaga c                                                   21

<210> SEQ ID NO 52
<211> LENGTH: 22
<212> TYPE: RNA
<213> ORGANISM: Homo sapiens

<400> SEQUENCE: 52
uuauaaagca augagacuga uu                                                  22

<210> SEQ ID NO 53
<211> LENGTH: 24
<212> TYPE: RNA
<213> ORGANISM: Homo sapiens

<400> SEQUENCE: 53
uugcagcugc cugggaguga cuuc                                                24

<210> SEQ ID NO 54
<211> LENGTH: 21
<212> TYPE: RNA
<213> ORGANISM: Homo sapiens

<400> SEQUENCE: 54
aagcacugcc uuugaaccug a                                                   21
```

<210> SEQ ID NO 55
<211> LENGTH: 22
<212> TYPE: RNA
<213> ORGANISM: Homo sapiens

<400> SEQUENCE: 55
agacccuggu cugcacucua uc                                              22

<210> SEQ ID NO 56
<211> LENGTH: 22
<212> TYPE: RNA
<213> ORGANISM: Homo sapiens

<400> SEQUENCE: 56
uguaaacauc cccgacugga ag                                              22

<210> SEQ ID NO 57
<211> LENGTH: 22
<212> TYPE: RNA
<213> ORGANISM: Homo sapiens

<400> SEQUENCE: 57
aauguuggaa uccucgcuag ag                                              22

<210> SEQ ID NO 58
<211> LENGTH: 21
<212> TYPE: RNA
<213> ORGANISM: Homo sapiens

<400> SEQUENCE: 58
cuagacugaa gcuccuugag g                                               21

<210> SEQ ID NO 59
<211> LENGTH: 21
<212> TYPE: RNA
<213> ORGANISM: Homo sapiens

<400> SEQUENCE: 59
agcucugucu gugucucuag g                                               21

<210> SEQ ID NO 60
<211> LENGTH: 22
<212> TYPE: RNA
<213> ORGANISM: Homo sapiens

<400> SEQUENCE: 60
cacuagauug ugagcuccug ga                                              22

<210> SEQ ID NO 61
<211> LENGTH: 22
<212> TYPE: RNA
<213> ORGANISM: Homo sapiens

<400> SEQUENCE: 61
ccuguucucc auuacuuggc uc                                              22

<210> SEQ ID NO 62
<211> LENGTH: 21
<212> TYPE: RNA
<213> ORGANISM: Homo sapiens

<400> SEQUENCE: 62

-continued cuccguuugc cuguuucgcu g                                          21

<210> SEQ ID NO 63
<211> LENGTH: 21
<212> TYPE: RNA
<213> ORGANISM: Homo sapiens

<400> SEQUENCE: 63
ucacagugaa ccggucucuu u                                          21

<210> SEQ ID NO 64
<211> LENGTH: 23
<212> TYPE: RNA
<213> ORGANISM: Homo sapiens

<400> SEQUENCE: 64
agugccugag ggaguaagag ccc                                        23

<210> SEQ ID NO 65
<211> LENGTH: 22
<212> TYPE: RNA
<213> ORGANISM: Homo sapiens

<400> SEQUENCE: 65
uuuugugucu cccauucccc ag                                         22

<210> SEQ ID NO 66
<211> LENGTH: 22
<212> TYPE: RNA
<213> ORGANISM: Homo sapiens

<400> SEQUENCE: 66
aaguucuguu auacacucag gc                                         22

<210> SEQ ID NO 67
<211> LENGTH: 22
<212> TYPE: RNA
<213> ORGANISM: Homo sapiens

<400> SEQUENCE: 67
cacugcacuc cagccugggu ga                                         22

<210> SEQ ID NO 68
<211> LENGTH: 22
<212> TYPE: RNA
<213> ORGANISM: Homo sapiens

<400> SEQUENCE: 68
cacugcacuc cagccugggu ga                                         22

<210> SEQ ID NO 69
<211> LENGTH: 21
<212> TYPE: RNA
<213> ORGANISM: Homo sapiens

<400> SEQUENCE: 69
gaucucacuu uguugcccag g                                          21

<210> SEQ ID NO 70
<211> LENGTH: 22
<212> TYPE: RNA
<213> ORGANISM: Homo sapiens

<400> SEQUENCE: 70
uucugccucu guccaggucc uu                                                     22

<210> SEQ ID NO 71
<211> LENGTH: 22
<212> TYPE: RNA
<213> ORGANISM: Homo sapiens

<400> SEQUENCE: 71
uccccuucug caggccugcu gg                                                     22

<210> SEQ ID NO 72
<211> LENGTH: 22
<212> TYPE: RNA
<213> ORGANISM: Homo sapiens

<400> SEQUENCE: 72
cugcccuagu cuagcugaag cu                                                     22

<210> SEQ ID NO 73
<211> LENGTH: 22
<212> TYPE: RNA
<213> ORGANISM: Homo sapiens

<400> SEQUENCE: 73
cucggccuuu gcucgcagca cu                                                     22

<210> SEQ ID NO 74
<211> LENGTH: 20
<212> TYPE: RNA
<213> ORGANISM: Homo sapiens

<400> SEQUENCE: 74
agugccugag ggaguaagag                                                        20

<210> SEQ ID NO 75
<211> LENGTH: 22
<212> TYPE: RNA
<213> ORGANISM: Homo sapiens

<400> SEQUENCE: 75
uuaucagaau cuccaggggu ac                                                     22

<210> SEQ ID NO 76
<211> LENGTH: 20
<212> TYPE: RNA
<213> ORGANISM: Homo sapiens

<400> SEQUENCE: 76
cagggucucg uucuguugcc                                                        20

<210> SEQ ID NO 77
<211> LENGTH: 22
<212> TYPE: RNA
<213> ORGANISM: Homo sapiens

<400> SEQUENCE: 77
ugagaaccac gucugcucug ag                                                     22

<210> SEQ ID NO 78
<211> LENGTH: 23
<212> TYPE: RNA
<213> ORGANISM: Homo sapiens

```
<400> SEQUENCE: 78
aaugacacga ucacucccgu uga                                          23

<210> SEQ ID NO 79
<211> LENGTH: 22
<212> TYPE: RNA
<213> ORGANISM: Homo sapiens

<400> SEQUENCE: 79
uguaaacauc cucgacugga ag                                           22

<210> SEQ ID NO 80
<211> LENGTH: 20
<212> TYPE: RNA
<213> ORGANISM: Homo sapiens

<400> SEQUENCE: 80
cacugcacuc cagccuggcu                                              20

<210> SEQ ID NO 81
<211> LENGTH: 20
<212> TYPE: RNA
<213> ORGANISM: Homo sapiens

<400> SEQUENCE: 81
cacugcacuc cagccuggcu                                              20

<210> SEQ ID NO 82
<211> LENGTH: 22
<212> TYPE: RNA
<213> ORGANISM: Homo sapiens

<400> SEQUENCE: 82
ucucugggcc ugugucuuag gc                                           22

<210> SEQ ID NO 83
<211> LENGTH: 22
<212> TYPE: RNA
<213> ORGANISM: Homo sapiens

<400> SEQUENCE: 83
caaagaauuc uccuuuuggg cu                                           22

<210> SEQ ID NO 84
<211> LENGTH: 23
<212> TYPE: RNA
<213> ORGANISM: Homo sapiens

<400> SEQUENCE: 84
acugcaaccu ccaccuccug ggu                                          23

<210> SEQ ID NO 85
<211> LENGTH: 22
<212> TYPE: RNA
<213> ORGANISM: Homo sapiens

<400> SEQUENCE: 85
cuauacgacc ugcugccuuu cu                                           22

<210> SEQ ID NO 86
<211> LENGTH: 22
<212> TYPE: RNA
<213> ORGANISM: Homo sapiens
```

-continued

<400> SEQUENCE: 86
cuggcccucu cugcccuucc gu                                          22

<210> SEQ ID NO 87
<211> LENGTH: 23
<212> TYPE: RNA
<213> ORGANISM: Homo sapiens

<400> SEQUENCE: 87
uguaaacauc cuacacucuc agc                                         23

<210> SEQ ID NO 88
<211> LENGTH: 21
<212> TYPE: RNA
<213> ORGANISM: Homo sapiens

<400> SEQUENCE: 88
uuccuggcuc ucuguugcac a                                           21

<210> SEQ ID NO 89
<211> LENGTH: 22
<212> TYPE: RNA
<213> ORGANISM: Homo sapiens

<400> SEQUENCE: 89
aauugcacgg uauccaucug ua                                          22

<210> SEQ ID NO 90
<211> LENGTH: 23
<212> TYPE: RNA
<213> ORGANISM: Homo sapiens

<400> SEQUENCE: 90
ugagcgccuc gacgacagag ccg                                         23

<210> SEQ ID NO 91
<211> LENGTH: 22
<212> TYPE: RNA
<213> ORGANISM: Homo sapiens

<400> SEQUENCE: 91
cacugcaacc ucugccuccg gu                                          22

<210> SEQ ID NO 92
<211> LENGTH: 22
<212> TYPE: RNA
<213> ORGANISM: Homo sapiens

<400> SEQUENCE: 92
ucuucucugu uuuggccaug ug                                          22

<210> SEQ ID NO 93
<211> LENGTH: 22
<212> TYPE: RNA
<213> ORGANISM: Homo sapiens

<400> SEQUENCE: 93
gcugacuccu aguccagggc uc                                          22

<210> SEQ ID NO 94
<211> LENGTH: 24
<212> TYPE: RNA

<213> ORGANISM: Homo sapiens

<400> SEQUENCE: 94
acgcccacug cuucacuuga cuag                                    24

<210> SEQ ID NO 95
<211> LENGTH: 23
<212> TYPE: RNA
<213> ORGANISM: Homo sapiens

<400> SEQUENCE: 95
ucuguauucu ccuuugccug cag                                     23

<210> SEQ ID NO 96
<211> LENGTH: 24
<212> TYPE: RNA
<213> ORGANISM: Homo sapiens

<400> SEQUENCE: 96
acucccacug cuucacuuga uuag                                    24

<210> SEQ ID NO 97
<211> LENGTH: 24
<212> TYPE: RNA
<213> ORGANISM: Homo sapiens

<400> SEQUENCE: 97
acucccacug cuugacuuga cuag                                    24

<210> SEQ ID NO 98
<211> LENGTH: 22
<212> TYPE: RNA
<213> ORGANISM: Homo sapiens

<400> SEQUENCE: 98
uugcucugcu cucccuugua cu                                      22

<210> SEQ ID NO 99
<211> LENGTH: 21
<212> TYPE: RNA
<213> ORGANISM: Homo sapiens

<400> SEQUENCE: 99
cacugcacuc cagccugggu a                                       21

<210> SEQ ID NO 100
<211> LENGTH: 22
<212> TYPE: RNA
<213> ORGANISM: Homo sapiens

<400> SEQUENCE: 100
ucaaguguca ucuguccccua gg                                     22

<210> SEQ ID NO 101
<211> LENGTH: 23
<212> TYPE: RNA
<213> ORGANISM: Homo sapiens

<400> SEQUENCE: 101
uacccuguag auccgaauuu gug                                     23

<210> SEQ ID NO 102
<211> LENGTH: 23

```
<212> TYPE: RNA
<213> ORGANISM: Homo sapiens

<400> SEQUENCE: 102
ccuccguguu accuguccuc uag                                          23

<210> SEQ ID NO 103
<211> LENGTH: 21
<212> TYPE: RNA
<213> ORGANISM: Homo sapiens

<400> SEQUENCE: 103
cugcacucca gccugggcga c                                            21

<210> SEQ ID NO 104
<211> LENGTH: 21
<212> TYPE: RNA
<213> ORGANISM: Homo sapiens

<400> SEQUENCE: 104
cccaggacag uuucagugau g                                            21

<210> SEQ ID NO 105
<211> LENGTH: 22
<212> TYPE: RNA
<213> ORGANISM: Homo sapiens

<400> SEQUENCE: 105
uucagccagg cuagugcagu cu                                           22

<210> SEQ ID NO 106
<211> LENGTH: 22
<212> TYPE: RNA
<213> ORGANISM: Homo sapiens

<400> SEQUENCE: 106
ccccgcgcag guucgaaucc ug                                           22

<210> SEQ ID NO 107
<211> LENGTH: 20
<212> TYPE: RNA
<213> ORGANISM: Homo sapiens

<400> SEQUENCE: 107
caccccacca gugcaggcug                                              20

<210> SEQ ID NO 108
<211> LENGTH: 21
<212> TYPE: RNA
<213> ORGANISM: Homo sapiens

<400> SEQUENCE: 108
uuucccuuuc cauccuggca g                                            21

<210> SEQ ID NO 109
<211> LENGTH: 22
<212> TYPE: RNA
<213> ORGANISM: Homo sapiens

<400> SEQUENCE: 109
uuucuucuua gacauggcaa cg                                           22

<210> SEQ ID NO 110
```

```
<211> LENGTH: 18
<212> TYPE: RNA
<213> ORGANISM: Homo sapiens

<400> SEQUENCE: 110
aucccaccgc ugccacac                                                   18

<210> SEQ ID NO 111
<211> LENGTH: 22
<212> TYPE: RNA
<213> ORGANISM: Homo sapiens

<400> SEQUENCE: 111
cacugcuaaa uuuggcuggc uu                                              22

<210> SEQ ID NO 112
<211> LENGTH: 22
<212> TYPE: RNA
<213> ORGANISM: Homo sapiens

<400> SEQUENCE: 112
ucuucaccug ccucugccug ca                                              22

<210> SEQ ID NO 113
<211> LENGTH: 19
<212> TYPE: RNA
<213> ORGANISM: Homo sapiens

<400> SEQUENCE: 113
uggcccaaga ccucagacc                                                  19

<210> SEQ ID NO 114
<211> LENGTH: 22
<212> TYPE: RNA
<213> ORGANISM: Homo sapiens

<400> SEQUENCE: 114
auggccagag cucacacaga gg                                              22

<210> SEQ ID NO 115
<211> LENGTH: 21
<212> TYPE: RNA
<213> ORGANISM: Homo sapiens

<400> SEQUENCE: 115
ucagcuacua ccucuauuag g                                               21

<210> SEQ ID NO 116
<211> LENGTH: 20
<212> TYPE: RNA
<213> ORGANISM: Homo sapiens

<400> SEQUENCE: 116
cuggcugcuu cccuuggucu                                                 20

<210> SEQ ID NO 117
<211> LENGTH: 22
<212> TYPE: RNA
<213> ORGANISM: Homo sapiens

<400> SEQUENCE: 117
aucccuuuau cuguccucua gg                                              22
```

```
<210> SEQ ID NO 118
<211> LENGTH: 21
<212> TYPE: RNA
<213> ORGANISM: Homo sapiens

<400> SEQUENCE: 118 aggggggaaag uucuauaguc c                                             21

<210> SEQ ID NO 119
<211> LENGTH: 23
<212> TYPE: RNA
<213> ORGANISM: Homo sapiens

<400> SEQUENCE: 119
uacccuguag aaccgaauuu gug                                            23

<210> SEQ ID NO 120
<211> LENGTH: 21
<212> TYPE: RNA
<213> ORGANISM: Homo sapiens

<400> SEQUENCE: 120
caugccacug cacuccagcc u                                              21

<210> SEQ ID NO 121
<211> LENGTH: 23
<212> TYPE: RNA
<213> ORGANISM: Homo sapiens

<400> SEQUENCE: 121
ccucuucuca gaacacuucc ugg                                            23

<210> SEQ ID NO 122
<211> LENGTH: 22
<212> TYPE: RNA
<213> ORGANISM: Homo sapiens

<400> SEQUENCE: 122
uuugugaccu gguccacuaa cc                                             22

<210> SEQ ID NO 123
<211> LENGTH: 22
<212> TYPE: RNA
<213> ORGANISM: Homo sapiens

<400> SEQUENCE: 123
cuuucagucg gauguuugca gc                                             22

<210> SEQ ID NO 124
<211> LENGTH: 21
<212> TYPE: RNA
<213> ORGANISM: Homo sapiens

<400> SEQUENCE: 124
uccggauccg gcuccgcgcc u                                              21

<210> SEQ ID NO 125
<211> LENGTH: 21
<212> TYPE: RNA
<213> ORGANISM: Homo sapiens

<400> SEQUENCE: 125
cccgccuguc ucucuuugc a                                               21
```

<210> SEQ ID NO 126
<211> LENGTH: 21
<212> TYPE: RNA
<213> ORGANISM: Homo sapiens

<400> SEQUENCE: 126
uauggagguc ucgucuggc u                                                    21

<210> SEQ ID NO 127
<211> LENGTH: 22
<212> TYPE: RNA
<213> ORGANISM: Homo sapiens

<400> SEQUENCE: 127
cuauacaacc uacugccuuc cc                                                  22

<210> SEQ ID NO 128
<211> LENGTH: 22
<212> TYPE: RNA
<213> ORGANISM: Homo sapiens

<400> SEQUENCE: 128
uccgucucag uuacuuuaua gc                                                  22

<210> SEQ ID NO 129
<211> LENGTH: 22
<212> TYPE: RNA
<213> ORGANISM: Homo sapiens

<400> SEQUENCE: 129
ucaggcucag uccccucccg au                                                  22

<210> SEQ ID NO 130
<211> LENGTH: 22
<212> TYPE: RNA
<213> ORGANISM: Homo sapiens

<400> SEQUENCE: 130
cuuucagucg gauguuuaca gc                                                  22

<210> SEQ ID NO 131
<211> LENGTH: 20
<212> TYPE: RNA
<213> ORGANISM: Homo sapiens

<400> SEQUENCE: 131
gaccacacuc cauccugggc                                                     20

<210> SEQ ID NO 132
<211> LENGTH: 22
<212> TYPE: RNA
<213> ORGANISM: Homo sapiens

<400> SEQUENCE: 132
acucaaaaga uggcggcacu uu                                                  22

<210> SEQ ID NO 133
<211> LENGTH: 22
<212> TYPE: RNA
<213> ORGANISM: Homo sapiens

<400> SEQUENCE: 133
uuccaugccu ccuagaaguu cc                                                  22

```
<210> SEQ ID NO 134
<211> LENGTH: 19
<212> TYPE: RNA
<213> ORGANISM: Homo sapiens

<400> SEQUENCE: 134
cacugcaacc ucugccucc                                                    19

<210> SEQ ID NO 135
<211> LENGTH: 21
<212> TYPE: RNA
<213> ORGANISM: Homo sapiens

<400> SEQUENCE: 135
aaagacuucc uucucucgcc u                                                 21

<210> SEQ ID NO 136
<211> LENGTH: 22
<212> TYPE: RNA
<213> ORGANISM: Homo sapiens

<400> SEQUENCE: 136
uccggaugug cugaccccug cg                                                22

<210> SEQ ID NO 137
<211> LENGTH: 23
<212> TYPE: RNA
<213> ORGANISM: Homo sapiens

<400> SEQUENCE: 137
ccugaccccc augucgccuc ugu                                               23

<210> SEQ ID NO 138
<211> LENGTH: 23
<212> TYPE: RNA
<213> ORGANISM: Homo sapiens

<400> SEQUENCE: 138
ccugaccccc augucgccuc ugu                                               23

<210> SEQ ID NO 139
<211> LENGTH: 23
<212> TYPE: RNA
<213> ORGANISM: Homo sapiens

<400> SEQUENCE: 139
ccugaccccc augucgccuc ugu                                               23

<210> SEQ ID NO 140
<211> LENGTH: 23
<212> TYPE: RNA
<213> ORGANISM: Homo sapiens

<400> SEQUENCE: 140
ccugaccccc augucgccuc ugu                                               23

<210> SEQ ID NO 141
<211> LENGTH: 22
<212> TYPE: RNA
<213> ORGANISM: Homo sapiens

<400> SEQUENCE: 141
```

```
cacugcaacc ucugccuccc ga                                                  22

<210> SEQ ID NO 142
<211> LENGTH: 20
<212> TYPE: RNA
<213> ORGANISM: Homo sapiens

<400> SEQUENCE: 142
cuucgaaagc ggcuucggcu                                                     20

<210> SEQ ID NO 143
<211> LENGTH: 21
<212> TYPE: RNA
<213> ORGANISM: Homo sapiens

<400> SEQUENCE: 143
guuccugcug aacugagcca g                                                   21

<210> SEQ ID NO 144
<211> LENGTH: 22
<212> TYPE: RNA
<213> ORGANISM: Homo sapiens

<400> SEQUENCE: 144
uguaaacauc cuacacucag cu                                                  22

<210> SEQ ID NO 145
<211> LENGTH: 22
<212> TYPE: RNA
<213> ORGANISM: Homo sapiens

<400> SEQUENCE: 145
auucuaauuu cuccacgucu uu                                                  22

<210> SEQ ID NO 146
<211> LENGTH: 22
<212> TYPE: RNA
<213> ORGANISM: Homo sapiens

<400> SEQUENCE: 146
uuaguggcuc ccucugccug ca                                                  22

<210> SEQ ID NO 147
<211> LENGTH: 21
<212> TYPE: RNA
<213> ORGANISM: Homo sapiens

<400> SEQUENCE: 147
cugacuguug ccguccucca g                                                   21

<210> SEQ ID NO 148
<211> LENGTH: 22
<212> TYPE: RNA
<213> ORGANISM: Homo sapiens

<400> SEQUENCE: 148
ugucuugcuc uguugcccag gu                                                  22

<210> SEQ ID NO 149
<211> LENGTH: 22
<212> TYPE: RNA
<213> ORGANISM: Homo sapiens

<400> SEQUENCE: 149
```

-continued ccugcaacuu ugccugauca ga                    22

<210> SEQ ID NO 150
<211> LENGTH: 20
<212> TYPE: RNA
<213> ORGANISM: Homo sapiens

<400> SEQUENCE: 150
cugcacucca gccugggcga                       20

<210> SEQ ID NO 151
<211> LENGTH: 22
<212> TYPE: RNA
<213> ORGANISM: Homo sapiens

<400> SEQUENCE: 151
auccgcgcuc ugacucucug cc                    22

<210> SEQ ID NO 152
<211> LENGTH: 22
<212> TYPE: RNA
<213> ORGANISM: Homo sapiens

<400> SEQUENCE: 152
accacugacc guugacugua cc                    22

<210> SEQ ID NO 153
<211> LENGTH: 22
<212> TYPE: RNA
<213> ORGANISM: Homo sapiens

<400> SEQUENCE: 153
uuucccuuca gagccuggcu uu                    22

<210> SEQ ID NO 154
<211> LENGTH: 22
<212> TYPE: RNA
<213> ORGANISM: Homo sapiens

<400> SEQUENCE: 154
uguccucuag ggccugcagu cu                    22

<210> SEQ ID NO 155
<211> LENGTH: 19
<212> TYPE: RNA
<213> ORGANISM: Homo sapiens

<400> SEQUENCE: 155
aucccaccac ugccaccau                        19

<210> SEQ ID NO 156
<211> LENGTH: 22
<212> TYPE: RNA
<213> ORGANISM: Homo sapiens

<400> SEQUENCE: 156
uuggugagga ccccaagcuc gg                    22

<210> SEQ ID NO 157
<211> LENGTH: 19
<212> TYPE: RNA
<213> ORGANISM: Homo sapiens

```
<400> SEQUENCE: 157
cacugcaacc ucugccucc                                              19

<210> SEQ ID NO 158
<211> LENGTH: 22
<212> TYPE: RNA
<213> ORGANISM: Homo sapiens

<400> SEQUENCE: 158 uugggggaaac ggccgcugag ug                                         22

<210> SEQ ID NO 159
<211> LENGTH: 22
<212> TYPE: RNA
<213> ORGANISM: Homo sapiens

<400> SEQUENCE: 159
ucaguuccag gccaaccagg cu                                          22

<210> SEQ ID NO 160
<211> LENGTH: 21
<212> TYPE: RNA
<213> ORGANISM: Homo sapiens

<400> SEQUENCE: 160
caugguccau uuugcucugc u                                           21

<210> SEQ ID NO 161
<211> LENGTH: 17
<212> TYPE: RNA
<213> ORGANISM: Homo sapiens

<400> SEQUENCE: 161
ucccaccgcu gccaccc                                                17

<210> SEQ ID NO 162
<211> LENGTH: 25
<212> TYPE: RNA
<213> ORGANISM: Homo sapiens

<400> SEQUENCE: 162
cuuccagacg cuccgcccca cgucg                                       25

<210> SEQ ID NO 163
<211> LENGTH: 23
<212> TYPE: RNA
<213> ORGANISM: Homo sapiens

<400> SEQUENCE: 163
ugucacucgg cucggcccac uac                                         23

<210> SEQ ID NO 164
<211> LENGTH: 22
<212> TYPE: RNA
<213> ORGANISM: Homo sapiens

<400> SEQUENCE: 164
cagggccuca cuguaucgcc ca                                          22

<210> SEQ ID NO 165
<211> LENGTH: 24
<212> TYPE: RNA
<213> ORGANISM: Homo sapiens
```

```
<400> SEQUENCE: 165
aaagacauag gauagaguca ccuc                                          24

<210> SEQ ID NO 166
<211> LENGTH: 20
<212> TYPE: RNA
<213> ORGANISM: Homo sapiens

<400> SEQUENCE: 166
ugagcccugu ccucccgcag                                               20

<210> SEQ ID NO 167
<211> LENGTH: 22
<212> TYPE: RNA
<213> ORGANISM: Homo sapiens

<400> SEQUENCE: 167
cuccugacuc cagguccugu gu                                            22

<210> SEQ ID NO 168
<211> LENGTH: 22
<212> TYPE: RNA
<213> ORGANISM: Homo sapiens

<400> SEQUENCE: 168
uucaaguaau ccaggauagg cu                                            22

<210> SEQ ID NO 169
<211> LENGTH: 18
<212> TYPE: RNA
<213> ORGANISM: Homo sapiens

<400> SEQUENCE: 169
aucccacccc ugcccca                                                  18

<210> SEQ ID NO 170
<211> LENGTH: 18
<212> TYPE: RNA
<213> ORGANISM: Homo sapiens

<400> SEQUENCE: 170
aucccaccuc ugccacca                                                 18

<210> SEQ ID NO 171
<211> LENGTH: 22
<212> TYPE: RNA
<213> ORGANISM: Homo sapiens

<400> SEQUENCE: 171
uagcaccauu ugaaaucggu ua                                            22

<210> SEQ ID NO 172
<211> LENGTH: 22
<212> TYPE: RNA
<213> ORGANISM: Homo sapiens

<400> SEQUENCE: 172
uagcaccauc ugaaaucggu ua                                            22

<210> SEQ ID NO 173
<211> LENGTH: 22
<212> TYPE: RNA
```

```
<213> ORGANISM: Homo sapiens

<400> SEQUENCE: 173
ugagguagga gguuguauag uu                                          22

<210> SEQ ID NO 174
<211> LENGTH: 22
<212> TYPE: RNA
<213> ORGANISM: Homo sapiens

<400> SEQUENCE: 174
ugagguagua gguuguauag uu                                          22

<210> SEQ ID NO 175
<211> LENGTH: 22
<212> TYPE: RNA
<213> ORGANISM: Homo sapiens

<400> SEQUENCE: 175
ugagguagua gauuguauag uu                                          22

<210> SEQ ID NO 176
<211> LENGTH: 23
<212> TYPE: RNA
<213> ORGANISM: Homo sapiens

<400> SEQUENCE: 176
uagcaccauu ugaaaucagu guu                                         23

<210> SEQ ID NO 177
<211> LENGTH: 22
<212> TYPE: RNA
<213> ORGANISM: Homo sapiens

<400> SEQUENCE: 177
ugagguagua aguuguauug uu                                          22

<210> SEQ ID NO 178
<211> LENGTH: 23
<212> TYPE: RNA
<213> ORGANISM: Homo sapiens

<400> SEQUENCE: 178
aaugacacga ucacucccgu uga                                         23

<210> SEQ ID NO 179
<211> LENGTH: 22
<212> TYPE: RNA
<213> ORGANISM: Homo sapiens

<400> SEQUENCE: 179
ugucaguuug ucaaauaccc ca                                          22

<210> SEQ ID NO 180
<211> LENGTH: 22
<212> TYPE: RNA
<213> ORGANISM: Homo sapiens

<400> SEQUENCE: 180
accacugacc guugacugua cc                                          22

<210> SEQ ID NO 181
<211> LENGTH: 22
```

```
<212> TYPE: RNA
<213> ORGANISM: Homo sapiens

<400> SEQUENCE: 181
ucagugcauc acagaacuuu gu                                          22

<210> SEQ ID NO 182
<211> LENGTH: 21
<212> TYPE: RNA
<213> ORGANISM: Homo sapiens

<400> SEQUENCE: 182
aagcacugcc uuugaaccug a                                           21

<210> SEQ ID NO 183
<211> LENGTH: 22
<212> TYPE: RNA
<213> ORGANISM: Homo sapiens

<400> SEQUENCE: 183
aaaaguaauc gcgguuuuug uc                                          22

<210> SEQ ID NO 184
<211> LENGTH: 23
<212> TYPE: RNA
<213> ORGANISM: Homo sapiens

<400> SEQUENCE: 184
agugccugag ggaguaagag ccc                                         23

<210> SEQ ID NO 185
<211> LENGTH: 22
<212> TYPE: RNA
<213> ORGANISM: Homo sapiens

<400> SEQUENCE: 185
auauaauaca accugcuaag ug                                          22

<210> SEQ ID NO 186
<211> LENGTH: 23
<212> TYPE: RNA
<213> ORGANISM: Homo sapiens

<400> SEQUENCE: 186
ugagcgccuc gacgacagag ccg                                         23

<210> SEQ ID NO 187
<211> LENGTH: 22
<212> TYPE: RNA
<213> ORGANISM: Homo sapiens

<400> SEQUENCE: 187
ugaccuggga cucggacagc ug                                          22

<210> SEQ ID NO 188
<211> LENGTH: 23
<212> TYPE: RNA
<213> ORGANISM: Homo sapiens

<400> SEQUENCE: 188
ccugaccccc augucgccuc ugu                                         23

<210> SEQ ID NO 189
```

```
<211> LENGTH: 23
<212> TYPE: RNA
<213> ORGANISM: Homo sapiens

<400> SEQUENCE: 189
ccugaccccc augucgccuc ugu                                              23

<210> SEQ ID NO 190
<211> LENGTH: 23
<212> TYPE: RNA
<213> ORGANISM: Homo sapiens

<400> SEQUENCE: 190
ccugaccccc augucgccuc ugu                                              23

<210> SEQ ID NO 191
<211> LENGTH: 23
<212> TYPE: RNA
<213> ORGANISM: Homo sapiens

<400> SEQUENCE: 191
ccugaccccc augucgccuc ugu                                              23

<210> SEQ ID NO 192
<211> LENGTH: 20
<212> TYPE: RNA
<213> ORGANISM: Homo sapiens

<400> SEQUENCE: 192
agugccugag ggaguaagag                                                  20

<210> SEQ ID NO 193
<211> LENGTH: 22
<212> TYPE: RNA
<213> ORGANISM: Homo sapiens

<400> SEQUENCE: 193
acaguagucu gcacauuggu ua                                               22

<210> SEQ ID NO 194
<211> LENGTH: 22
<212> TYPE: RNA
<213> ORGANISM: Homo sapiens

<400> SEQUENCE: 194
acaguagucu gcacauuggu ua                                               22

<210> SEQ ID NO 195
<211> LENGTH: 22
<212> TYPE: RNA
<213> ORGANISM: Homo sapiens

<400> SEQUENCE: 195
uacccauugc auaucggagu ug                                               22

<210> SEQ ID NO 196
<211> LENGTH: 22
<212> TYPE: RNA
<213> ORGANISM: Homo sapiens

<400> SEQUENCE: 196
ugauauguuu gauauauuag gu                                               22
```

```
<210> SEQ ID NO 197
<211> LENGTH: 21
<212> TYPE: RNA
<213> ORGANISM: Homo sapiens

<400> SEQUENCE: 197
uccggauccg gcuccgcgcc u                                              21

<210> SEQ ID NO 198
<211> LENGTH: 23
<212> TYPE: RNA
<213> ORGANISM: Homo sapiens

<400> SEQUENCE: 198
ugcaaaagua auugcaguuu uug                                            23

<210> SEQ ID NO 199
<211> LENGTH: 21
<212> TYPE: RNA
<213> ORGANISM: Homo sapiens

<400> SEQUENCE: 199
aaaaguaauu gcaguuuuug c                                              21

<210> SEQ ID NO 200
<211> LENGTH: 23
<212> TYPE: RNA
<213> ORGANISM: Homo sapiens

<400> SEQUENCE: 200
ugcaaaagua auugcaguuu uug                                            23

<210> SEQ ID NO 201
<211> LENGTH: 23
<212> TYPE: RNA
<213> ORGANISM: Homo sapiens

<400> SEQUENCE: 201
ugcaaaagua auugcaguuu uug                                            23

<210> SEQ ID NO 202
<211> LENGTH: 20
<212> TYPE: RNA
<213> ORGANISM: Homo sapiens

<400> SEQUENCE: 202
aaaaguaauc guaguuuuug                                                20

<210> SEQ ID NO 203
<211> LENGTH: 20
<212> TYPE: RNA
<213> ORGANISM: Homo sapiens

<400> SEQUENCE: 203
aaaaguaauc gcacuuuuug                                                20

<210> SEQ ID NO 204
<211> LENGTH: 20
<212> TYPE: RNA
<213> ORGANISM: Homo sapiens

<400> SEQUENCE: 204
aaaaguaauc gcacuuuuug                                                20
```

```
<210> SEQ ID NO 205
<211> LENGTH: 22
<212> TYPE: RNA
<213> ORGANISM: Homo sapiens

<400> SEQUENCE: 205
ugagguagua gguuguaugg uu                                              22

<210> SEQ ID NO 206
<211> LENGTH: 20
<212> TYPE: RNA
<213> ORGANISM: Homo sapiens

<400> SEQUENCE: 206
aaaaguaauc gcagguuuug                                                 20

<210> SEQ ID NO 207
<211> LENGTH: 20
<212> TYPE: RNA
<213> ORGANISM: Homo sapiens

<400> SEQUENCE: 207
aaaaguaaug gcaguuuuug                                                 20

<210> SEQ ID NO 208
<211> LENGTH: 21
<212> TYPE: RNA
<213> ORGANISM: Homo sapiens

<400> SEQUENCE: 208
ucagugcaug acagaacuug g                                               21

<210> SEQ ID NO 209
<211> LENGTH: 22
<212> TYPE: RNA
<213> ORGANISM: Homo sapiens

<400> SEQUENCE: 209
uagcagcaca uaaugguuug ug                                              22

<210> SEQ ID NO 210
<211> LENGTH: 23
<212> TYPE: RNA
<213> ORGANISM: Homo sapiens

<400> SEQUENCE: 210
cggguagaga gggcagugggg agg                                            23

<210> SEQ ID NO 211
<211> LENGTH: 19
<212> TYPE: RNA
<213> ORGANISM: Homo sapiens

<400> SEQUENCE: 211
cacugcaacc ucugccucc                                                  19

<210> SEQ ID NO 212
<211> LENGTH: 22
<212> TYPE: RNA
<213> ORGANISM: Homo sapiens

<400> SEQUENCE: 212
aagggcuucc ucucugcagg ac                                              22
```

```
<210> SEQ ID NO 213
<211> LENGTH: 20
<212> TYPE: RNA
<213> ORGANISM: Homo sapiens

<400> SEQUENCE: 213
ugagguagua gguggugugc                                               20

<210> SEQ ID NO 214
<211> LENGTH: 21
<212> TYPE: RNA
<213> ORGANISM: Homo sapiens

<400> SEQUENCE: 214
caaaacguga ggcgcugcua u                                             21

<210> SEQ ID NO 215
<211> LENGTH: 22
<212> TYPE: RNA
<213> ORGANISM: Homo sapiens

<400> SEQUENCE: 215
ucagugcacu acagaacuuu gu                                            22

<210> SEQ ID NO 216
<211> LENGTH: 22
<212> TYPE: RNA
<213> ORGANISM: Homo sapiens

<400> SEQUENCE: 216
caccuugcgc uacucagguc ug                                            22

<210> SEQ ID NO 217
<211> LENGTH: 21
<212> TYPE: RNA
<213> ORGANISM: Homo sapiens

<400> SEQUENCE: 217
ucuaguaaga guggcagucg a                                             21

<210> SEQ ID NO 218
<211> LENGTH: 22
<212> TYPE: RNA
<213> ORGANISM: Homo sapiens

<400> SEQUENCE: 218
agagguagua gguugcauag uu                                            22

<210> SEQ ID NO 219
<211> LENGTH: 22
<212> TYPE: RNA
<213> ORGANISM: Homo sapiens

<400> SEQUENCE: 219
aauguuggaa uccucgcuag ag                                            22

<210> SEQ ID NO 220
<211> LENGTH: 19
<212> TYPE: RNA
<213> ORGANISM: Homo sapiens

<400> SEQUENCE: 220
```

```
cacugcaacc ucugccucc                                            19

<210> SEQ ID NO 221
<211> LENGTH: 22
<212> TYPE: RNA
<213> ORGANISM: Homo sapiens

<400> SEQUENCE: 221
uuauaauaca accugauaag ug                                        22

<210> SEQ ID NO 222
<211> LENGTH: 22
<212> TYPE: RNA
<213> ORGANISM: Homo sapiens

<400> SEQUENCE: 222
uccagcauca gugauuuugu ug                                        22

<210> SEQ ID NO 223
<211> LENGTH: 22
<212> TYPE: RNA
<213> ORGANISM: Homo sapiens

<400> SEQUENCE: 223
uuauaaagca augagacuga uu                                        22

<210> SEQ ID NO 224
<211> LENGTH: 22
<212> TYPE: RNA
<213> ORGANISM: Homo sapiens

<400> SEQUENCE: 224
cacugcacuc cagccugggu ga                                        22

<210> SEQ ID NO 225
<211> LENGTH: 22
<212> TYPE: RNA
<213> ORGANISM: Homo sapiens

<400> SEQUENCE: 225
cacugcacuc cagccugggu ga                                        22

<210> SEQ ID NO 226
<211> LENGTH: 21
<212> TYPE: RNA
<213> ORGANISM: Homo sapiens

<400> SEQUENCE: 226
cccaggacag uuucagugau g                                         21

<210> SEQ ID NO 227
<211> LENGTH: 18
<212> TYPE: RNA
<213> ORGANISM: Homo sapiens

<400> SEQUENCE: 227
aucccaccuc ugcuacca                                             18

<210> SEQ ID NO 228
<211> LENGTH: 21
<212> TYPE: RNA
<213> ORGANISM: Homo sapiens

<400> SEQUENCE: 228
```

-continued cuagacugaa gcuccuugag g                                    21

<210> SEQ ID NO 229
<211> LENGTH: 22
<212> TYPE: RNA
<213> ORGANISM: Homo sapiens

<400> SEQUENCE: 229
ucggccugac cacccacccc ac                                   22

<210> SEQ ID NO 230
<211> LENGTH: 22
<212> TYPE: RNA
<213> ORGANISM: Homo sapiens

<400> SEQUENCE: 230
cugcccuggc ccgagggacc ga                                   22

<210> SEQ ID NO 231
<211> LENGTH: 18
<212> TYPE: RNA
<213> ORGANISM: Homo sapiens

<400> SEQUENCE: 231
aaaaguacuu gcggauuu                                        18

<210> SEQ ID NO 232
<211> LENGTH: 22
<212> TYPE: RNA
<213> ORGANISM: Homo sapiens

<400> SEQUENCE: 232
aaaaguacuu gcggauuuug cu                                   22

<210> SEQ ID NO 233
<211> LENGTH: 21
<212> TYPE: RNA
<213> ORGANISM: Homo sapiens

<400> SEQUENCE: 233
agaccuacuu aucuaccaac a                                    21

<210> SEQ ID NO 234
<211> LENGTH: 22
<212> TYPE: RNA
<213> ORGANISM: Homo sapiens

<400> SEQUENCE: 234
uguaaacauc cccgacugga ag                                   22

<210> SEQ ID NO 235
<211> LENGTH: 22
<212> TYPE: RNA
<213> ORGANISM: Homo sapiens

<400> SEQUENCE: 235
aaucugagaa ggcgcacaag gu                                   22